United States Patent [19]
Ikeda et al.

[11] Patent Number: 5,952,355
[45] Date of Patent: Sep. 14, 1999

[54] PROPENONE DERIVATIVES

[75] Inventors: Shun-Ichi Ikeda, Machida; Uichiro Kimura, Fukuoka; Tadashi Ashizawa, Numazu; Katsushige Gomi, Susono; Hiromitsu Saito, Kawasaki; Masaji Kasai, Fujisawa; Junji Kanazawa, Sunto-gun; Kimihito Sasaki, Sunto-gun; Etsuko Nukui, Sunto-gun; Masami Okabe, Mishima; Soichiro Sato, Mishima, all of Japan

[73] Assignee: Kyowa Hakko Kogyo Co., Ltd., Tokyo, Japan

[21] Appl. No.: 08/757,080

[22] Filed: Nov. 26, 1996

Related U.S. Application Data

[63] Continuation-in-part of application No. 08/641,699, May 2, 1996, abandoned, which is a continuation-in-part of application No. 08/491,928, Jul. 13, 1995, abandoned.

[30] Foreign Application Priority Data

| | | | |
|---|---|---|---|
| Nov. 17, 1993 | [JP] | Japan | 5-288091 |
| May 10, 1995 | [JP] | Japan | 7-111741 |
| Dec. 1, 1995 | [JP] | Japan | 7-313998 |

[51] Int. Cl.$^6$ ............ A61K 31/40; A61K 31/44; C07D 209/12; C07D 209/32; C07D 209/40
[52] U.S. Cl. ............ 514/339; 514/414; 514/419; 546/278.1; 548/465; 548/494; 548/500
[58] Field of Search ............ 548/510, 465, 548/494, 500; 514/339, 414, 419; 546/278.1

[56] References Cited

U.S. PATENT DOCUMENTS

| | | | |
|---|---|---|---|
| 4,753,965 | 6/1988 | Stemerick et al. | 514/647 |
| 4,863,968 | 9/1989 | Edwards et al. | 514/646 |
| 4,904,697 | 2/1990 | Sunkara et al. | 514/629 |

FOREIGN PATENT DOCUMENTS

| | | |
|---|---|---|
| 680950 | 11/1995 | European Pat. Off. . |
| 2230349 | 12/1974 | France . |
| 95/19169 | 7/1995 | WIPO . |

OTHER PUBLICATIONS

Cancer Research, vol. 54, No. 23 (Dec. 1, 1994), pp. 6106–6114.
Chemical Abstracts, vol. 78, No. 5, Feb. 5, 1973, No. 29910t.
Antonyuk et al., Zh. Obshch. Khim., 42(8), 1706–1714, 1972.

*Primary Examiner*—Fiona T. Powers
*Attorney, Agent, or Firm*—Fitzpatrick, Cella, Harper & Scinto

[57] ABSTRACT

The present invention relates to propenone derivatives represented by the following formula (I):

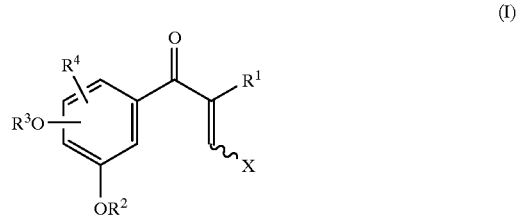

wherein $R^1$ represents hydrogen, substituted or unsubstituted lower alkyl, substituted or unsubstituted aryl, or $YR^5$ (wherein Y represents S or O; and $R^5$ represents substituted or unsubstituted lower alkyl, substituted or unsubstituted aryl, substituted or unsubstituted heteroaryl, or a substituted or unsubstituted cyclic ether residue); $R^2$ and $R^3$ independently represent hydrogen, lower alkyl, or substituted or unsubstituted aralkyl, or alternatively $R^2$ and $R^3$ are combined to form substituted or unsubstituted methylene or ethylene; $R^4$ represents hydrogen, hydroxy, lower alkyl, substituted or unsubstituted aralkyl, lower alkoxy, substituted or unsubstituted aralkyloxy, or halogen; and X represents substituted or unsubstituted indolyl; or pharmaceutically acceptable salts thereof.

26 Claims, No Drawings

PROPENONE DERIVATIVES

CROSS REFERENCE TO RELATED APPLICATION

This application is a continuation-in-part of application Ser. No. 08/641,699, filed May 2, 1996, now abandoned which is a continuation-in-part of application Ser. No. 08/491,928, filed Jul. 13, 1995, now abandoned.

TECHNICAL FIELD

The present invention relates to propenone derivatives having an antitumor activity, an immunosuppresive activity, and a therapeutic effect for an autoimmune disease.

BACKGROUND ART

Typical examples of compounds having an antitumor activity include mitomycin C, adriamycin, vincristine, and the like, all of which are clinically useful as anticancer agents. However, since each of the compounds also has adverse effects such as myelotoxicity, cardiotoxicity, nerve damage, etc., a novel anticancer agent having less adverse effects is demanded. Further, an excellent immunosuppresive agent and a therapeutic agent for an autoimmune disease having reduced adverse effects are always demanded.

Chalcone derivatives are known as having the activity to inhibit polymerization of tubulin [Journal of the Medicinal Chemistry (J. Med. Chem.), 33, 1948 (1990) and Journal of Natural Products (J. Nat. Prod.), 56, 1718 (1993)]. Chalcone derivatives are also known as having an anticancer activity, being useful as a therapeutic agent for gout, and being useful as a therapeutic agent for multiple sclerosis (U. S. Pat. Nos. 4,904,697, 4,863,968, and 4,753,965, respectively). 3-Indolyl-1-phenyl-2-propen-1-one derivatives are known as inhibiting the tyrosine-phospholylation of cell growth factor receptor [Cancer Research (Cancer Res.), 54, 6106 (1994) and WO 91/16305], being useful as an organic nonlinear optical material (Japanese Published Unexamined Patent Application No. 255426/91), and having an antiallergic activity [Khim.-Farm. Zh., 25, 18 (1991)].

Further, 3-(indol-3-yl)-1-phenyl-2-propen-1-one derivatives are disclosed in French Patent No. 2230349, Khim. Geterotsikl. Soedin, 1066 (1970), Khim. Geterotsikl. Soedin, 268 (1969), Khim. Geterotsikl. Soedin, 399 (1970), Farmaco Ed. Sci., 26, 591 (1971), etc.

DISCLOSURE OF THE INVENTION

The present invention relates to propenone derivatives represented by the following formula (I):

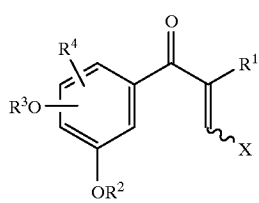

(I)

wherein $R^1$ represents hydrogen, substituted or unsubstituted lower alkyl, substituted or unsubstituted aryl, or $YR^5$ (wherein Y represents S or O; and $R^5$ represents substituted or unsubstituted lower alkyl, substituted or unsubstituted aryl, substituted or unsubstituted heteroaryl, or a substituted or unsubstituted cyclic ether residue); $R^2$ and $R^3$ independently represent hydrogen, lower alkyl, or substituted or unsubstituted aralkyl, or alternatively $R^2$ and $R^3$ are combined to form substituted or unsubstituted methylene or ethylene; $R^4$ represents hydrogen, hydroxy, lower alkyl, substituted or unsubstituted aralkyl, lower alkoxy, substituted or unsubstituted aralkyloxy, or halogen; and X represents substituted or unsubstituted indolyl, with the proviso that when $R^1$ is hydrogen, unsubstituted lower alkyl, or substituted or unsubstituted aryl, and $OR^3$ is on the 2-position or 6-position of the benzene ring, $R^3$ is lower alkyl, or substituted or unsubstituted aralkyl, or $R^2$ and $R^3$ are combined to form substituted or unsubstituted methylene or ethylene; that when $R^1$ is hydrogen, unsubstituted lower alkyl, or substituted or unsubstituted aryl, and $R^4$ is on the 2-position or 6-position of the benzene ring, $R^4$ is hydrogen, lower alkyl, substituted or unsubstituted aralkyl, lower alkoxy, substituted or unsubstituted aralkyloxy, or halogen; and that when $R^1$ is hydrogen, unsubstituted lower alkyl, or substituted or unsubstituted aryl, $R^2$ is methyl, and $OR^3$ is 4-methoxy, $R^4$ is hydroxy, lower alkyl, substituted or unsubstituted aralkyl, lower alkoxy, substituted or unsubstituted aralkyloxy, or halogen; or pharmaceutically acceptable salts thereof.

Compounds represented by the formula (I) are hereinafter referred to as Compounds (I). Compounds (Ia), (I-1), (Ia-1), and the like are included in Compounds (I). The same applies to the compounds represented by other formula numbers.

In the definitions of the groups of formula (I), the lower alkyl and the lower alkyl moiety of the lower alkoxy mean a straight-chain or branched alkyl group having 1 to 6 carbon atoms, such as methyl, ethyl, propyl, isopropyl, butyl, 2-butyl, isobutyl, tert-butyl, 1-pentyl, 2-pentyl, 3-pentyl, isoamyl, neopentyl, and hexyl. The aryl means phenyl, naphthyl, and the like, and the heteroaryl means pyridyl, pyrazinyl, pyrimidinyl, pyridazinyl, quinolinyl, isoquinolinyl, phthalazinyl, quinazolinyl, quinoxalinyl, naphthyridinyl, pyrrolyl, pyrazolyl, imidazolyl, triazolyl, tetrazolyl, thienyl, furyl, thiazolyl, oxazolyl, indolyl, indazolyl, benzimidazolyl, benzotriazolyl, purinyl, and the like. The cyclic ether residue means a cyclic ether residue having 2 to 6 carbon atoms, such as oxiranyl, oxetanyl, tetrahydrofuranyl, and tetrahydropyranyl. The aralkyl and the aralkyl moiety of the aralkyloxy mean an aralkyl group having 7 to 15 carbon atoms, such as benzyl, phenethyl, benzhydryl, and naphthylmethyl. The halogen includes fluorine, chorine, bromide, and iodine.

The substituted alkyl has the same or different 1 to 4 substituents such as vinyl, hydroxy, lower alkoxy, aryloxy, amino, lower alkylamino, di(lower alkyl)amino, lower alkanoylamino, lower alkoxycarbonylamino, halogen, nitro, carboxy, lower alkanoyl, lower alkoxycarbonyl, tri(lower alkyl)silyl, and a cyclic ether residue. The substituted aryl, substituted heteroaryl, substituted cyclic ether residue, substituted aralkyl, and substituted aralkyloxy each has the same or different 1 to 4 substituents such as lower alkyl, vinyl, hydroxy, hydroxymethyl, lower alkoxy, aryloxy, lower alkanoyl, lower alkoxycarbonyl, amino, lower alkylamino, di(lower alkyl)amino, lower alkanoylamino, lower alkoxycarbonylamino, nitro, carboxy, trifluoromethyl, halogen, tri(lower alkyl)silyl, aralkyl, and a cyclic ether residue. In the definitions of the substituents, the lower alkanoyl and the lower alkanoyl moiety of the lower alkanoylamino mean a straight-chain or branched alkanoyl group having 1 to 7 carbon atoms, such as formyl, acetyl, propionyl, butyryl, isobutyryl, valeryl, isovaleryl, pivaloyl, hexanoyl, and heptanoyl. The lower alkyl moiety of the lower alkoxycarbonyl, lower alkylamino, di(lower alkyl) amino, lower alkoxycarbonylamino, and tri(lower alkyl) silyl has the same meaning as the lower alkyl defined above, and the lower alkyl, lower alkoxy, halogen, cyclic ether residue, and aralkyl each has the same meaning as defined above.

The substituted methylene or ethylene has the same or different 1 to 3 substituents such as lower alkyl, and the lower alkyl has the same meaning as defined above.

Examples of the substituent on the nitrogen atom at position 1 of the substituted indolyl group are lower alkyl, lower alkanoyl, lower alkoxycarbonyl, lower alkylsulfonyl, aralkyl, substituted or unsubstituted aroyl, substituted or unsubstituted arylsulfonyl, substituted or unsubstituted heteroarylcarbonyl, substituted or unsubstituted heteroarylsulfonyl, diglycolyl, and

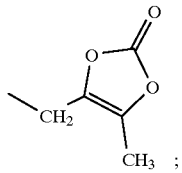

and examples of the substituents on the carbon atoms at positions 2 to 7 of the substituted indolyl group are lower alkyl, lower alkoxy, aralkyloxy, hydroxy, nitro, halogen, carboxy, lower alkanoyl, lower alkoxycarbonyl, aralkyl, trifluoromethyl, —NR⁶R⁷ (wherein R⁶ and R⁷ independently represent hydrogen, lower alkyl, lower alkanoyl, lower alkoxycarbonyl, or substituted or unsubstituted aroyl), substituted or unsubstituted aryl, and substituted or unsubstituted heteroaryl. In the definitions of the substituents, the heteroaryl moiety of the heteroarylcarbonyl and heteroarylsulfonyl has the same meaning as the heteroaryl defined above. The lower alkyl moiety of the lower alkylsulfonyl has the same meaning as the lower alkyl defined above, and the aryl moiety of the aroyl and arylsufonyl has the same meaning as the aryl defined above. The lower alkyl, lower alkanoyl, lower alkoxycarbonyl, aralkyl, lower alkoxy, aralkyloxy, halogen, aryl, and heteroaryl each has the same meaning as defined above.

The substituted aroyl, substituted arylsulfonyl, substituted heteroarylcarbonyl, substituted heteroarylsulfonyl, substituted heteroaryl, and substituted aryl each has the same or different 1 to 3 substituents such as lower alkyl, lower alkoxy, lower alkanoyl, lower alkoxycarbonyl, hydroxy, amino, lower alkylamino, di(lower alkyl)amino, lower alkanoylamino, lower alkoxycarbonylamino, nitro, carboxy, trifluoromethyl, and halogen. In the definitions of the substituents, the lower alkyl, lower alkoxy, lower alkanoyl, lower alkoxycarbonyl, lower alkylamino, di(lower alkyl) amino, lower alkanoylamino, lower alkoxycarbonylamino, and halogen each has the same meaning as defined above.

The pharmaceutically acceptable salts of Compounds (I) include inorganic acid addition salts such as hydrochloride, sulfate, and phosphate, organic acid addition salts such as acetate, maleate, fumarate, succinate, tartrate, citrate, oxalate, and methanesulfonate, alkali metal salts such as sodium salt and potassium salt, alkaline earth metal salts such as magnesium salt and calcium salt, metal salts such as aluminium salt and zinc salt, and ammonium salts such as ammonium and tetramethylammonium.

The present invention is described in detail below.

In the processes shown below, if the defined groups are converted into undesired groups under the conditions of the processes or are not suitable for carrying out the processes, the processes can be readily carried out by applying thereto means conventionally used in organic synthetic chemistry, for example, a means such as protection or deprotection of functional groups, or a method such as oxidation, reduction, or hydrolysis.

Process for Producing Compound (I)-1

Compound (I) can be prepared according to the following reaction step.

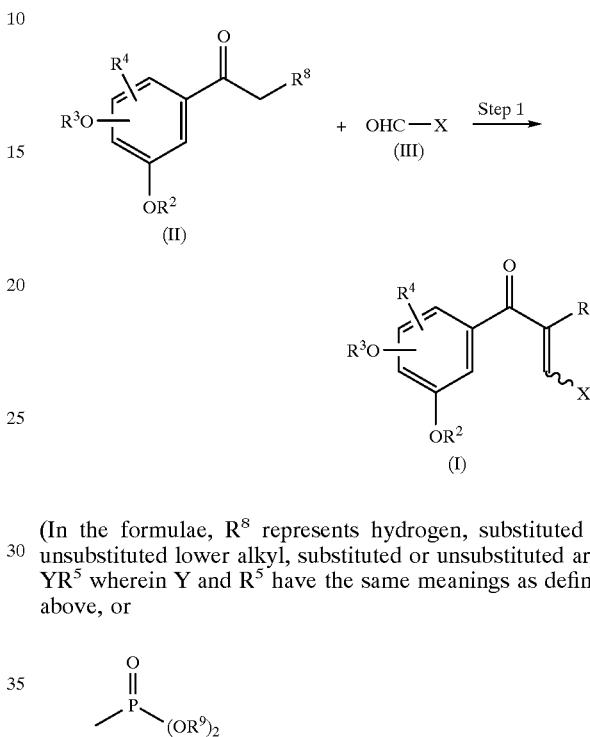

(In the formulae, R⁸ represents hydrogen, substituted or unsubstituted lower alkyl, substituted or unsubstituted aryl, YR⁵ wherein Y and R⁵ have the same meanings as defined above, or

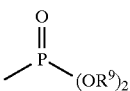

wherein R⁹ represents lower alkyl; and R¹, R², R³, R⁴, and X have the same meanings as defined above.)

In the definitions of R⁸ and R⁹, the lower alkyl, substituted or unsubstituted lower alkyl, and substituted or unsubstituted aryl each has the same meaning as defined above.

Step 1

Compound (I) can be obtained by reacting Compound (II) with Compound (III) in the presence of a base in an inert solvent. As the base, inorganic bases such as sodium hydroxide, potassium carbonate, sodium carbonate, and cesium fluoride, quaternary ammonium fluorides such as tetra-n-butylammonium fluoride, secondary amines such as piperidine, pyrrolidine, and morpholine, metal alkoxides such as sodium methoxide and potassium tert-butoxide, metal amides such as lithium diisopropylamide, metal hydrides such as sodium hydride, and the like may be used in an amount of 0.01 to 100 equivalents. As the solvent, aprotic solvents (for example, ethyl acetate, tetrahydrofuran, acetone, and N,N-dimethylformamide), aromatic hydrocarbons (for example, toluene), halogenated hydrocarbons (for example, chloroform), alcohols (for example, methanol and ethanol), water, and the like may be used alone or in combination. The reaction is carried out at the temperature between −78° C. and the boiling point of the solvent employed in the reaction, and is completed in 0.1 hour to 10 days.

The starting Compound (II) is commercially available, is reported in a literature, or can be prepared according to the following reaction steps.

Process for Producing Compound (II)-1

Compound (IIa), which is the starting Compound (II) in which $R^8$ is hydrogen, substituted or unsubstituted lower alkyl, substituted or unsubstituted aryl, or $YR^5$ wherein Y and $R^5$ have the same meanings as defined above, can be prepared according to the following reaction steps.

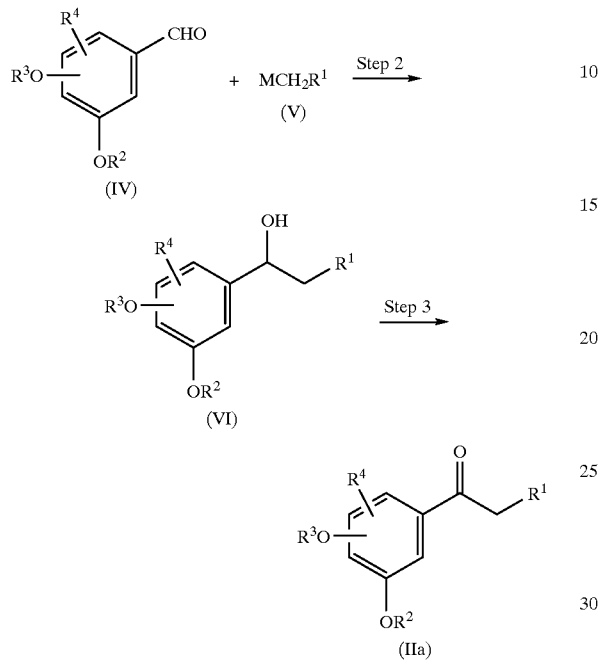

(In the formulae, M represents alkali metal, alkaline earth metal halide, or cerium dichloride; and $R^1$, $R^2$, $R^3$, and $R^4$ have the same meanings as defined above.)

In the definition of M, the alkali metal means lithium, sodium, potassium, cesium, or the like, and the alkaline earth metal halide means magnesium chloride, magnesium bromide, magnesium iodide, or the like.

Step 2

Compound (VI) can be obtained by reacting Compound (IV) with 1 to 2 equivalents of Compound (V) in an inert solvent. As the solvent, aprotic solvents (for example, diethyl ether, tetrahydrofuran, and ethyl acetate), aromatic hydrocarbons (for example, toluene), and the like may be used alone or in combination. The reaction is carried out at the temperature between −100° C. and the boiling point of the solvent employed in the reaction, and is completed in 0.1 to 24 hours.

Step 3

Compound (IIa) can be obtained by treating Compound (VI) with an oxidizing agent in an inert solvent. As the oxidizing agent, 1 to 50 equivalents of chromium trioxide, a pyridine complex or hydrochloric acid complex thereof, potassium dichromate, manganese dioxide, 2,3-dichloro-5,6-dicyanobenzoquinone, and the like may be used. As the solvent, aprotic solvents (for example, acetone and N,N-dimethylformamide), halogenated hydrocarbons (for example, dichloromethane and chloroform), acetic acid, sulfuric acid, water, and the like may be used alone or in combination. The reaction is carried out at the temperature between −10° C. and the boiling point of the solvent employed in the reaction, and is completed in 0.1 to 150 hours.

Process for Producing Compound (II)-2

Compound (IIb) which is the starting Compound (II) in which $R^8$ is

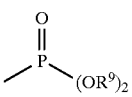

wherein $R^9$ has the same meaning as defined above can be prepared according to the following reaction steps.

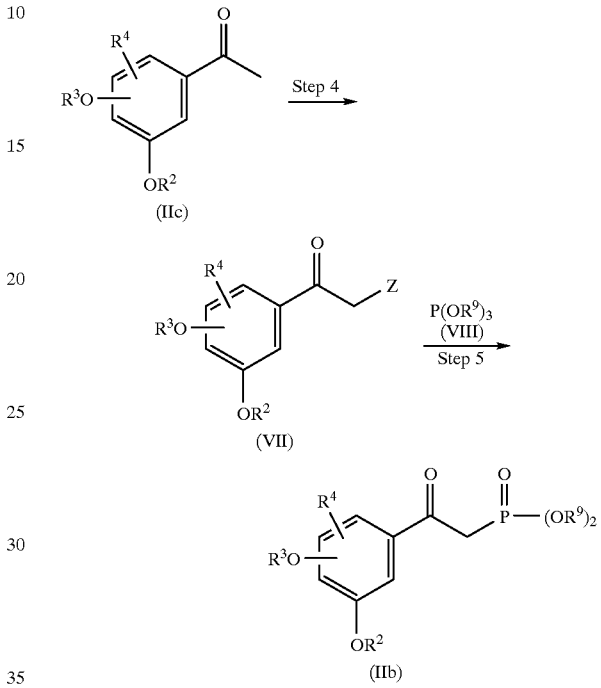

(In the formulae, Z represents halogen; and $R^2$, $R^3$, $R^4$, and $R^9$ have the same meanings as defined above.)

In the definition of Z, the halogen has the same meaning as defined above.

Step 4

Compound (VII) can be obtained by treating Compound (IIc) which is Compound (II) in which $R^8$ is hydrogen with a halogenating agent in an inert solvent. As the halogenating agent, 1 to 5 equivalents of pyrrolidone hydrotribromide, tetra-n-butylammonium tribromide, bromine, and the like may be used. As the solvent, aprotic solvents (for example, ethyl acetate and tetrahydrofuran), acetic acid, water, and the like may be used alone or in combination. The reaction is carried out at the temperature between 0° C. and the boiling point of the solvent employed in the reaction, and is completed in 0.1 to 24 hours.

Step 5

Compound (IIb) can be obtained by reacting compound (VII) with Compound (VIII) in an inert solvent or without a solvent. As the solvent, aprotic solvents (for example, ethyl acetate, tetrahydrofuran, and N,N-dimethylformamide), aromatic hydrocarbons (for example, toluene), halogenated hydrocarbons (for example, chloroform), and the like may be used alone or in combination. The reaction is carried out at the temperature between 50° C. and 250° C., and is completed in 0.1 hour to 7 days.

The starting Compound (III) is commercially available, is reported in a literature, or can be prepared according to the method described in The Chemistry of Heterocyclic Compounds, Indoles, 2 and 3 (1972, Jon Weary and Suns Incorporated) or the methods described in the literatures cited in the above The Chemistry of Heterocyclic Compounds, Indoles, 2 and 3, or the following reaction steps.

Process for Producing Compound (III)-1

Compound (IIIa) which is the starting Compound (III) in which X is substituted or unsubstituted indol-3-yl can be prepared according to the following reaction step.

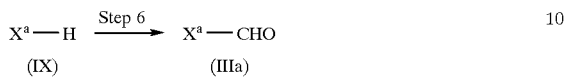

(In the formulae, $X^a$ represents substituted or unsubstituted indol-3-yl.)

In the definition of $X^a$, substituted indol-3-yl has the same meaning as defined above.

Step 6

Compound (IIIa) can be obtained by reacting Compound (IX) with a formylating agent in an inert solvent, and then, if necessary, treating the reaction product with a base. As the formylating agent, 1 to 10 equivalents of Vilsmeyer reagent prepared from N,N-dimethylformamide and phosphorus oxychloride and the like may be used. As the solvent, aprotic solvents (for example, tetrahydrofuran and N,N-dimethylformamide), aromatic hydrocarbons (for example, toluene), halogenated hydrocarbons (for example, chloroform), and the like may be used alone or in combination. As the base, 5 to 100 equivalents of an aqueous solution of sodium hydroxide and the like may be used. The reaction is carried out at the temperature between 0° C. and the boiling point of the solvent employed in the reaction, and is completed in 0.01 to 6 hours.

The starting Compound (IX) in Step 6 is commercially available, or can be prepared according to the method described in The Chemistry of Heterocyclic Compounds, Indoles, 2 and 3 (1972, Jon Weary and Suns Incorporated) or the methods described in the literatures cited in the above The Chemistry of Heterocyclic Compounds, Indoles, 2 and 3. 6-Trifluoromethylindole and 6-isopropylindole can be prepared according to the method described in Israel Journal of Chemistry (Israel J. Chem.), 4, 155 (1966) and Organic Synthesis (Org. Syn.), 63, 214 (1985), respectively. Compound (IXa) which is the starting Compound (IX) in which the substituent is 6-$R^{10}CH_2$ (In the formula, $R^{10}$ represents lower alkyl having 1 to 5 carbon atoms. In the definition of $R^{10}$, the lower alkyl having 1 to 5 carbon atoms has the same meaning as the lower alkyl having 1 to 5 carbon atoms within the definition of the lower alkyl defined above.) can be prepared according to the following reaction steps.

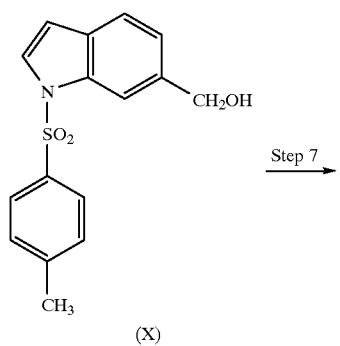

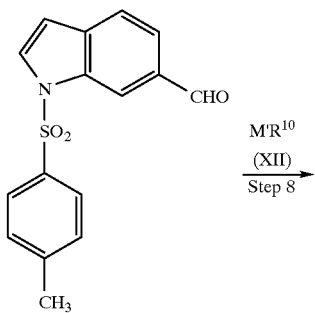

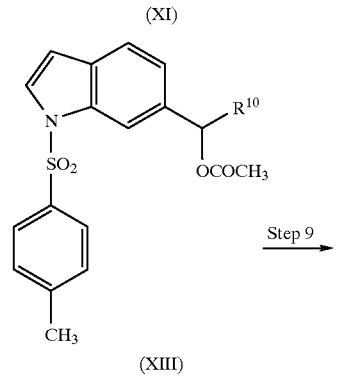

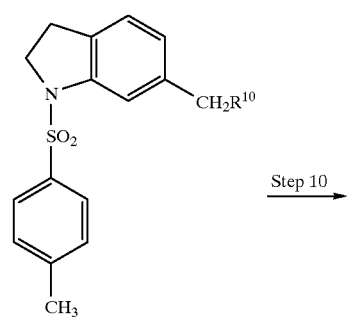

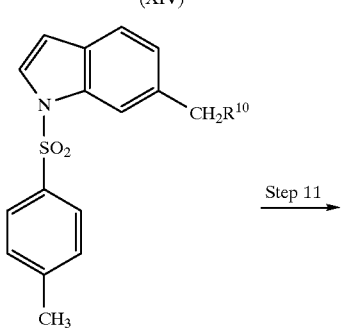

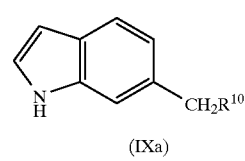

(In the formulae, M' represents alkali metal, alkaline earth metal halide, or cerium dichloride; and $R^{10}$ has the same meaning as defined above.)

In the definition of M', the alkali metal and alkali earth metal halide have the same meanings as defined above.

Step 7

Compound (XI) can be obtained by oxidizing, in the same manner as that in Step 3, 6-hydroxymethyl-1-toluenesulfonylindole [Compound (X)] obtained according to the method described in U.S. Pat. No. 4894386.

Step 8

Compound (XIII) can be obtained by reacting Compound (XI) with Compound (XII) in an inert solvent, and then treating the reaction mixture with acetic anhydride. As the solvent, aprotic solvents (for example, ethyl acetate and tetrahydrofuran), aromatic hydrocarbons (for example, toluene), and the like may be used alone or in combination. The reaction is carried out at the temperature between −100° C. and 30° C., and is completed in 0.1 to 5 hours.

Step 9

Compound (XIV) can be obtained by treating Compound (XIII) with a catalyst in an inert solvent under an atmosphere of hydrogen. As the catalyst, palladium, platinum, and the like may be used alone or held on activated carbon, barium sulfate, aluminum oxide, or the like in an amount of 1 to 500 weight % based on the amount of Compound (XIII). As the solvent, aprotic solvents (for example, ethyl acetate and tetrahydrofuran), aromatic hydrocarbons (for example, toluene), protic solvents (for example, methanol, ethanol, and acetic acid), and the like may be used alone or in combination. The reaction is carried out at the temperature between 10° C. to 120° C., and is completed in 1 to 50 hours.

Step 10

Compound (XV) can be obtained by treating Compound (XIV) with an oxidizing agent in an inert solvent. As the oxidizing agent, 1 to 500 equivalents of manganese dioxide, 2,3-dichloro-5,6-dicyanobenzoquinone, and the like may be used. As the solvent, aprotic solvents (for example, ethyl acetate and tetrahydrofuran), aromatic hydrocarbons (for example, toluene and chlorobenzene), protic solvents (for example, methanol, ethanol, and acetic acid), and the like may be used alone or in combination. The reaction is carried out at the temperature between 50° C. to 150° C., and is completed in 2 to 250 hours.

Step 11

Compound (IXa) can be obtained by treating Compound (XV) with a base in an inert solvent. As the base, 1 to 30 equivalents of lithium hydroxide, sodium hydroxide, potassium hydroxide, and the like may be used. As the solvent, aprotic solvents (for example, ether and tetrahydrofuran), protic solvents (for example, methanol and ethanol), water, and the like may be used alone or in combination. The reaction is carried out at the temperature between 10° C. to 120° C., and is completed in 5 to 100 hours.

Process for Producing Compound (III)-2

The compound which is the starting Compound (III) in which at least one substituent on the carbon atoms at positions 2 to 7 of the substituted indolyl group is —NR$^6$R$^7$ can alternatively be prepared according to the following reaction steps.

Step 12

Compound (IIIc) which is Compound (III) in which at least one substituent on the carbon atoms at positions 2 to 7 of the substituted indolyl group is dimethylamino can be obtained by treating Compound (IIIb) which is Compound (III) in which at least one substituent on the carbon atoms at positions 2 to 7 of the substituted indolyl group is nitro with 2 to 1000 equivalents of formalin and a catalyst in an inert solvent under an atmosphere of hydrogen. As the catalyst, palladium, platinum, and the like may be used alone or held on activated carbon, barium sulfate, or the like in an amount of 0.1 to 100 weight % based on the amount of Compound (IIIb). As the solvent, aprotic solvents (for example, tetrahydrofuran and N,N-dimethylformamide), aromatic hydrocarbons (for example, toluene), and the like may be used alone or in combination. The reaction is carried out at the temperature between 0° C. and the boiling point of the solvent employed in the reaction, and is completed in 0.1 hour to 7 days.

Step 13

Compound (IIId) which is Compound (III) in which at least one substituent on the carbon atoms at positions 2 to 7 of the substituted indolyl group is amino can be obtained by treating Compound (IIIb) with a reducing agent in an inert solvent. As the reducing agent, a sulfur compound (for example, sodium hydrosulfide and sodium bisulfite), a combination of hydrogen and a catalyst, and the like may be used. As the catalyst, palladium, platinum, and the like may be used alone or held on activated carbon, barium sulfate, or the like in an amount of 0.1 to 100 weight % based on the amount of Compound (IIIb). As the solvent, aprotic solvents (for example, tetrahydrofuran and N,N-dimethylformamide), protic solvents (for example, methanol and ethanol), aromatic hydrocarbons (for example, toluene), acetic acid, water, and the like may be used alone or in combination. The reaction is carried out at the temperature between 0° C. and the boiling point of the solvent employed in the reaction, and is completed in 0.1 hour to 7 days.

Step 14

Compound (IIIe) which is Compound (III) in which at least one substituent on the carbon atoms at positions 2 to 7 of the substituted indolyl group is —NHCOR$^{11\,a}$ (In the formula, R$^{11a}$ represents lower alkoxy. In the definition of R$^{11a}$, the lower alkoxy has the same meaning as defined above.) can be obtained by reacting Compound (IIId) with Compound (XVI) represented by the formula R$^{11a}$COZ$^1$ (In the formula, Z$^1$ represents halogen, and R$^{11a}$ represents the same as defined above. In the definition of Z$^1$, the halogen has the same meaning as defined above.) in the presence of a base in an inert solvent. As the base, 1 to 100 equivalents of tertiary amines (for example, pyridine, triethylamine, and diisopropylethylamine), inorganic bases (for example, sodium bicarbonate and potassium carbonate), metal hydrides (for example, sodium hydride), and the like may be used. As the solvent, aprotic solvents (for example, tetrahydrofuran and N,N-dimethylformamide), protic solvents (for example, methanol and ethanol), aromatic hydrocarbons (for example, toluene), halogenated hydrocarbons (for example, chloroform), water, and the like may be used alone or in combination. The reaction is carried out at the temperature between 0C and the boiling point of the solvent employed in the reaction, and is completed in 0.1 hour to 3 days.

Step 15

Compound (IIIf) which is Compound (III) in which at least one substituent on the carbon atoms at positions 2 to 7 of the substituted indolyl group is -NHCOR$^{11b}$ (In the formula, R$^{11b}$ represents hydrogen, lower alkyl, or substituted or unsubstituted aryl. In the definition of R$^{11b}$, the lower alkyl and substituted or unsubstituted aryl each has the same meaning as defined above.) can be obtained by reacting Compound (IIId) with Compound (XVII) represented by the formula R$^{11b}$CO$_2$ (In the formula, Z$^2$ represents halogen or R$^{11b}$CO$_2$ wherein R$^{11\,b}$ has the same meaning as defined above, and R$^{11b}$ represents the same as defined above. In the definition of Z$^2$, the halogen has the same meaning as defined above) according to the same method as that in Step 14.

Process for Producing Compound (III)-3

Compound (IIIh) which is the starting Compound (III) in which the substituent on the nitrogen atom at position 1 of the substituted indolyl group is a group other than diglycolyl can alternatively be prepared according to the following reaction step.

Step 16

Compound (IIIh) can be obtained by reacting Compound (IIIg), which is Compound (III) in which the hydrogen atom on the nitrogen atom at position 1 of the substituted or unsubstituted indolyl group is not substituted, with Compound (XVIII) represented by the formula $R^{12}$—$Z^3$ (In the formulae, $R^{12}$ represents a group other than diglycolyl in the definition of the substituent on the nitrogen atom at position 1 of the substituted indolyl group, and $Z^3$ represents halogen, p-nitrophenoxy, or $R^{12a}CO_2$ wherein $R^{12a}$ represents lower alkyl or aralkyl in the definition of $R^{12}$. In the definition of $Z^3$, the halogen has the same meaning as defined above.) according to the same method as that in Step 14.

Process for Producing Compound (III)-4

Compound (IIII) which is the starting Compound (III) in which the substituent on the nitrogen atom at position 1 of the substituted indolyl group is diglycolyl can alternatively be prepared according to the following reaction step.

Step 17

Compound (IIII) can be obtained according to the same method as that in Step 16, using diglycolic anhydride in place of Compound (XVIII).

The starting Compound (IV) is commercially available, is known in the literature, or can be prepared according to the following reaction steps from the aldehyde which is commercially available or known in the literature.

Process for Producing Compound (IV)-1

Compound (IVa) which is the starting Compound (IV) in which $R^2$ is lower alkyl or substituted or unsubstituted aralkyl can be prepared according to the following reaction step from the aldehyde which is commercially available or known in the literature.

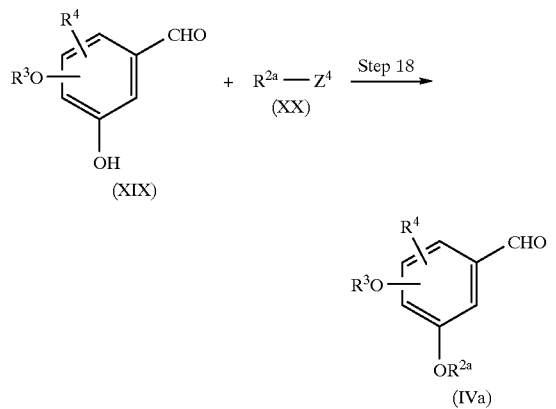

(In the formulae, $R^{2a}$ represents lower alkyl or substituted or unsubstituted aralkyl; $Z^4$ represents halogen; and $R^3$ and $R^4$ have the same meanings as defined above.)

In the definition of $R^{2a}$, the lower alkyl and substituted or unsubstituted aralkyl have the same meanings as defined above. In the definition of $Z^4$, the halogen has the same meaning as defined above.

Step 18

Compound (IVa) can be obtained by reacting Compound (XIX) with Compound (XX) in the presence of a base in an inert solvent. As the base, inorganic bases such as sodium hydroxide, potassium carbonate, sodium carbonate, and cesium fluoride, quaternary ammonium fluorides such as tetra-n-butylammonium fluoride, secondary amines such as piperidine, pyrrolidine, and morpholine, metal alkoxides such as sodium methoxide and potassium tert-butoxide, metal amides such as lithium diisopropylamide, metal hydrides such as sodium hydride, and the like may be used in an amount of 1 to 100 equivalents. As the solvent, aprotic solvents (for example, ethyl acetate, tetrahydrofuran, acetone, and N,N-dimethylformamide), aromatic hydrocarbons (for example, toluene), halogenated hydrocarbons (for example, chloroform), alcohols (for example, methanol and ethanol), water, and the like may be used alone or in combination. The reaction is carried out at the temperature between –78° C. and the boiling point of the solvent employed in the reaction, and is completed in 0.1 hour to 7 days.

Process for Producing Compound (IV)-2

Compound (IVb) which is the starting Compound (IV) in which $R^3$ is lower alkyl or substituted or unsubstituted aralkyl can be prepared according to the following reaction step from the aldehyde which is commercially available or known in the literature.

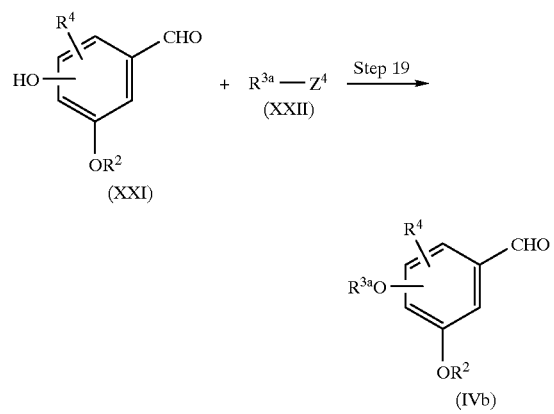

(In the formulae, $R^{3a}$ represents lower alkyl or substituted or unsubstituted aralkyl; and $R^2$, $R^4$, and $Z^4$ have the same meanings as defined above.)

In the definition of $R^{3a}$, the lower alkyl and substituted or unsubstituted aralkyl have the same meanings as defined above.

Step 19

Compound (IVb) can be obtained by reacting Compound (XXI) with Compound (XXII) according to the same method as that in Step 18.

Process for Producing Compound (IV)-3

Compound (IV) can be prepared according to the following reaction steps from the carboxylic acid or ester which is commercially available or known in the literature.

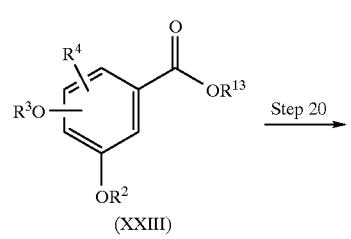

-continued

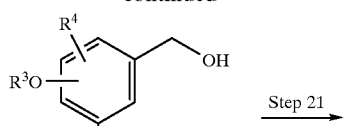
(XXIV)

Step 21 →

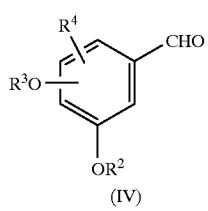
(IV)

(In the formulae, $R^{13}$ represents hydrogen, lower alkyl, or aralkyl; and $R^2$, $R^3$, and $R^4$ have the same meanings as defined above.)

In the definition of $R^{13}$, the lower alkyl and aralkyl have the same meanings as defined above.

Step 20

Compound (XXIV) can be obtained by treating Compound (XXIII) with a hydride reagent in an inert solvent. As the hydride reagent, 1 to 100 equivalents of sodium borohydride, lithium aluminum hydride, alane, borane, diisopropyl aluminium hydride, and the like may be used. As the solvent, aprotic solvents (for example, diethyl ether and tetrahydrofuran), aromatic hydrocarbons (for example, toluene), alcohols (for example, methanol and ethanol), and the like may be used alone or in combination. The reaction is carried out at the temperature between −78° C. and the boiling point of the solvent employed in the reaction, and is completed in 0.1 hour to 3 days.

Step 21

Compound (IV) can be obtained by treating Compound (XXIV) according to the same method as that in Step 3.

Process for Producing Compound (IIa)-3

Compound (IIa) can alternatively be prepared according to the following reaction step from the nitrile which is commercially available or known in the literature.

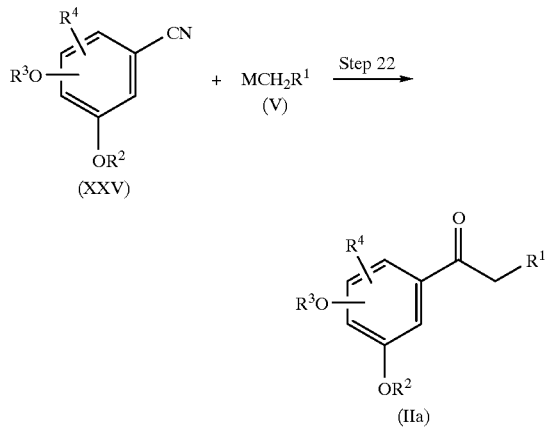
(IIa)

(In the formulae, $R^1$, $R^2$, $R^3$, $R^4$, and M have the same meanings as defined above.)

Step 22

Compound (IIa) can be obtained by reacting Compound (XXV) with Compound (V) according to the same method as that in Step 2.

Process for Producing Compound (II)-4

Compound (IIaa) which is Compound (IIa) in which $R^2$ is lower alkyl or substituted or unsubstituted aralkyl can alternatively be prepared according to the following reaction step from the ketone which is commercially available or known in the literature.

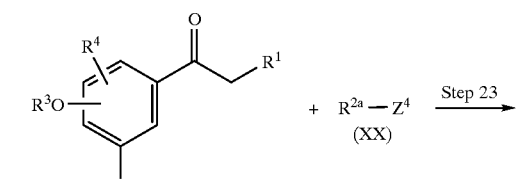

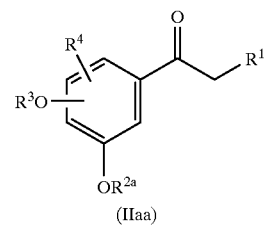
(IIaa)

(In the formulae, $R^1$, $R^2a$, $R^3$, $R^4$, and $Z^4$ have the same meanings as defined above.)

Step 23

Compound (IIaa) can be obtained by reacting Compound (XXVI) with Compound (XX) according to the same method as that in Step 18.

Process for Producing Compound (II)-5

Compound (IIab) which is Compound (IIa) in which $R^3$ is lower alkyl or substituted or unsubstituted aralkyl can alternatively be prepared according to the following reaction step from the ketone which is commercially available or known in the literature.

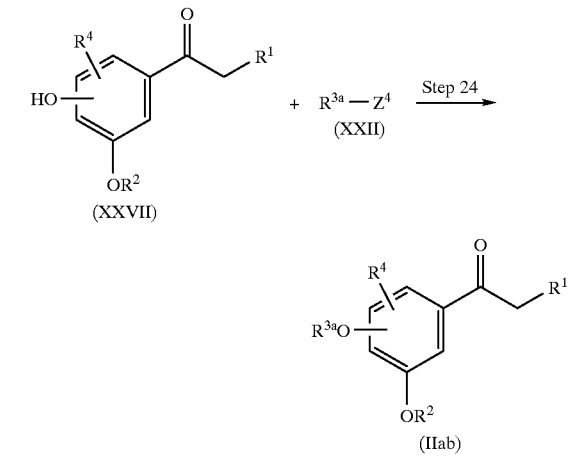

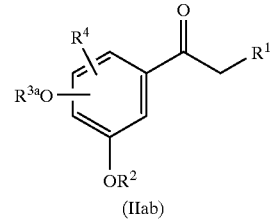
(IIab)

(In the formulae, $R^1$, $R^2$, $R^{3a}a$, $R^4$, and $Z^4$ have the same meanings as defined above.)

Step 24

Compound (IIab) can be obtained by reacting Compound (XXVII) with Compound (XXII) according to the same method as that in Step 18.

Process for Producing Compound (II)-6

Compound (IIac) which is Compound (IIa) in which $R^1$ is $YR^5$ can alternatively be prepared according to the following reaction step.

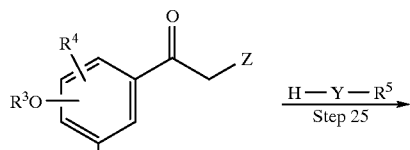

(VII)

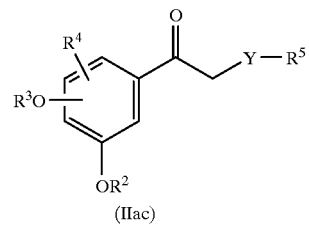

(IIac)

(In the formulae, $R^2$, $R^3$, $R^4$, $R^5$, Y, and Z have the same meanings as defined above.)

Step 25

Compound (IIac) can be obtained by reacting Compound (VII) with a compound represented by the formula H—Y—$R^5$ in the presence of a base in an inert solvent. As the base, inorganic bases such as potassium carbonate, sodium carbonate, cesium fluoride, and sodium hydroxide, quaternary ammonium fluorides such as tetra-n-butylammonium fluoride, secondary amines such as piperidine, pyrrolidine, and morpholine, metal alkoxides such as sodium methoxide and potassium tert-butoxide, metal amides such as lithium diisopropylamide, metal hydrides such as sodium hydride, and the like may be used in an amount of 1 to 10 equivalents. As the solvent, aprotic solvents (for example, ethyl acetate, tetrahydrofuran, and dimethyl sulfoxide), aromatic hydrocarbons (for example, toluene), halogenated hydrocarbons (for example, chloroform), and the like may be used alone or in combination. The reaction is carried out at the temperature between −78° C. and the boiling point of the solvent employed in the reaction, and is completed in 0.1 hour to one day.

Process for Producing Compound (II)-7

Compound (IIaf) which is Compound (IIa) having a 1,2-dihydroxyethyl group as a substituent of $R^1$ can alternatively be prepared according to the following reaction steps from Compound (IIad) having a vinyl group as a substituent of $R^1$.

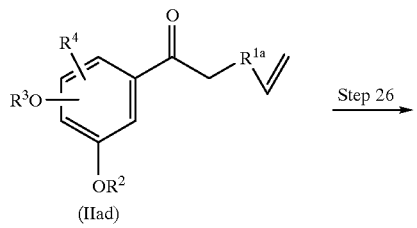

(IIad)

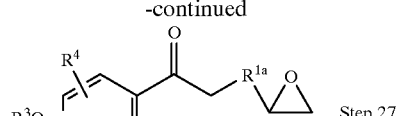

(IIae)

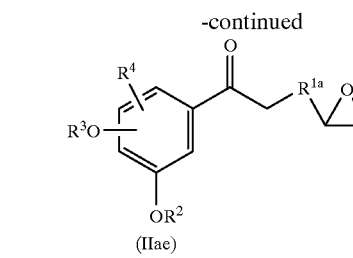

(IIaf)

[In the formulae, $R^{1a}$ represents substituted lower alkyl or $YR^{5a}$ (wherein $R^{5a}$ represents substituted or unsubstituted lower alkyl, substituted or unsubstituted aryl, substituted or unsubstituted heteroaryl, or a substituted or unsubstituted cyclic ether residue; and Y has the same meaning as defined above); and $R^2$, $R^3$, and $R^4$ have the same meanings as defined above.]

In the definition of $R^{1a}$, the substituted lower alkyl has the same meaning as defined above. In the definition of $R^{5a}$, the substituted or unsubstituted lower alkyl, substituted or unsubstituted aryl, substituted or unsubstituted heteroaryl, and substituted or unsubstituted cyclic ether residue each has the same meaning as defined above.

Step 26

Compound (IIae) which is Compound (IIa) having an oxiranyl group as a substituent of $R^1$ can be obtained by treating Compound (IIad) with an oxidizing agent, if necessary, in the presence of a catalyst or a base, in an inert solvent. As the oxidizing agent, 1 to 10 equivalents of m-chloroperbenzoic acid, tert-butyl hydroperoxide, hydrogen peroxide, and the like may be used. As the catalyst, 0.01 to 10 equivalents of vanadium acetylacetonate, titanium tetraisopropoxide, and the like may be used. As the base, 1 to 10 equivalents of sodium bicarbonate, potassium carbonate, sodium acetate, and the like may be used. As the solvent, aprotic solvents (for example, ethyl acetate and tetrahydrofuran), protic solvents (for example, methanol), halogenated hydrocarbons (for example, chloroform), acetic acid, water, and the like may be used alone or in combination. The reaction is carried out at the temperature between −30° C. and the boiling point of the solvent employed in the reaction, and is completed in 0.1 to 72 hours.

Step 27

Compound (IIaf) can be obtained by treating Compound (IIae) with a salt of a carboxylic acid or a base in an inert solvent. As the salt of a carboxylic acid, 1 to 100 equivalents of sodium acetate, potassium benzoate, and the like may be used. As the base, 1 to 100 equivalents of sodium bicarbonate, potassium carbonate, sodium acetate, and the like may be used. As the solvent, aprotic solvents (for example, N,N-dimethylformamide, pyridine, and tetrahydrofuran), protic solvents (for example, methanol), water, and the like may be used alone or in combination. The reaction is carried out at the temperature between 0C and the boiling point of the solvent employed in the reaction, and is completed in 0.1 to 72 hours.

Process for Producing Compound (II)-8

Compound (IIac) can alternatively be prepared according to the following reaction steps from Compound (IV) or Compound (VII).

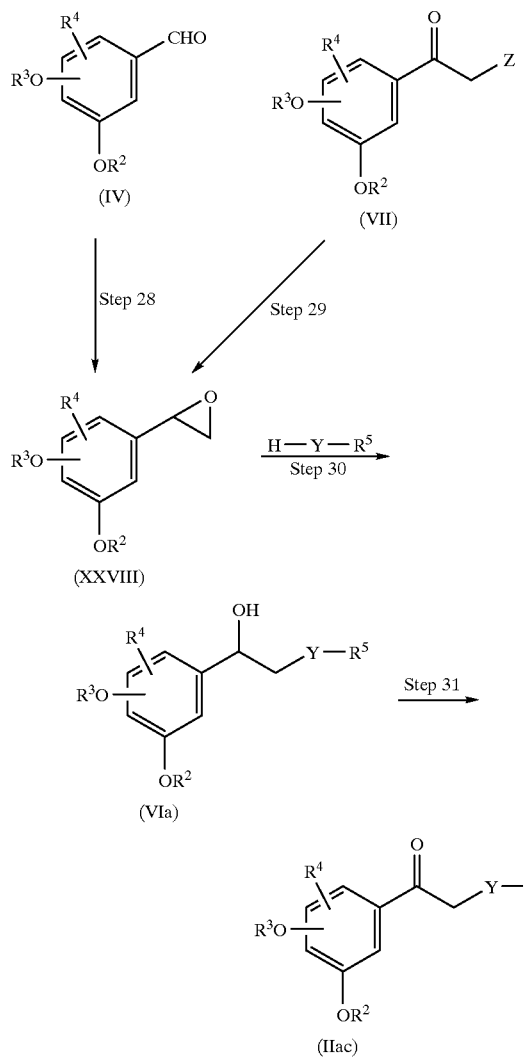

(In the formulae, $R^2$, $R^3$, $R^4$, $R^5$, Y, and Z have the same meanings as defined above.)

Step 28

Compound (XXVIII) can be obtained by reacting Compound (IV) with trimethylsulfoxonium iodide according to the same method as that in Step 25.

Step 29

Compound (XXVIII) can be obtained by treating Compound (VII) according to the same method as that in Step 20 or by adding a base thereafter and reacting the resulting mixture in an inert solvent at the temperature between 0° C. and the boiling point of the solvent employed in the reaction for 1 to 24 hours. As the base, 1 to 10 equivalents of sodium bicarbonate, potassium carbonate, sodium acetate, and the like may be used. As the solvent, aprotic solvents (for example, diethyl ether and tetrahydrofuran), aromatic hydrocarbons (for example, toluene), alcohols (for example, methanol and ethanol), water, and the like may be used alone or in combination.

Step 30

Compound (VIa) which is Compound (VI) in which $R^1$ is $YR^5$ can be obtained by reacting Compound (XXVIII) with Compound H—Y—$R^5$ according to the same method as that in Step 25.

Step 31

Compound (IIac) can be obtained by treating Compound (VIa) according to the same method as that in Step 21.

Process for Producing Compound (I)-2

Compound (Ia) which is Compound (I) in which $R^1$ is substituted or unsubstituted lower alkyl, substituted or unsubstituted aryl, or $YR^5$ can alternatively be prepared according to the following reaction steps.

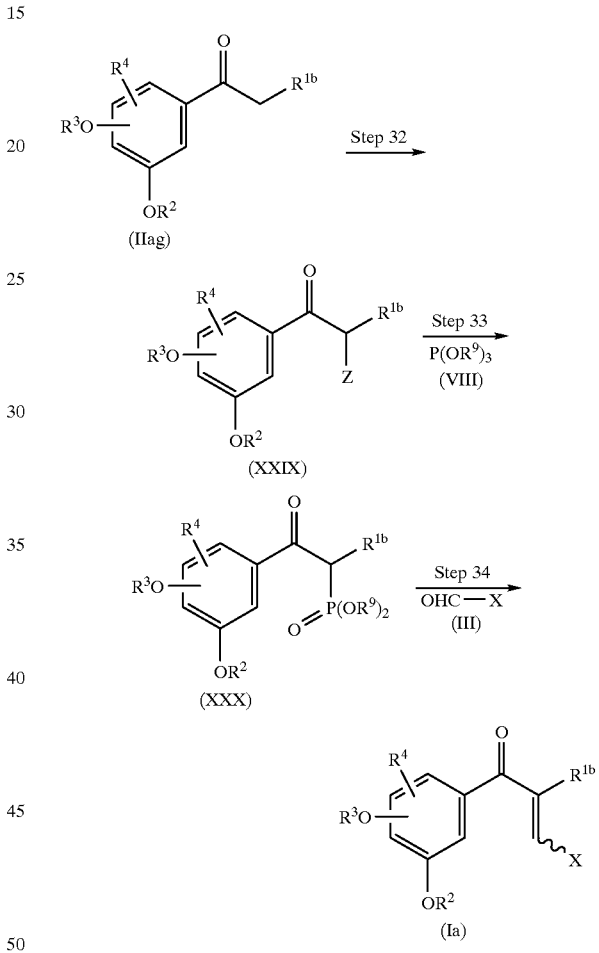

[In the formulae, $R^{1b}$ represents substituted or unsubstituted lower alkyl, substituted or unsubstituted aryl, or $YR^5$ (wherein Y and $R^5$ have the same meanings as defined above); and $R^2$, $R^3$, $R^4$, $R^9$, X, and Z have the same meanings as defined above.]

In the definition of $R^{1b}$, the substituted or unsubstituted lower alkyl, and substituted or unsubstituted aryl have the same meanings as defined above.

Step 32

Compound (XXIX) can be obtained by treating Compound (IIag) which is Compound (IIa) in which $R^1$ is substituted or unsubstituted lower alkyl, substituted or unsubstituted aryl, or $YR^5$ with a halogenating agent in an inert solvent. As the halogenating agent, 1 to 5 equivalents of pyrrolidone hydrotribromide, tetra-n-butylammonium tribromide, bromine, and the like may be used. As the solvent, aprotic solvents (for example, ethyl acetate and tetrahydrofuran), acetic acid, water, and the like may be used alone or in combination. The reaction is carried out at the temperature between 0° C. and the boiling point of the solvent employed in the reaction, and is completed in 0.1 to 24 hours.

Step 33

Compound (XXX) can be obtained by reacting Compound (XXIX) with 1 to 10 eqivalents of Compound (VIII) in an inert solvent or without a solvent. As the solvent, aprotic solvents (for example, ethyl acetate, tetrahydrofuran, and N,N-dimethylformamide), aromatic hydrocarbons (for example, toluene and benzene), protic solvents (for example, methanol), and the like may be used alone or in combination. The reaction is carried out at the temperature between 0° C. and 200° C., and is completed in 0.5 to 100 hours.

Step 34

Compound (Ia) can be obtained by reacting Compound (XXX) with Compound (III) according to the same method as that in Step 1.

Process for Producing Compound (I)-3

Compound (Ic) which is Compound (I) in which the substituent on the nitrogen atom at position 1 of the substituted indolyl group is a group other than diglycolyl can alternatively be prepared according to the following reaction step.

Step 35

Compound (Ic) can be obtained by reacting Compound (Ib), which is Compound (I) in which the hydrogen atom on the nitrogen atom at position 1 of the substituted or unsubstituted indolyl group is not substituted, with Compound (XVIII) according to the same method as that in Step 16.

Process for Producing Compound (I)-4

Compound (Id) which is Compound (I) in which the substituent on the nitrogen atom at position 1 of the substituted indolyl group is diglycolyl can alternatively be prepared according to the following reaction step.

Step 36

Compound (Id) can be obtained according to the same method in Step 35, using diglycolic anhydride in place of Compound (XVIII).

Some Compounds (I) thus obtained can also be used as an intermediate to prepare novel derivatives (I) by subjecting them to oxidation, reduction, alkylation, acylation, or the like.

HS—$R^5$ which is the starting compound H—Y—$R^5$ in which Y is S is commercially available, is reported in a literature, or can be prepared according to the following reaction steps.

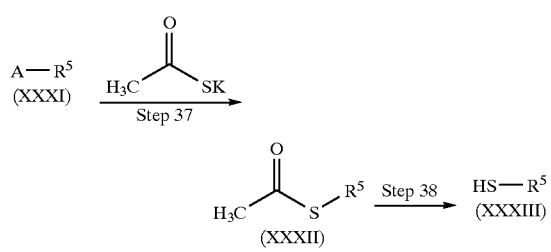

(In the formulae, A represents halogen, trifluoromethanesulfonyloxy, methanesulfonyloxy, benzenesulfonyloxy, or toluenesulfonyloxy; and $R^5$ has the same meaning as defined above.)

In the definition of A, the halogen has the same meaning as defined above.

Step 37

Compound (XXXII) can be obtained by reacting Compound (XXXI) with 1 to 50 equivalents of potassium thioacetate in an inert solvent. As the solvent, aprotic solvents (for example, N,N-dimethylformamide, N-methylpyrrolidone, dimethyl sulfoxide, pyridine, and tetrahydrofuran), protic solvents (for example, methanol), water, and the like may be used alone or in combination. The reaction is carried out at the temperature between 0° C. and the boiling point of the solvent employed in the reaction, and is completed in 0.1 to 72 hours.

Step 38

Compound (XXXIII) can be obtained by treating Compound (XXXII) with a base in an inert solvent or without a solvent. As the base, inorganic bases such as sodium bicarbonate, potassium carbonate, sodium acetate, and sodium hydroxide, amines such as piperidine, pyrrolidine, and morpholine, and the like may be used in an amount of 1 to 100 equivalents. As the solvent, aprotic solvents (for example, N,N-dimethylformamide, pyridine, and tetrahydrofuran), protic solvents (for example, methanol), water, and the like may be used alone or in combination. The reaction is carried out at the temperature between 0° C. and the boiling point of the solvent employed in the reaction, and is completed in 0.1 to 72 hours.

The intermediates and the desired compounds in the processes described above can be isolated and purified by purification methods conventionally used in organic synthetic chemistry, for example, filtration, extraction, washing, drying, concentration, recrystallization, and various kinds of chromatography. The intermediates may also be subjected to the subsequent reaction without isolation.

In the case where a salt of Compound (I) is desired and it is produced in the form of the desired salt, it can be subjected to purification as such. In the case where Compound (I) is produced in the free form and its salt is desired, Compound (I) is dissolved or suspended in a suitable solvent, followed by addition of an acid or a base to form a salt by a conventional method.

Compounds (I) can exist in the form of E/Z geometrical isomers, and the present invention covers all isomers including these geometrical isomers and mixtures thereof. In the case where Compound (I) is obtained in a E/Z mixture, and separation of E/Z isomers is desired, they can be isolated and purified by fractionation methods, for example, fractional crystallization, fractional precipitation, fractional dissolution, or the like.

Compounds (I) and pharmaceutically acceptable salts thereof may be in the form of adducts with water or various solvents, which are also within the scope of the present invention.

Examples of Compounds (I) obtained in the processes described above are shown in Table 1.

TABLE 1-1

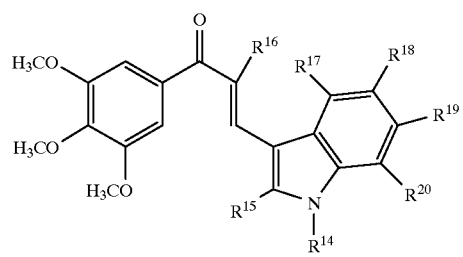

| Compd. No. | $R^{14}$ | $R^{15}$ | $R^{16}$ | $R^{17}$ | $R^{18}$ | $R^{19}$ | $R^{20}$ |
|---|---|---|---|---|---|---|---|
| 1 | H | H | H | H | H | H | H |
| 2 | $CH_3$ | H | H | H | H | H | H |
| 3 | $CH_3CH_2$ | H | H | H | H | H | H |
| 4 | $CH_3(CH_2)_3$ | H | H | H | H | H | H |
| 5 | $(CH_3)_2CHCH_2$ | H | H | H | H | H | H |
| 6 | $CH_3CO$ | H | H | H | H | H | H |
| 7 | $CH_3CH_2CO_2$ | H | H | H | H | H | H |
| 8 | $C_6H_5CO$ | H | H | H | H | H | H |
| 9 | $CH_3SO_2$ | H | H | H | H | H | H |
| 10 | $C_6H_5SO_2$ | H | H | H | H | H | H |
| 11 | DMDO[a] | H | H | H | H | H | H |
| 12 | H | $CH_3$ | H | H | H | H | H |
| 13 | $CH_3$ | Cl | H | H | H | H | H |
| 14 | H | $4-ClC_6H_4$ | H | H | H | H | H |
| 15 | H | H | H | $CH_3$ | H | H | H |
| 16 | $CH_3$ | H | H | $CH_3$ | H | H | H |
| 17 | H | H | H | $NO_2$ | H | H | H |
| 18 | H | H | H | $CH_3O$ | H | H | H |
| 19 | H | H | H | $CH_3O$ | H | H | $CH_3O$ |
| 20 | H | H | H | H | $CH_3$ | H | H |
| 21 | H | H | H | H | $NO_2$ | H | H |
| 22 | $CH_3$ | H | H | H | $(CH_3)_2N$ | H | H |
| 23 | $CH_3$ | H | H | H | $CH_3CH_2CO_2NH$ | H | H |
| 24 | $CH_3$ | H | H | H | $CH_3CONH$ | H | H |
| 25 | H | H | H | H | $CH_3O$ | H | H |

[a]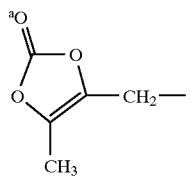

TABLE 1-2

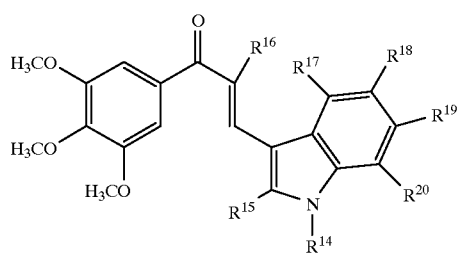

| Compd. No. | $R^{14}$ | $R^{15}$ | $R^{16}$ | $R^{17}$ | $R^{18}$ | $R^{19}$ | $R^{20}$ |
|---|---|---|---|---|---|---|---|
| 26 | H | H | H | H | $CH_3O$ | $CH_3O$ | H |
| 27 | H | H | H | H | OH | $CH_3O$ | H |
| 28 | H | H | H | H | $C_6H_5CH_2O$ | H | H |
| 29 | H | H | H | H | F | H | H |
| 30 | H | H | H | H | Cl | H | H |
| 31 | H | H | H | H | Br | H | H |
| 32 | H | H | H | H | H | $CH_3$ | H |
| 33 | H | H | H | H | H | $CF_3$ | H |
| 34 | H | H | H | H | H | $NO_2$ | H |

TABLE 1-2-continued

| Compd. No. | $R^{14}$ | $R^{15}$ | $R^{16}$ | $R^{17}$ | $R^{18}$ | $R^{19}$ | $R^{20}$ |
|---|---|---|---|---|---|---|---|
| 35 | $CH_3$ | H | H | H | H | $(CH_3)_2N$ | H |
| 36 | $CH_3$ | H | H | H | H | $CH_3CH_2CO_2NH$ | H |
| 37 | H | H | H | H | H | $CH_3CONH$ | H |
| 38 | $CH_3$ | H | H | H | H | $CH_3CONH$ | H |
| 39 | H | H | H | H | H | $CH_3O$ | H |
| 40 | H | H | H | H | H | $CH_3O$ | $CH_3O$ |
| 41 | H | H | H | H | H | OH | $CH_3O$ |
| 42 | H | H | H | H | H | Cl | H |
| 43 | H | H | H | H | H | H | $CH_3$ |
| 44 | H | H | H | H | H | H | $NO_2$ |
| 45 | $CH_3$ | H | H | H | H | H | $NO_2$ |
| 46 | H | H | H | H | H | H | $CH_3O$ |
| 47 | $C_6H_5CH_2$ | H | H | H | H | H | H |
| 48 | H | H | $CH_3$ | H | H | H | H |
| 49 | H | H | $CH_3(CH_2)_2$ | H | H | H | H |

TABLE 1-3

| Compd. No. | $R^{14}$ | $R^{15}$ | $R^{16}$ | $R^{17}$ | $R^{18}$ | $R^{19}$ | $R^{20}$ |
|---|---|---|---|---|---|---|---|
| 50 | $4\text{-}CH_3C_6H_4CO$ | H | H | H | H | H | H |
| 51 | $4\text{-}CH_3OC_6H_4CO$ | H | H | H | H | H | H |
| 52 | $3\text{-}CH_3C_6H_4CO$ | H | H | H | H | H | H |
| 53 | $3\text{-}CH_3OC_6H_4CO$ | H | H | H | H | H | H |
| 54 | $2\text{-}CH_3C_6H_4CO$ | H | H | H | H | H | H |
| 55 | $2\text{-}CH_3OC_6H_4CO$ | H | H | H | H | H | H |
| 56 | $4\text{-}CH_3CONHC_6H_4CO$ | H | H | H | H | H | H |
| 57 | $4\text{-}(CH_3)_2NC_6H_4CO$ | H | H | H | H | H | H |
| 58 | $3,4\text{-}(CH_3O)_2C_6H_3CO$ | H | H | H | H | H | H |
| 59 | $3,4,5\text{-}(CH_3O)_3C_6H_2CO$ | H | H | H | H | H | H |
| 60 | nicotinoyl | H | H | H | H | H | H |
| 61 | isonicotinoyl | H | H | H | H | H | H |
| 62 | H | H | $CH_3CH_2$ | H | H | H | H |
| 63 | H | H | $CH_3$ | H | H | $CH_3$ | H |
| 64* | H | H | $C_6H_5$ | H | H | H | H |
| 65 | H | H | $CH_3(CH_2)_3$ | H | H | H | H |
| 66 | H | H | $CH_3$ | H | H | $CH_3CH_2$ | H |
| 67 | $HO_2CCH_2OCH_2CO$ | H | H | H | H | H | H |
| 68 | H | H | H | H | H | $(CH_3)_2CH$ | H |

*: mixture of E-form and Z-form

TABLE 1-4

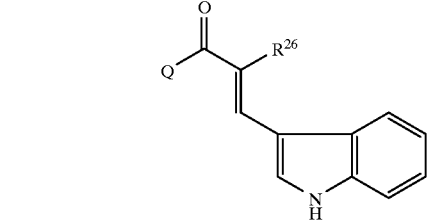

| Compd. No. | $R^{24}$ | $R^{23}$ | $OR^{22}$ | $R^{21}$ | $R^{25}$ |
|---|---|---|---|---|---|
| 69 | $OCH_3$ | H | $OCH_3$ | H | H |
| 70 | $OCH_3$ | OH | $OCH_3$ | H | H |
| 71 | $OCH_3$ | $OCH_2C_6H_5$ | $OCH_3$ | H | H |
| 72 | $OCH_2CH_3$ | $OCH_2CH_3$ | $OCH_2CH_3$ | $CH_3$ | H |
| 73 | $OCH_3$ | $OCH_2CH_3$ | $OCH_3$ | $CH_3$ | H |
| 74 | $OCH_3$ | $OCH_2CH(CH_3)_2$ | $OCH_3$ | $CH_3$ | H |
| 75 | $OCH_3$ | $CH_2CH_3$ | $OCH_3$ | $CH_3$ | H |
| 76 | $OCH_3$ | —$OCH_2O$— | | $CH_3$ | H |
| 77 | $OCH_2CH_3$ | $OCH_3$ | $OCH_3$ | $CH_3$ | H |
| 78 | Br | $OCH_3$ | $OCH_3$ | $CH_3$ | H |
| 79 | $OCH_3$ | $OCH_2CH_3$ | $OCH_3$ | $CH_3$ | $CH_3$ |
| 80 | $OCH_3$ | —$OCH_2O$— | | $CH_3$ | $CH_3$ |
| 81 | Br | $OCH_2CH(CH_3)_2$ | $OCH_3$ | $CH_3$ | H |
| 82 | Br | $OCH_2CH(CH_3)_2$ | $OCH_3$ | $CH_3$ | $CH_3$ |
| 83 | $OCH_3$ | $OCH_2CH(CH_3)_2$ | $OCH_3$ | $CH_3$ | $CH_3$ |
| 84 | $OCH_3$ | $OCH_2CH_3$ | $OCH_3$ | $CH_3$ | $CH_2CH_3$ |
| 85 | $OCH_3$ | $OCH_2CH_3$ | $OCH_3$ | $CH_3$ | $CH(CH_3)_2$ |
| 86 | $OCH_3$ | $OCH_2CH_3$ | $OCH_3$ | $CH_3$ | Cl |
| 87 | $OCH_3$ | $OCH_2CH_2CH_3$ | $OCH_3$ | $CH_3$ | $CH_3$ |
| 88 | $OCH_3$ | $O(CH_2)_3CH_3$ | $OCH_3$ | $CH_3$ | $CH_3$ |

TABLE 1-5

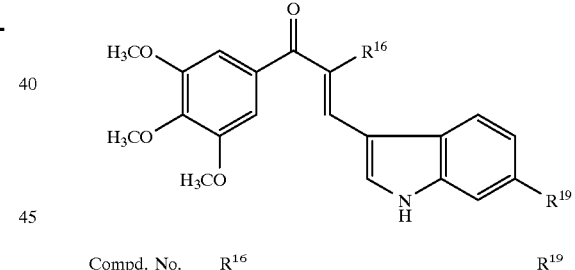

| Compd. No. | Q | $R^{26}$ |
|---|---|---|
| 89 | 2,4-dimethoxyphenyl (OCH₃ at 1,4; CH₃ at 2) | H |
| 90 | 2,4-dimethoxyphenyl (OCH₃ at 1,4; CH₃ at 2) | $CH_3$ |

TABLE 1-5-continued

| Compd. No. | Q | $R^{26}$ |
|---|---|---|
| 91 | 2,4,5-trimethoxyphenyl with methyl | $CH_3$ |
| 92 | 2,3,4-trimethoxyphenyl with methyl | $CH_3$ |

TABLE 1-6

| Compd. No. | $R^{16}$ | $R^{19}$ |
|---|---|---|
| 93 | $OCH_3$ | H |
| 94 | $OCH_2CH_3$ | H |
| 95 | $O(CH_2)_2CH_3$ | H |
| 96 | $OCH(CH_3)_2$ | H |
| 97 | $O(CH_2)_2Si(CH_3)_3$ | H |
| 98 | $O(CH_2)_3Si(CH_3)_3$ | H |
| 99 | O-(2-methylphenyl) | H |
| 100 | O-(4-bromophenyl) | H |
| 101 | $SCH_3$ | H |
| 102 | $S(CH_2)_2Si(CH_3)_3$ | H |

TABLE 1-6-continued

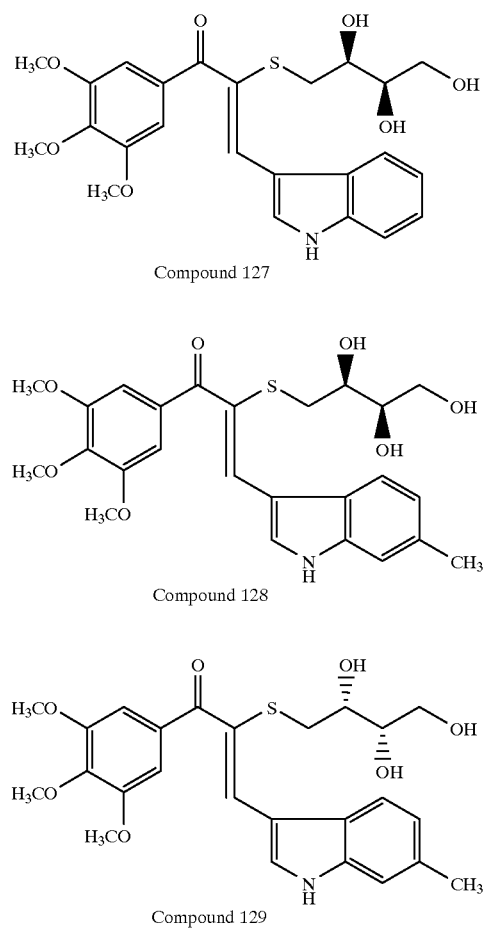

| Compd. No. | R¹⁶ | R¹⁹ |
|---|---|---|
| 103 | (4-fluorophenylthio) | H |
| 104 | S(CH₂)₂OH | H |
| 105 | S(CH₂)₂OH | CH₃ |
| 106 | (thio-sugar) | CH₃ |
| 107 | SCH₂CO₂H | H |
| 108 | SCH₂CO₂CH₃ | H |
| 109 | S(CH₂)₂N(CH₂CH₃)₂ | H |
| 110 | S(CH₂)₄OC₆H₅ | H |
| 111 | (CH₂)₂CH(OH)CH₂OH | H |
| 112 | (CH₂)₂CH(OH)CH₂OH | CH₃ |

TABLE 1-7

| Compd. No. | R¹⁴ | R¹⁷ | R¹⁸ | R¹⁹ |
|---|---|---|---|---|
| 113 | H | H | H | H |
| 114 | CH₃ | H | H | H |
| 115 | H | CH₃ | H | H |
| 116 | H | Cl | H | H |
| 117 | H | H | CH₃ | H |
| 118 | H | H | Cl | H |
| 119 | H | H | F | H |
| 120 | H | H | H | CH₃ |
| 121 | H | H | H | CH₂CH₃ |
| 122 | H | H | H | CH(CH₃)₂ |
| 123 | H | H | H | Cl |
| 124 | H | H | H | F |
| 125 | H | H | H | NHCOCH₃ |
| 126 | CH₃ | H | H | NHCOCH₃ |

TABLE 1-8

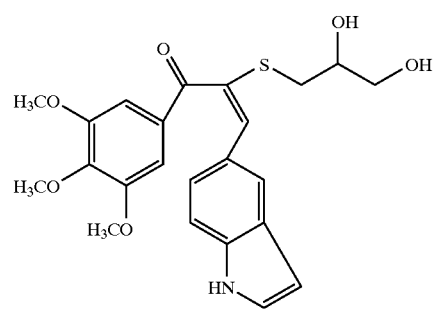

Compound 127

Compound 128

Compound 129

Compound 130a

Compound 130b

The pharmacological activities of Compounds (I) are shown in detail below by test examples.

TEST EXAMPLE 1

HeLa $S_3$ Cell Growth Inhibition Test

Each 0.1 ml of HeLa $S_3$ cells which had been prepared to $3 \times 10^4$ cells/ml using a medium consisted of MEM medium, 10% fetal bovine serum and 2 mM glutamine was distributed in each well of 96 well-microtiter plate. HeLa $S_3$ was cultured at 37° C. for one night in a $CO_2$ incubator, each 0.05 ml of test compounds which had been appropriately diluted with the culture solution was added thereto, and the mixture was cultured at 37° C. for 72 hours in a $CO_2$ incubator. Supernatant was removed, each 0.1 ml of the culture solution containing 0.02% neutral red was added to the residue, the mixture was incubated at 37° C. for one hour in a $CO_2$ incubator, and the cells were stained. Supernatant was removed and the residue was washed once with physiological saline. Then, the pigment was extracted with 0.001 N hydrochloric acid/30% ethanol and the absorbance at 550 nm was measured by a microplatereader. A concentration of the test compound ($IC_{50}$) at which the growth of cell is inhibited by 50% was calculated by comparing the absorbance of non-treated cells and that of cells treated with a predetermined concentration of the test compound.

The results are shown in Table 2.

TABLE 2

| Compd. No. | $IC_{50}$ (72 h, $\mu$M) | Compd. No. | $IC_{50}$ (72 h, $\mu$M) |
|---|---|---|---|
| 1 | 0.010 | 75 | 0.064 |
| 2 | 0.020 | 76 | 0.0061 |
| 3 | 0.058 | 77 | 0.0032 |
| 6 | 0.017 | 78 | 0.0066 |
| 8 | 0.026 | 79 | 0.0067 |
| 12 | 0.26 | 80 | 0.0023 |
| 13 | 0.078 | 83 | 0.018 |
| 15 | 0.086 | 84 | 0.0062 |
| 20 | 0.11 | 86 | 0.0063 |
| 29 | 0.060 | 87 | 0.0052 |
| 32 | 0.0063 | 88 | 0.0061 |
| 38 | 0.055 | 92 | 0.022 |
| 40 | 0.012 | 93 | 0.0024 |
| 46 | 0.20 | 94 | 0.0025 |
| 48 | 0.00029 | 95 | 0.013 |
| 49 | 0.0060 | 96 | 0.0037 |
| 50 | 0.025 | 99 | 0.068 |
| 51 | 0.023 | 100 | 0.062 |
| 52 | 0.058 | 101 | 0.0022 |
| 53 | 0.034 | 105 | 0.0025 |
| 56 | 0.023 | 108 | 0.0047 |
| 57 | 0.031 | 111 | 0.0021 |
| 58 | 0.064 | 112 | 0.0056 |
| 59 | 0.028 | 113 | 0.0048 |
| 60 | 0.0077 | 114 | 0.020 |
| 61 | 0.0097 | 115 | 0.019 |
| 62 | 0.0047 | 116 | 0.015 |
| 63 | 0.00073 | 119 | 0.0063 |
| 64 | 0.0023 | 120 | 0.0063 |
| 65 | 0.0063 | 121 | 0.018 |
| 66 | 0.0025 | 123 | 0.0072 |
| 67 | 0.011 | 124 | 0.0059 |
| 72 | 0.022 | 127 | 0.0044 |
| 73 | 0.0025 | 128 | 0.0053 |
| 74 | 0.0094 | 129 | 0.0071 |

TEST EXAMPLE 2

Effect upon P388 Ascites Tumor

The experiment was carried out by using groups of 6-weeks-old male $CDF_1$ mice, each group consisting of five mice. $10^6$ cells of P388 mouse leukemia were implanted into the abdominal cavities of the mice. A test compound was sufficiently wetted by adding 10 $\mu$l of Tween 80 relative to 1 mg of a sample, and 0.3% CMC (sodium carboxymethyl cellulose) solution was then added to the test compound to form a suspension. The resultant suspension was administered once 24 hours after implantation of the tumor, or repeatedly for consecutive 5 days from 24 hours after implantation of the tumor. The average survival day (T) in a group was calculated from the survival days of the respective mice in the group administered with the test compound at each dose. On the other hand, the average survival day (C) of a group which was not administered was measured, and the increased life span [ILS (%)] was calculated according to the following equation:

$[(T-C)/C] \times 100$ (%)

The results are shown in Table 3.

TABLE 3

| | ILS(%)[Dose (mg/kg)] | |
|---|---|---|
| Compd. No. | single admin. | five consec. admin. |
| 1 | 94 (200) | 113 (100) |
| 3 | 35 (50) | 56 (100) |
| 8 | 33 (100) | 75 (100) |
| 32 | 44 (100) | 53 (50) |
| 40 | 25 (50) | 51 (100) |
| 48 | 61 (25) | 26 (2.0) |
| 49 | 39 (50) | 67 (4.0) |
| 51 | 24 (200) | 53 (100) |
| 56 | 13 (200) | 51 (100) |
| 63 | 48 (6.25) | 54 (1.25) |
| 72 | 21 (50) | NT |
| 73 | 59 (25) | 41 (3.1) |
| 74 | 32 (6.3) | 43 (3.1) |
| 75 | 43 (100) | 40 (25) |
| 76 | 36 (50) | 50 (6.3) |
| 77 | 51 (25) | NT |
| 78 | 30 (25) | NT |
| 79 | 36 (13) | NT |
| 80 | 45 (6.3) | NT |
| 93 | 67 (25) | 50 (5.0) |
| 94 | 34 (50) | 35 (10) |
| 95 | 25 (50) | 41 (13) |
| 100 | 49 (200) | 31 (50) |
| 101 | 18 (13) | 33 (5.0) |
| 102 | 16 (100) | 73 (100) |
| 103 | 38 (50) | 47 (25) |
| 104 | 20 (50) | 52 (20) |
| 105 | 40 (25) | 67 (5.0) |
| 113 | 48 (50) | 74 (10) |
| 119 | 65 (50) | 99 (20) |
| 120 | 24 (13) | 54 (10) |
| 123 | 52 (50) | 70 (20) |

NT; not tested

TEST EXAMPLE 3

Effect against Delayed Type Hypersensitivity Footpad Reaction

Male BALB/c mice (8-weeks-old, Charles River Japan Inc.) were immunized by intradermally injection in the dorsal flank of 100 $\mu$l of 10 mM 2,4,6-trinitrobenzenesulfonic acid (TNBS) in saline. Five mice were used in each group, that is, control group [0.5% methylcellulose containing 10% dimethyl sulfoxide (DMSO)-administered group], Cyclosporine A (Sandoz)-administered group, and test compound-administered group wherein a determined concentration of test compound suspended in 0.5% methylcellulose containing 10% DMSO was administered. Each of Cyclosporine A and test compound was intraperitoneally administered 30 minutes before and once a day for 4 days after immunization. 50 μl of 10 mM TNBS was intradermally injected as a challenging antigen 5 days after immunization when antigen-sensitization was developed. Thickness of both footpads of each animal in each dose of test compound-administered group was measured with a dial thickness gauge 18 hours after antigen challenge, and the value of the difference in thickness of left and right footpad (T) was determined. On the other hand, thickness of both footpads in control group was measured, and the value of the difference in thickness of left and right footpad (C) was determined. Suppression rate in footpad reaction was calculated as [(C−T)/C]×100. The results are shown in Table 4.

TABLE 4

| Compd. No. | Suppression rate(%) [Dose (mg/kg × 5)] |
|---|---|
| 113 | 8.5 (3.0) |
|  | 69 (10) |
| Cyclosporine A | 89 (30) |

TEST EXAMPLE 4

Effect against anti-Trinitrophenol (TNP) Antibody Production

Mice which were used for the effect against delayed type hypersensitivity footpad reaction were bled, the sera were separated by centrifugation at 3000 rpm at 4° C. for 10 minutes, and then anti-TNP antibody titer was measured. For measuring anti-TNP antibody, enzyme-linked immunosorbent assay (ELISA) was used. 96 Well microtiter plates for ELISA (NUNC Inc.) were coated with TNP-BSA which was prepared according to the method of Schmitt-Verhulst, et al. [Journal of Experimental Medicine, 147, 352 (1978)], and after coating, culture supernatant was added and the mixture was reacted. Peroxidase labeled anti-mouse IgG+IgA+IgM (American Qualex International, Inc.) was added and bound to anti-TNP antibody in culture supernatant which was bound to plate. Orthophenylenediamine (Wako Pure Chemical Industries, Ltd) solution containing hydrogen peroxide (Wako Pure Chemical Industries, Ltd) was added and enzyme reaction was started. After sufficient coloring, coloring reaction was stopped by addition of 10% sulfonic acid (Wako Pure Chemical Industries, Ltd) and absorbance at 490 nm was measured by immunoreader (Intermed Japan, NJ-2000).

The results are shown in Table 5. Suppression rate of anti-TNP antibody production by test compound was calculated according to the following equation.

TABLE 5

$$\text{Suppression rate (\%)} = \frac{(\text{Absorbance in control group}) - (\text{Absorbance in test group})}{\text{Absorbance in control group}} \times 100$$

| Compd. No. | Suppression rate (%) [Dose (mg/kg × 5)] |
|---|---|
| 113 | 15 (3.0) |
|  | 57 (10) |
| Cyclosporine A | 39 (30) |

TEST EXAMPLE 5

T-Cell Proliferation Inhibitory Test Using Mouse Mixed Lymphocyte Reaction (MLR)

Spleen was sterilly removed from C3H/He mouse and single cell suspension was prepared. This suspension was irradiated with 2000R X-ray and adjusted into $8 \times 10^6$ cells/ml. 50 μl of lymph-node cells of BALB/c mouse (containing $2 \times 10^5$ cells), 50 μl of X-ray irradiated spleen cell suspension of C3H/He mouse (containing $4 \times 10^5$ cells), and 50 μl of determined concentration of test compound solution were added in each well of 96 well microtiter plate and cultured at 37° C. for 72 hours in the $CO_2$ incubater. Eight hours before the end of culture, [$^3$H]-Thymidine (1.85 KBq) was added. At the end of culture, cells were trapped on the filter paper by cell harvester and dried. Toluene type scintillater was added and radioactivity of [$^3$H]-Thymidine incorporated into cells was measured by liquid scintillation counter.

The results are shown in Table 6. Suppression rate of T-cell proliferation was calculated according to the following equation.

TABLE 6

$$\text{Suppression rate (\%)} = \frac{(\text{Radioactivity in control group}) - (\text{Radioactivity in test group})}{(\text{Radioactivity in control group}) - (\text{Radioactivity in X-ray irradiated C3H/He} + \text{Radioactivity in Balb/e})} \times 100$$

| Compd. No. | Suppression rate (%) [Concentration (M)] |
|---|---|
| 113 | 107 ($10^{-7}$) |
|  | 106 ($10^{-8}$) |
|  | 7.8 ($10^{-9}$) |

The compounds obtained according to the present invention are useful as antitumor agents, immunosuppresive agent, and therapeutic agents for an autoimmune disease, and can be used as they are or in various administration forms. For example, when Compounds (I) are used as injections, Compounds (I) may be dissolved in a diluting agent conventionally used in this field such as physiological saline, glucose injections, lactose injections, mannitol injections, or the like, freeze-dried on the basis of the Japanese Pharmacopoeia, or mixed with sodium chloride to form powder injections. Compounds (I) can also be used as lipid emulsions. These injections may contain an adjuvant such as polyethylene glycol, HCO-60 (surfactant: produced by Nikko Chemical Co., Ltd.), or the like; and a carrier such as ethanol and/or liposome, cyclodextrin, or the like. Although the injections are generally subjected to intravenous administration, they can also be subjected to arterial administration, intra-abdominal administration, or intrathoracic administration.

When Compounds (I) are mixed with appropriate excipients, disintegrators, binders, lubricants, and the like and formed to tablets, granules, powders, syrups, or the like by a conventional method, the compounds can also be used as oral agents. Compounds (I) may be mixed with carriers conventionally used and formed, by a conventional method, to suppositories which can be administered to the rectum.

The dose varies depending upon the mode of administration, the type of Compound (I), the age and conditions of a patient, etc., and the administration schedule can be changed according to the conditions of a patient or the dose. For example, administration can be made at a dose of 0.01 to 1000 mg/60 kg once a week or once every three weeks.

Reference Examples and Examples are described below.

BEST MODE FOR CARRYING OUT THE INVENTION

The physicochemical data of each compound were measured by the following apparatus.

$^1$H-NMR: Nihon Denshi JNM-GX270 (270 MHz) Hitachi R-90H (90 MHz) MS: Nihon Denshi JSM-D300 Elemental Analysis: Perkin Elmer 2400 CHN Analyzer

REFERENCE EXAMPLE 1

2-Bromo-3',4',5'-trimethoxyacetophenone (Compound XIa)

3',4',5'-Trimethoxyacetophenone (15.0 g) and pyrrolidone hydrotribromide (35.39 g) were dissolved in tetrahydrofuran (225 ml), followed by stirring at 40° C. for one hour. The reaction solution was cooled to room temperature, precipitated crystals were filtered off, and the filtrate was concentrated under reduced pressure. The residue was purified by silica gel column chromatography, and the obtained crude crystals were washed with hexane (100 ml) to give 2-bromo-3',4',5'-trimethoxyacetophenone (Compound XIa, 12.20 g).

$^1$H-NMR (90 MHz, CDCl$_3$) δ3.92 (s, 6H), 3.94 (s, 3H), 4.41 (s, 2H), 7.24 (s, 2H) EI-MS m/z=288, 290 (M$^+$) Elemental Analysis: C$_{11}$H$_{13}$BrO$_4$ Calcd.(%): C, 45.70; H, 4.53 Found (%): C, 45.61; H, 4.30

REFERENCE EXAMPLE 2

3',4',5'-Trimethoxystyrene oxide (Compound XIIIa)

2-Bromo-3',4',5'-trimethoxyacetophenone (Compound XIa, 10.00 g) obtained in Reference Example 1 was dissolved in methanol (350 ml), and sodium borohydride (1.31 g) was added thereto, followed by stirring at room temperature for 1.5 hours. Sodium borohydride (1.38 g) was added to the reaction solution and the mixture was stirred at room temperature for 0.5 hours. The reaction solution was concentrated under reduced pressure and the residue was purified by silica gel column chromatography to give 3',4',5'-trimethoxystyrene oxide (Compound XIIIa, 4.95 g).

$^1$H-NMR (90 MHz, CDCl$_3$) δ2.74 (dd, J=5.5, 2.4 Hz, 1H), 3.14 (dd, J=5.5, 4.3 Hz, 1H), 3.83 (m, 1H), 3.86 (s, 9H), 6.51 (s, 2H) EI-MS m/z=210 (M$^+$)

REFERENCE EXAMPLE 3

3',4',5'-Trimethoxystyrene oxide (Compound XIIIa)

3,4,5-Trimethoxybenzaldehyde (1.84 g) and trimethylsulfoxonium iodide (2.28 g) were dissolved in dimethyl sulfoxide (18 ml), and sodium hydride (414.4 mg) was added thereto, followed by stirring at room temperature for one hour. The reaction solution was subjected to partitioning between ethyl acetate and water, and the organic layer was successively washed with water and a saturated saline and dried over anhydrous sodium sulfate. The organic solvent was evaporated under reduced pressure to give 3',4',5'-trimethoxystyrene oxide (Compound XIIIa, 1.30 g).

REFERENCE EXAMPLE 4

2-Methoxy-3',4',5'-trimethoxyacetophenone (Compound IX-1)

3',4',5'-Trimethoxystyrene oxide (Compound XIIIa, 700.0 mg) obtained in Reference Example 2 was dissolved in methanol (100 ml), and sodium methoxide (0.90 g) was added thereto, followed by heating under reflux for 6 hours. The reaction solution was subjected to partitioning between chloroform and water, and the organic layer was washed with water, dried over anhydrous magnesium sulfate, and concentrated under reduced pressure. The residue was dissolved in acetone (29 ml), and Jones' reagent (1.5 ml) was added thereto under ice-cooling, followed by stirring for 30 minutes. 2-Propanol (1.5 ml) was added to the reaction solution, and the solution was concentrated under reduced pressure, followed by partitioning between ethyl acetate and water. The organic layer was successively washed with water and a saturated saline, dried over magnesium sulfate, and concentrated under reduced pressure. The residue was purified by silica gel column chromatography to give 2-methoxy-3',4',5'-trimethoxyacetophenone (Compound IX-1, 363.2 mg).

$^1$H-NMR (90 MHz, CDCl$_3$) δ3.51 (s, 3H), 3.92 (s, 9H), 4.65 (s, 2H), 7.21 (s, 2H) EI-MS m/z=240 (M$^+$)

REFERENCE EXAMPLE 5

2-Ethoxy-3',4',5'-trimethoxyacetophenone (Compound IX-2)

3',4',5'-Trimethoxystyrene oxide (Compound XIIIa, 1.00 g) obtained in Reference Example 2 was dissolved in ethanol (14 ml), and potassium tert-butoxide (1.07 g) was added thereto, followed by heating under reflux for one hour. The reaction solution was subjected to partitioning between ethyl acetate and water, and the organic layer was washed with water, dried over anhydrous magnesium sulfate, and concentrated under reduced pressure. The residue was dissolved in acetone (33 ml), and Jones' reagent (1.7 ml) was added thereto under ice-cooling, followed by stirring for 30 minutes. 2-Propanol (1.7 ml) was added to the reaction solution, and the solution was concentrated under reduced pressure, followed by partitioning between ethyl acetate and water. The organic layer was successively washed with water and a saturated saline, dried over magnesium sulfate, and concentrated under reduced pressure. The residue was purified by silica gel column chromatography to give 2-ethoxy-3',4',5'-trimethoxyacetophenone (Compound IX-2, 615.0 mg).

$^1$H-NMR (90 MHz, CDCl$_3$) δ1.27 (t, J=7.0 Hz, 3H), 3.68 (q, J=7.0 Hz, 2H), 3.91 (s, 9H), 4.64 (s, 2H), 7.28 (s, 2H) EI-MS m/z=254 (M$^+$)

REFERENCE EXAMPLE 6

3',4',5'-Trimethoxy-2-propyloxyacetophenone (Compound IX-3)

Substantially the same procedure as in Reference Example 5 was repeated using 3',4',5'-trimethoxystyrene oxide (Compound XIIIa, 1.00 g) obtained in Reference Example 2 and 1-propanol (17.8 ml) to give 3',4',5'-trimethoxy-2-propyloxyacetophenone (Compound IX-3, 615.0 mg).

$^1$H-NMR (90 MHz, CDCl$_3$) δ0.95 (t, J=6.9 Hz, 3H), 1.64 (m, 2H), 3.53 (q, J=6.9 Hz, 2H), 3.91 (s, 9H), 4.65 (s, 2H), 7.26 (s, 2H) FAB-MS m/z=269 (M$^+$+1)

REFERENCE EXAMPLE 7

2-Isopropyloxy-3',4',5'-trimethoxyacetophenone (Compound IX-4)

Substantially the same procedure as in Reference Example 5 was repeated using 3',4',5'-trimethoxystyrene oxide (Compound XIIIa, 1.00 g) obtained in Reference Example 2 and 2-propanol (18.2 ml) to give 2-isopropyloxy-3',4',5'-trimethoxyacetophenone (Compound IX-4, 548.9 mg).

$^1$H-NMR (90 MHz, CDCl$_3$) δ1.24 (d, J=7.0 Hz, 6H), 3.68 (m, 1H), 3.91 (s, 9H), 4.67 (s, 2H), 7.25 (s, 2H) EI-MS m/z=268 (M$^+$)

REFERENCE EXAMPLE 8

3',4',5'-Trimethoxy-2-(2-trimethylsilylethoxy)-acetophenone (Compound IX-5)

Substantially the same procedure as in Reference Example 5 was repeated using 3',4',5'-trimethoxystyrene oxide (Compound XIIIa, 1.05 g) obtained in Reference Example 2 and 2-trimethylsilylethanol (35.8 ml) to give 3',4',5'-trimethoxy-2-(2-trimethylsilylethoxy)acetophenone (Compound IX-5, 825.0 mg).

$^1$H-NMR (270 MHz, CDCl$_3$) δ0.02 (s, 9H), 1.04 (t, J=8.5 Hz, 2H), 3.66 (t, J=8.5 Hz, 2H), 3.91 (s, 6H), 3.92 (s, 3H), 4.67 (s, 2H), 7.24 (s, 2H) EI-MS m/z=326 (M$^+$)

REFERENCE EXAMPLE 9

3',4',5'-Trimethoxy-2-(3-trimethylsilylpropyloxy)-acetophenone (Compound IX-6)

Substantially the same procedure as in Reference Example 5 was repeated using 3',4',5'-trimethoxystyrene oxide (Compound XIIIa, 1.00 g) obtained in Reference Example 2 and 3-trimethylsilylpropanol (18.9 ml) to give 3',4',5'-trimethoxy-2-(3-trimethylsilylpropyloxy)acetophenone (Compound IX-6, 948.4 mg).

$^1$H-NMR (90 MHz, CDCl$_3$) δ0.00 (s, 9H), 0.53 (m, 2H), 1.68 (m, 2H), 3.53 (t, J=6.9 Hz, 2H), 3.92 (s, 9H), 4.67 (s, 2H), 7.27 (s, 2H) FAB-MS m/z=341 (M$^+$+1)

REFERENCE EXAMPLE 10

3',4',5'-Trimethoxy-2-(2-methylphenoxy)acetophenone (Compound IX-7)

2-Bromo-3',4',5'-trimethoxyacetophenone (Compound XIa, 1.45 g) obtained in Reference Example 1 and 2-methylphenol (648.0 mg) were dissolved in tetrahydrofuran (50 ml), and a 2N aqueous solution of sodium hydroxide (3.0 ml) was added thereto, followed by stirring at room temperature for one hour. The reaction solution was subjected to partitioning between ethyl acetate and water, and the organic layer was successively washed with water and a saturated saline, dried over anhydrous magnesium sulfate, and concentrated under reduced pressure. The residue was purified by silica gel column chromatography to give 3',4',5'-trimethoxy-2-(2-methylphenoxy)acetophenone (Compound IX-7, 0.69 g).

$^1$H-NMR (90 MHz, CDCl$_3$) δ2.30 (s, 3H), 3.90 (s, 6H), 3.93 (s, 3H), 5.20 (s, 2H), 6.76 (dd, J=6.9, 2.0 Hz, 1H), 6.93 (dd, J=6.9, 1.6 Hz, 1H), 7.13 (brt, J=6.9 Hz, 2H), 7.30 (s, 2H) EI-MS m/z=316 (M$^+$)

REFERENCE EXAMPLE 11

2-(4-Bromophenoxy)-3',4',5'-trimethoxyacetophenone (Compound IX-8)

Substantially the same procedure as in Reference Example 10 was repeated using 2-bromo-3',4',5'-trimethoxyacetophenone (Compound XIa, 1.45 g) obtained in Reference Example 1 and 4-bromophenol (1.04 g) to give 2-(4-bromophenoxy)-3',4',5'-trimethoxyacetophenone (Compound IX-8, 1.14 g).

$^1$H-NMR (90 MHz, CDCl$_3$) δ3.91 (s, 6H), 3.93 (s, 3H), 5.20 (s, 2H), 6.81 (d, J=9.0 Hz, 2H), 7.25 (s, 2H), 7.38 (d, J=9.0 Hz, 2H) EI-MS m/z=380, 382 (M$^+$)

REFERENCE EXAMPLE 12

2-Methylthio-3',4',5'-trimethoxyacetophenone (Compound IX-9)

2-Bromo-3',4',5'-trimethoxyacetophenone (Compound XIa, 0.87 g) obtained in Reference Example 1 was dissolved in tetrahydrofuran (60 ml), and a 10% aqueous solution of sodium methanethiolate (3.0 ml) was added thereto, followed by stirring at room temperature for one hour. The reaction solution was subjected to partitioning between ethyl acetate and water, and the organic layer was successively washed with a 5% aqueous solution of sodium bicarbonate and a saturated saline, dried over anhydrous magnesium sulfate, and concentrated under reduced pressure. The residue was purified by silica gel column chromatography to give 3',4',5'-trimethoxy-2-methylthioacetophenone (Compound IX-9, 1.02 g).

$^1$H-NMR (90 MHz, CDCl$_3$) δ2.16 (s, 3H), 3.73 (s, 2H), 3.92 (s, 9H), 7.26 (s, 2H) EI-MS m/z=256 (M$^+$)

REFERENCE EXAMPLE 13

3',4',5'-Trimethoxy-2-(2-trimethylsilylethylthio)-acetophenone (Compound IX-10)

2-Trimethylsilylethanethiol (1.00 g) was dissolved in tetrahydrofuran (75 ml), and a 1N aqueous solution of sodium hydroxide (7.5 ml) and then 2-bromo-3',4',5'-trimethoxyacetophenone (Compound XIa, 1.79 g) obtained in Reference Example 1 were added thereto, followed by stirring at room temperature for one hour. The reaction solution was subjected to partitioning between ethyl acetate and water, and the organic layer was successively washed with a 5% aqueous solution of sodium bicarbonate and a saturated saline, dried over anhydrous magnesium sulfate, and concentrated under reduced pressure. The residue was purified by silica gel column chromatography to give 3',4',5'-trimethoxy-2-(2-trimethylsilylethylthio)acetophenone (Compound IX-10, 2.07 g).

$^1$H-NMR (90 MHz, CDCl$_3$) δ0.00 (s, 9H), 0.86 (m, 2H), 2.62 (m, 2H), 3.74 (s, 2H), 3.89 (s, 9H), 7.22 (s, 2H) EI-MS m/z=342 (M$^+$)

REFERENCE EXAMPLE 14

2-(4-Fluorophenylthio)-3',4',5'-trimethoxyacetophenone (Compound IX-11)

Substantially the same procedure as in Reference Example 13 was repeated using 4-fluorothiophenol (0.82 g) and 2-bromo-3',4',5'-trimethoxyacetophenone (Compound XIa, 1.54 g) obtained in Reference Example 1 to give 2-(4-fluorophenylthio)-3',4',5'-trimethoxyacetophenone (Compound IX-11, 2.24 g).

$^1$H-NMR (90 MHz, CDCl$_3$) δ3.87 (s, 6H), 3.92 (s, 3H), 4.15 (s, 2H), 6.97 (t, J=8.9 Hz, 2H), 7.16 (s, 2H), 7.40 (dd, J=8.9, 5.3 Hz, 2H) EI-MS m/z=336 (M$^+$)

REFERENCE EXAMPLE 15

2-(2-Hydroxyethylthio)-3',4',5'-trimethoxyacetophenone (Compound IX-12)

Substantially the same procedure as in Reference Example 13 was repeated using 2-mercaptoethanol (0.82 g)

and 2-bromo-3',4',5'-trimethoxyacetophenone (Compound XIa, 2.60 g) obtained in Reference Example 1 to give 2-(2-hydroxyethylthio)-3',4',5'-trimethoxyacetophenone (Compound IX-12, 1.98 g).

$^1$H-NMR (90 MHz, CDCl$_3$) δ2.41 (t, J=6.0 Hz, 1H), 2.86 (t, J=6.0 Hz, 2H), 3.82 (q, J=6.0 Hz, 2H), 3.85 (s, 2H), 3.92 (s, 9H), 7.23 (s, 2H) EI-MS m/z=286 (M$^+$)

REFERENCE EXAMPLE 16

2-(2,3-Dihydroxypropylthio)-3',4',5'-trimethoxyacetophenone (Compound IX-13)

Substantially the same procedure as in Reference Example 13 was repeated using 1-mercapto-2,3-propanediol (12.25 g) and 2-bromo-3',4',5'-trimethoxyacetophenone (Compound XIa, 16.39 g) obtained in Reference Example 1 to give 2-(2,3-dihydroxypropylthio)-3',4',5'-trimethoxyacetophenone (Compound IX-13, 17.00 g).

$^1$H-NMR (270 MHz, CDCl$_3$) δ2.18 (t, J=4.0 Hz, 1H), 2.68 (dd, J=14.1, 7.9 Hz, 1H), 2.79 (dd, J=14.1, 4.5 Hz, 1H), 3.20 (d, J=3.5 Hz, 1H), 3.58 (m, 1H), 3.73 (m, 1H), 3.85 (m, 1H), 3.89 (s, 1H), 3.90 (s, 1H), 3.92 (s, 6H), 3.93 (s, 3H), 7.23 (s, 2H) FAB-MS m/z=317 (M$^+$+1)

REFERENCE EXAMPLE 17

2-(β-D-Glucosylthio)-3',4',5'-trimethoxyacetophenone (Compound IX-14)

2-Bromo-3',4',5'-trimethoxyacetophenone (Compound XIa, 289.0 mg) obtained in Reference Example 1 and 1-thio-β-D-glucose sodium salt (290.0 mg) were dissolved in a mixed solvent of tetrahydrofuran (25 ml) and methanol (10 ml), followed by stirring at room temperature for one hour. The reaction mixture was concentrated under reduced pressure and the residue was purified by silica gel column chromatography to give 2-(β-D-glucosylthio)-3',4',5'-trimethoxyacetophenone (Compound IX-14, 390.4 mg).

$^1$H-NMR (270 MHz, DMSO-d$_6$) δ3.01–3.21 (m, 4H), 3.46 (m, 1H), 3.66 (m, 1H), 3.77 (s, 3H), 3.86 (s, 6H), 4.15 (d, J=14.8 Hz, 1H), 4.23 (d, J=14.8 Hz, 1H), 4.33 (d, J=9.6 Hz, 1H), 4.40 (t, J=5.9 Hz, 1H), 4.91 (d, J=4.0 Hz, 1H), 5.03 (d, J=4.5 Hz, 1H), 5.15 (d, J=5.5 Hz, 1H), 7.27 (s, 2H) FAB-MS m/z=405 (M$^+$+1)

REFERENCE EXAMPLE 18

2-Carboxymethylthio-3',4',5'-trimethoxyacetophenone (Compound IX-15)

2-Bromo-3',4',5'-trimethoxyacetophenone (Compound XIa, 1.16 g) obtained in Reference Example 1 and thioglycolic acid (460.0 mg) were dissolved in tetrahydrofuran (30 ml), and a 2N aqueous solution of sodium hydroxide (5.0 ml) was added thereto, followed by stirring at room temperature for 16 hours. The reaction solution was subjected to partitioning between chloroform and 1N hydrochloric acid, and the organic layer was dried over anhydrous magnesium sulfate and concentrated under reduced pressure. The residue was purified by silica gel column chromatography to give 2-carboxymethylthio-3',4',5'-trimethoxyacetophenone (Compound IX-15, 0.92 g).

$^1$H-NMR (90 MHz, CDCl$_3$) δ3.39 (s, 2H), 3.92 (s, 9H), 4.02 (s, 2H), 6.04 (brs, 1H), 7.22 (s, 2H) FAB-MS m/z=301 (M$^+$+1)

REFERENCE EXAMPLE 19

2-(2-Diethylaminoethylthio)-3',4',5'-trimethoxyacetophenone (Compound IX-16)

2-Bromo-3',4',5'-trimethoxyacetophenone (Compound XIa, 1.16 g) obtained in Reference Example 1 and N,N-diethylaminoethanethiol hydrochloride (1.16 g) were dissolved in tetrahydrofuran (30 ml), and a 2N aqueous solution of sodium hydroxide (5.0 ml) was added thereto, followed by stirring at room temperature for 16 hours. The reaction solution was subjected to partitioning between chloroform and water, and the organic layer was dried over anhydrous magnesium sulfate and concentrated under reduced pressure. The residue was purified by silica gel column chromatography to give 2-(2-diethylaminoethylthio)-3',4',5'-trimethoxyacetophenone (Compound IX-16, 1.37 g).

$^1$H-NMR (90 MHz, CDCl$_3$) δ1.02 (t, J=7.1 Hz, 6H), 2.54 (q, J=7.1 Hz, 4H), 2.69 (s, 4H), 3.80 (s, 2H), 3.91 (s, 9H), 7.24 (s, 2H) EI-MS m/z=341 (M$^+$)

REFERENCE EXAMPLE 20

3',4',5'-Trimethoxy-2-(4-phenoxybutylthio)acetophenone (Compound IX-17)

Process 1

4-Phenoxybutyl bromide (5.73 g) was dissolved in dimethyl sulfoxide, and potassium thioacetate (10.71 g) was added thereto, followed by stirring at room temperature for 18 hours. The reaction solution was subjected to partitioning between ethyl acetate and water, and the organic layer was successively washed with water and a satureted saline, dried over anhydrous magnesium sulfate, and concentrated under reduced pressure. The residue was purified by silica gel column chromatography to give 1-acetylthio-4-phenoxybutane (Compound XIX-1, 5.53 g).

$^1$H-NMR (270 MHz, CDCl$_3$) δ1.70–1.92 (m, 4H), 2.34 (s, 3H), 2.95 (t, J=7.1 Hz, 2H), 3.97 (t, J=6.1 Hz, 2H), 6.88 (d, J=7.4 Hz, 2H), 6.93 (t, J=8.2 Hz, 1H), 7.28 (dd, J=8.2, 7.4 Hz, 2H) FAB-MS m/z=225 (M$^+$+1)

Process 2

1-Acetylthio-4-phenoxybutane (Compound XIX-1, 1.00 g) obtained in the above Process 1 was dissolved in piperidine (8 ml), followed by stirring at room temperature for 16 hours. Toluene was added to the reaction solution and the mixture was concentrated under reduced pressure. The residue and 2-bromo-3',4',5'-trimethoxyacetophenone (Compound XIa, 1.16 g) obtained in Reference Example 1 were dissolved in a mixed solvent of tetrahydrofuran (10 ml) and methanol (10 ml), and a 1N aqueous solution of sodium hydroxide (9.8 ml) was added thereto, followed by stirring at room temperature for 20 hours. The reaction solution was subjected to partitioning between ethyl acetate and water, and the organic layer was successively washed with water and a satureted saline, dried over anhydrous magnesium sulfate, and concentrated under reduced pressure. The residue was purified by silica gel column chromatography to give 3',4',5'-trimethoxy-2-(4-phenoxybutylthio)acetophenone (Compound IX-17, 353.4 mg).

$^1$H-NMR (270 MHz, CDCl$_3$) δ1.73–1.95 (m, 4H), 2.67 (t, J=6.9 Hz, 2H), 3.77 (s, 2H), 3.92 (s, 6H), 3.93 (s, 3H), 3.97 (t, J=5.9 Hz, 2H), 6.88 (dd, J=8.6, 0.7 Hz, 2H), 6.93 (t, J=7.6 Hz, 1H), 7.24 (s, 2H), 7.26. (m, 2H) EI-MS m/z=390 (M$^+$)

REFERENCE EXAMPLE 21

5,6-Dihydroxy-1-(3,4,5-trimethoxyphenyl)hexan-1-one (Compound IXh-1)

Process 1

3,4,5-Trimethoxybenzaldehyde (25.48 g) was dissolved in tetrahydrofuran (50 ml), and 4-pentenylmagnesium bromide (a 1M solution in tetrahydrofuran, 200 ml) was added thereto, followed by stirring at room temperature for 30 minutes. 1N Hydrochloric acid was added to the reaction solution and the mixture was extracted with ethyl acetate.

The organic layer was washed with a saturated saline, dried over anhydrous magnesium sulfate, and concentrated under reduced pressure to give 1-hydroxy-1-(3,4,5-trimethoxyphenyl)-5-hexene (Compound VIII-1, 34.58 g).

$^1$H-NMR (270 MHz, CDCl$_3$) δ1.34–1.89 (m, 4H), 2.12 (q, J=6.8 Hz, 2H), 3.86 (s, 3H), 3.89 (s, 6H), 4.62 (dd, J=7.3, 5.6 Hz, 1H), 4.96–5.07 (m, 2H), 5.83 (ddt, J=17.2, 10.2, 6.8 Hz, 1H), 6.59 (s, 2H), OH; not detected EI-MS m/z=266 (M$^+$)

Process 2

1-Hydroxy-1-(3,4,5-trimethoxyphenyl)-5-hexene (Compound VIII-1, 13.30 g) obtained in the above Process 1 was dissolved in acetone (250 ml), and Jones' reagent (18 ml) was added thereto under ice-cooling, followed by stirring for 30 minutes. 2-Propanol (20 ml) was added to the reaction solution, and the solution was concentrated under reduced pressure, followed by partitioning between ethyl acetate and water. The organic layer was successively washed with water and a saturated saline, dried over magnesium sulfate, and concentrated under reduced pressure. The residue was purified by silica gel column chromatography to give 1-(3,4,5-trimethoxyphenyl)-5-hexen-1-one (Compound IXf-1, 10.80 g).

$^1$H-NMR (270 MHz, CDCl$_3$) δ1.73 (quint, J=7.0 Hz, 2H), 2.04 (q, J=7.0 Hz, 2H), 2.83 (t, J=7.0 Hz, 2H), 3.797 (s, 3H), 3.803 (s, 6H), 4.86–4.98 (m, 2H), 5.72 (ddt, J=17.1, 10.2, 7.0 Hz, 1H), 7.10 (s, 2H) EI-MS m/z=264 (M$^+$)

Process 3

1-(3,4,5-Trimethoxyphenyl)-5-hexen-1-one (Compound IXf-1, 2.64 g) obtained in the above Process 2 was dissolved in chloroform (50 ml), metachloroperbenzoic acid (4.14 g) was added thereto, followed by stirring at room temperature for 32 hours. Insoluble matters were filtered off, and the filtrate was successively washed with a 10% aqueous solution of sodium thiosulfate and a 5% aqueous solution of sodium bicarbonate. The organic layer was dried over anhydrous sodium sulfate and concentrated under reduced pressure, and the residue was purified by silica gel column chromatography to give 5,6-epoxy-1-(3,4,5-trimethoxyphenyl)hexan-1-one (Compound IXg-1, 2.01 g).

$^1$H-NMR (270 MHz, CDCl$_3$) δ1.57 (m, 1H), 1.77 (m, 1H), 1.93 (quint, J=7.3 Hz, 2H), 2.50 (dd, J=5.0, 3.0 Hz, 1H), 2.77 (dd, J=5.0, 4.0 Hz, 1H), 2.88 (m, 1H), 2.97 (t, J=7.3 Hz, 2H), 3.92 (s, 9H), 7.23 (s, 2H) EI-MS m/z=280 (M$^+$)

Process 4

5,6-Epoxy-1-(3,4,5-trimethoxyphenyl)hexan-1-one (Compound IXg-1, 1.90 g) obtained in the above Process 3 was dissolved in methanol (30 ml), and sodium acetate (5.57 g) was added thereto, followed by heating under reflux for 48 hours. The reaction solution was concentrated under reduced pressure and the residue was purified by silica gel column chromatography to give 5,6-dihydroxy-1-(3,4,5-trimethoxyphenyl)hexan-1-one (Compound IXh-1, 0.87 g).

$^1$H-NMR (90 MHz, CDCl$_3$) δ1.53 (m, 2H), 1.87 (m, 2H), 2.68 (s, 2H), 3.01 (t, J=6.7 Hz, 2H), 3.32–3.80 (m, 3H), 3.92 (s, 9H), 7.22 (s, 2H) EI-MS m/z=298 (M$^+$)

REFERENCE EXAMPLE 22

3',4',5'-Trimethoxy-2-[(2S),(3R)-2,3,4-trihydroxybutylthio]acetophenone (Compound IX-18)

Process 1

(−)-2,3-O-Isopropylidene-D-threitol (9.95 g) was dissolved in tetrahydrofuran (270 ml), and sodium hydride(2.70 g, 60% mineral oil dispersion) and then tert-butyldimethylsilyl chloride (10.17 g) were added thereto, followed by stirring at room temperature for one hour. The reaction solution was concentrated under reduced pressure and the residue was purified by silica gel column chromatography to give (2R),(3R)-4-(tert-butyldimethylsilyloxy)-2,3-O-isopropylidene-1,2,3-butanetriol (15.87 g).

$^1$H-NMR (270 MHz, CDCl$_3$) δ0.09 (s, 6H), 0.90 (s, 9H), 1.40 (s, 3H), 1.42 (s, 3H), 2.93 (dd, J=8.3, 4.6 Hz, 1H), 3.62–3.83 (m, 3H), 3.83–3.93 (m, 2H), 3.99 (dt, J=7.5, 4.5 Hz, 1H) FAB-MS m/z=277 (M$^+$+1)

Process 2

(2R),(3R) -4-(tert-Butyldimethylsilyloxy)-2,3-O-isopropylidene-1,2,3-butanetriol (15.87 g) obtained in the above Process 1 was dissolved in pyridine (9.3 ml), and toluenesulfonyl chloride (17.5471 g) was added thereto, followed by stirring at room temperature for 18 hours. Tetrahydrofuran (95 ml) and then a 5% aqueous solution of sodium bicarbonate (200 ml) were added to the reaction solution, followed by stirring for 30 minutes. The reaction solution was subjected to partitioning between ethyl acetate and water, and the organic layer was successively washed with a 10% aqueous solution of citric acid and a saturated saline, dried over anhydrous magnesium sulfate, and concentrated under reduced pressure. The residue was purified by silica gel column chromatography to give (2R),(3R)-4-(tert-butyldimethylsilyloxy)-2,3-O-isopropylidene-1-toluenesulfonyloxy-2,3-butanediol (24.96 g).

$^1$H-NMR (270 MHz, CDCl$_3$) δ0.04 (s, 6H), 0.87 (s, 9H), 1.33 (s, 3H), 1.35 (s, 3H), 2.45 (s, 3H), 3.64 (dd, J=10.4, 6.1 Hz, 1H), 3.75–3.87 (m, 2H), 4.04–4.25 (m, 3H), 7.34 (d, J=8.3 Hz, 2H), 7.80 (d, J=8.3 Hz, 2H) EI-MS m/z=430 (M$^+$)

Process 3

(2R),(3R)-4-(tert-Butyldimethylsilyloxy)-2,3-O-isopropylidene-1-toluenesulfonyloxy-2,3-butanediol (5.62 g) obtained in the above Process 2 was dissolved in dimethyl sulfoxide (64 ml), and potassium thioacetate (5.62 g) was added thereto, followed by stirring at room temperature for 18 hours. The reaction solution was subjected to partitioning between ethyl acetate and water, and the organic layer was successively washed with water and a satureted saline, dried over anhydrous magnesium sulfate, and concentrated under reduced pressure. The residue was purified by silica gel column chromatography to give (2S),(3R)-1-acetylthio-4-(tert-butyldimethylsilyloxy)-2,3-O-isopropylidene-2,3-butanediol (4.04 g).

$^1$H-NMR (270 MHz, CDCl$_3$) δ0.01 (s, 6H), 0.83 (s, 9H), 1.31 (s, 3H), 1.34 (s, 3H), 2.28 (s, 3H), 3.01 (dd, J=13.9, 6.6 Hz, 1H), 3.25 (dd, J=13.9, 4.3 Hz, 1H), 3.61–3.76 (m, 3H), 4.01 (m, 1H) FAB-MS m/z=335 (M$^+$+1)

Process 4

(2S),(3R)-1-Acetylthio-4-(tert-butyldimethylsilyloxy)-2,3-O-isopropylidene-2,3-butanediol (3.50 g) obtained in the above Process 3 was dissolved in piperidine (20 ml), followed by stirring at room temperature for 30 minutes under an atmosphere of argon. Toluene (50 ml) was added to the reaction solution and the mixture was concentrated under reduced pressure. The residue was dissolved in toluene (50 ml) and the mixture was concentrated under reduced pressure. The residue was purified by silica gel column chromatography to give (2S),(3R)-4-(tert-butyldimethylsilyloxy)-2,3-dihydroxy-2,3-O-isopropylidene-1-butanethiol (2.81 g).

$^1$H-NMR (270 MHz, CDCl$_3$) δ0.06 (s, 6H), 0.88 (s, 9H), 1.39 (s, 3H), 1.42 (s, 3H), 1.62 (t, J=8.2 Hz, 1H), 2.71 (ddd, J=13.7, 8.0, 5.9 Hz, 1H), 2.82 (ddd, J=13.7, 8.7, 4.7 Hz, 1H), 3.69 (dd, J=10.2, 5.9 Hz, 1H), 3.79–3.91 (m, 2H), 4.03 (m, 1H) FAB-MS m/z=293 (M$^+$+1)

Process 5

(2S),(3R)-4-(tert-Butyldimethylsilyloxy)-2,3-dihydroxy-2,3-O-isopropylidene-1-butanethiol (2.71 g) obtained in the above Process 4 was dissolved in a mixed solvent of methanol (50 ml) and water (10 ml), and camphorsulfonic acid (1.08 g) was added thereto, followed by heating under reflux for one hour. The reaction solutuion was cooled to room temperature, and a 1N aqueous solution of sodium hydroxide (13.92 ml) and then a solution (50 ml) of 2-bromo-3',4',5'-trimethoxyacetophenone (Compound XIa, 2.68 g) obtained in Reference Example 1 in tetrahydrofuran were added thereto, followed by stirring for one hour. The reaction solution was concentrated under reduced pressure and the residue was purified by silica gel column chromatography to give 3',4',5'-trimethoxy-2-[(2S),(3R)-2,3,4-trihydroxybutylthio]acetophenone (Compound IX-18, 2.60 g).

$^1$H-NMR (270 MHz, CDCl$_3$) δ2.49 (t, J=5.6 Hz, 1H), 2.78 (dd, J=13.9, 8.1 Hz, 1H), 2.85 (dd, J=13.9, 3.6 Hz, 1H), 2.90 (d, J=6.6 Hz, 1H), 3.56 (d, J=4.0 Hz, 1H), 3.66 (m, 1H), 3.74–3.87 (m, 3H), 3.90 (s, 1H), 3.91 (s, 1H), 3.93 (s, 6H), 3.94 (s, 3H), 7.23 (s, 2H) FAB-MS m/z=347 (M$^+$+1)

REFERENCE EXAMPLE 23

3',4',5'-Trimethoxy-2-[(2R),(3S)-2,3,4-trihydroxybutylthio]acetophenone (Compound IX-19)

Process 1

Substantially the same procedure as in Process 1 of Reference Example 22 was repeated using (+)-2,3-O-isopropylidene-L-threitol (5.08 g) and tert-butyldimethylsilyl chloride (5.19 g) to give (2S),(3S)-4-(tert-butyldimethylsilyloxy)-2,3-O-isopropylidene-1,2,3-butanetriol (7.37 g).

$^1$H-NMR (270 MHz, CDCl$_3$) δ0.09 (s, 6H), 0.90 (s, 9H), 1.40 (s, 3H), 1.42 (s, 3H), 2.41 (dd, J=7.9, 4.6 Hz, 1H), 3.62–3.83 (m, 3H), 3.83–3.94 (m, 2H), 4.00 (dt, J=7.7, 4.5 Hz, 1H) FAB-MS m/z=277 (M$^+$+1)

Process 2

Substantially the same procedure as in Process 2 of Reference Example 22 was repeated using (2S),(3S)-4-(tert-butyldimethylsilyloxy)-2,3-O-isopropylidene-1,2,3-butanetriol (7.37 g) obtained in the above Process 1 and toluenesulfonyl chloride (8.13 g) to give (2S),(3S)-4-(tert-butyldimethylsilyloxy)-2,3-O-isopropylidene-1-toluenesulfonyloxy-2,3-butanediol (10.57 g).

$^1$H-NMR (270 MHz, CDCl$_3$) δ0.04 (s, 6H), 0.86 (s, 9H), 1.33 (s, 3H), 1.36 (s, 3H), 2.45 (s, 3H), 3.66 (dd, J=10.1, 6.1 Hz, 1H), 3.74–3.90 (m, 2H), 4.03–4.29 (m, 3H), 7.34 (d, J=8.5 Hz, 2H), 7.80 (d, J=8.5 Hz, 2H) FAB-MS m/z=431 (M$^+$+1)

Process 3

Substantially the same procedure as in Process 3 of Reference Example 22 was repeated using (2S),(3S)-4-(tert-butyldimethylsilyloxy)-2,3-O-isopropylidene-1-toluenesulfonyloxy-2,3-butanediol (5.57 g) obtained in the above Process 2 and potassium thioacetate (5.57 g) to give (2R),(3S)-1-acetylthio-4-(tert-butyldimethylsilyloxy)-2,3-O-isopropylidene-2,3-butanediol (4.18 g).

$^1$H-NMR (270 MHz, CDCl$_3$) δ0.08 (s, 6H), 0.91 (s, 9H), 1.38 (s, 3H), 1.42 (s, 3H), 2.36 (s, 3H), 3.08 (dd, J=13.9, 6.3 Hz, 1H), 3.31 (dd, J=13.9, 4.3 Hz, 1H), 3.68–3.85 (m, 3H), 4.08 (m, 1H) FAB-MS m/z=335 (M$^+$+1)

Process 4

Substantially the same procedure as in Process 4 of Reference Example 22 was repeated using (2R),(3S)-1-acetylthio-4-(tert-butyldimethylsilyloxy)-2,3-O-isopropylidene-2,3-butanediol (3.97 g) obtained in the above Process 3 and piperidine (22 ml) to give (2R),(3S)-4-(tert-butyldimethylsilyloxy)-2,3-dihydroxy-2,3-O-isopropylidene-1-butanethiol (3.18 g).

$^1$H-NMR (270 MHz, CDCl$_3$) δ0.07 (s, 6H), 0.90 (s, 9H), 1.40 (s, 3H), 1.43 (s, 3H), 1.63 (t, J=8.4 Hz, 1H), 2.72 (ddd, J=13.9, 8.2, 5.9 Hz, 1H), 2.84 (ddd, J=13.9, 8.4, 4.1 Hz, 1H), 3.70 (dd, J=10.2, 5.9 Hz, 1H), 3.79–3.94 (m, 2H), 4.04 (m, 1H) FAB-MS m/z=293 (M$^+$+1)

Process 5

Substantially the same procedure as in Process 5 of Reference Example 22 was repeated using (2R),(3S)-4-(tert-butyldimethylsilyloxy)-2,3-dihydroxy-2,3-O-isopropylidene-1-butanethiol (2.97 g) obtained in the above Process 3 and 2-bromo-3',4',5'-trimethoxyacetophenone (Compound XIa, 2.94 g) obtained in Reference Example 1 to give 3',4',5'-trimethoxy2-[(2R),(3S)-2,3,4-trihydroxybutylthio]acetophenone (Compound IX-19, 3.11 g).

$^1$H-NMR (270 MHz, CDCl$_3$) δ2.53 (t, J=5.9 Hz, 1H), 2.77 (dd, J=13.5, 7.4 Hz, 1H), 2.85 (dd, J=13.5, 3.6 Hz, 1H), 2.94 (d, J=6.6 Hz, 1H), 3.58 (d, J=4.0 Hz, 1H), 3.65 (m, 1H), 3.74–3.87 (m, 3H), 3.90 (s, 1H), 3.91 (s, 1H), 3.92 (s, 6H), 3.94 (s, 3H), 7.23 (s, 2H) FAB-MS m/z=347 (M$^+$+1)

REFERENCE EXAMPLE 24

Indole-5-carbaldehyde

Indole-5-carboxylic acid (3.10 g) was dissolved in tetrahydrofuran (50 ml), and lithium aluminium hydride (1.50 g) was added thereto, followed by heating under reflux for 20 hours. The reaction solution was cooled to room temperature, and ethyl acetate and then a 2N aqueous solution of sodium hydroxide were added thereto to cease the reaction. The reaction solution was dried over anhydrous sodium sulfate and insoluble matters were filtered off. Manganese dioxide (30.00 g) was added to the filtrate, followed by stirring at room temperature for 96 hours. Insoluble matters were filtered off and the filtrate was concentrated under reduced pressure. The residue was purified by silica gel column chromatography to give indole-5-carbaldehyde (1.43 g).

$^1$H-NMR (90 MHz, CDCl$_3$) δ6.72 (m, 1H), 7.33 (t, J=3.0 Hz, 1H), 7.49 (d, J=8.6 Hz, 1H), 7.97 (dd, J=8.6, 1.3 Hz, 1H), 8.19 (brs, 1H), 8.57 (brs, 1H), 10.04 (s, 1H) EI-MS m/z=145 (M$^+$)

EXAMPLE 1

(E)-3-(Indol-3-yl)-1-(3,4,5-trimethoxyphenyl)-2-propen-1-one (Compound 1)

3',4',5'-Trimethoxyacetophenone (42.0 g) and indole-3-carboxaldehyde (29.0 g) were dissolved in ethanol (200 ml), and piperidine (17.0 g) was added thereto, followed by heating under reflux for 48 hours. The reaction solution was ice-cooled, and the precipitated crystals were collected by filtration to give Compound 1 (44.4 g).

$^1$H-NMR (270 MHz, DMSO-d$_6$) δ3.78 (s, 3H), 3.92 (s, 6H), 7.19–7.28 (m, 2H), 7.36 (s, 2H), 7.49 (m, 1H), 7.61 (d, J=15.4 Hz, 1H), 8.04 (m, 1H), 8.06 (d, J=15.4 Hz, 1H), 8.13 (d, J=3.0 Hz, 1H), 11.88 (brs, 1H) EI-MS m/z=337 (M$^+$)

EXAMPLE 2

(E)-3-(1-Methylindol-3-yl)-1-(3,4,5-trimethoxyphenyl)-2-propen-1-one (Compound 2)

Compound 1 (1.0 g) obtained in Example 1 was dissolved in acetone (50 ml), and methyl iodide (1.42 g) and potassium carbonate (1.0 g) were added thereto, followed by heating under reflux for 72 hours. Insoluble matters were filtered off, and the filtrate was concentrated under reduced pressure. The residue was suspended in ethyl acetate (20 ml) in a condition of heating under reflux, and insoluble matters were filtered off. Hexane (25 ml) was added to the filtrate, and the precipitated crystals were collected by filtration to give Compound 2 (0.85 g).

$^1$H-NMR (270 MHz, DMSO-d$_6$) δ3.77 (s, 3H), 3.87 (s, 3H), 3.92 (s, 6H), 7.21–7.34 (m, 2H), 7.36 (s, 2H), 7.48 (d, J=7.8 Hz, 1H), 7.60 (d, J=15.5 Hz, 1H), 8.00 (d, J=15.5 Hz, 1H), 8.03 (d, J=7.8 Hz, 1H), 8.12 (s, 1H) EI-MS m/z=351 (M$^+$)

EXAMPLE 3

(E)-3-(1-Ethylindol-3-yl)-1-(3,4,5-trimethoxyphenyl)-2-propen-1-one (Compound 3)

Compound 1 (1.69 g) obtained in Example 1 was dissolved in a mixed solvent of N,N-dimethylformamide (12.5 ml) and tetrahydrofuran (12.5 ml), and ethyl bromide (817.3 mg) and sodium hydride (300 mg, 60% mineral oil dispersion) were added thereto, followed by stirring at room temperature for 3 hours. Ice was added to the reaction solution, and the mixture was subjected to partitioning between ethyl acetate and water. The organic layer was dried over magnesium sulfate and concentrated under reduced pressure, and the residue was recrystallized from 2-propanol to give Compound 3 (1.54 g).

$^1$H-NMR (270 MHz, CDCl$_3$) δ1.54 (t, J=7.3 Hz, 3H), 3.94 (s, 3H), 3.97 (s, 6H), 4.23 (q, J=7.3 Hz, 2H), 7.31 (s, 2H), 7.34 (m, 2H), 7.41 (m, 1H), 7.48 (d, J=15.5 Hz, 1H), 7.56 (s, 1H), 7.99 (m, 1H), 8.09 (d, J=15.5 Hz, 1H) EI-MS m/z=365 (M$^+$)

EXAMPLE 4

(E)-3-(1-Butylindol-3-yl)-1-(3,4,5-trimethoxyphenyl)-2-propen-1-one (Compound 4)

Substantially the same procedure as in Example 3 was repeated using Compound 1 (1.69 g) obtained in Example 1 and butyl bromide (0.81 ml) to give Compound 4 (1.48 g).

$^1$H-NMR (270 MHz, CDCl$_3$) δ0.97 (t, J=7.4 Hz, 3H), 1.38 (m, 2H), 1.87 (m, 2H), 3.94 (s, 3H), 3.97 (s, 6H), 4.17 (t, J=7.4 Hz, 2H), 7.31 (s, 2H), 7.32 (m, 2H), 7.41 (m, 1H), 7.50 (d, J=15.6 Hz, 1H), 7.52 (s, 1H), 7.99 (m, 1H), 8.09 (d, J=15.6 Hz, 1H) EI-MS m/z=393 (M$^+$)

EXAMPLE 5

(E)-3-(1-Isobutylindol-3-yl)-1-(3,4,5-trimethoxyphenyl)-2-propen-1-one (Compound 5)

Substantially the same procedure as in Example 3 was repeated using Compound 1 (1.69 g) obtained in Example 1 and isobutyl bromide (0.82 ml) to give Compound 5 (1.32 g).

$^1$H-NMR (270 MHz, CDCl$_3$) δ0.97 (d, J=6.9 Hz, 6H), 2.24 (m, 1H), 3.94 (s, 3H), 3.95 (d, J=6.9 Hz, 2H), 3.97 (s, 6H), 7.30 (m, 2H), 7.31 (s, 2H), 7.35 (m, 1H), 7.48 (d, J=15.3 Hz, 1H), 7.50 (s, 1H), 7.99 (m, 1H), 8.09 (d, J=15.3 Hz, 1H) EI-MS m/z=393 (M$^+$)

EXAMPLE 6

(E)-3-(1-Acetylindol-3-yl)-1-(3,4,5-trimethoxyphenyl)-2-propen-1-one (Compound 6)

A mixture of Compound 1 (1.69 g) obtained in Example 1, acetic anhydride (5.04 g) and pyridine (5.6 ml) was heated at 100° C. for 12 hours. The reaction solution was subjected to partitioning between chloroform and a 10% aqueous solution of citric acid. The organic layer was concentrated under reduced pressure, and the residue was recrystallized from ethyl acetate to give Compound 6 (1.32 g).

$^1$H-NMR (270 MHz, CDCl$_3$) δ2.72 (s, 3H), 3.96 (s, 3H), 3.97 (s, 6H), 7.31 (s, 2H), 7.45 (m, 2H), 7.63 (d, J=15.6 Hz, 1H), 7.81 (s, 1H), 7.93 (dd, J=5.9, 1.9 Hz, 1H), 7.97 (d, J=15.6 Hz, 1H), 8.51 (dd, J=7.4, 1.9 Hz, 1H) EI-MS m/z=379 (M$^+$)

EXAMPLE 7

(E)-3-(1-Ethoxycarbonylindol-3-yl)-1-(3,4,5-trimethoxy-phenyl)-2-propen-1-one (Compound 7)

A mixture of Compound 1 (1.69 g) obtained in Example 1, ethoxycarbonyl chloride (2.5 ml) and pyridine (5 ml) was stirred at room temperature for 16 hours. The reaction solution was subjected to partitioning between chloroform and a 10% aqueous solution of citric acid. The organic layer was concentrated under reduced pressure, and the residue was recrystallized from 2-propanol to give Compound 7 (1.83 g).

$^1$H-NMR (270 MHz, CDCl$_3$) δ1.51 (t, J=7.2 Hz, 3H), 3.95 (s, 3H), 3.97 (s, 6H), 4.55 (q, J=7.2 Hz, 2H), 7.30 (s, 2H), 7.42 (m, 2H), 7.60 (d, J=15.8 Hz, 1H), 7.92 (m, 1H), 7.99 (d, J=15.8 Hz, 1H), 8.04 (s, 1H), 8.26 (m, 1H) EI-MS m/z=409 (M$^+$)

EXAMPLE 8

(E)-3-(1-Benzoylindol-3-yl)-1-(3,4,5-trimethoxyphenyl)-2-propen-1-one (Compound 8)

Substantially the same procedure as in Example 7 was repeated using Compound 1 (1.69 g) obtained in Example 1 and benzoyl chloride (1.16 ml) to give Compound 8 (0.91 g).

$^1$H-NMR (270 MHz, CDCl$_3$) δ3.95 (s, 3H), 3.96 (s, 6H), 7.28 (s, 2H), 7.45–8.00 (m, 11H), 8.44 (m, 1H) EI-MS m/z=441 (M$^+$)

EXAMPLE 9

(E)-3-(1-Methanesulfonylindol-3-yl)-1-(3,4,5-trimethoxyphenyl)-2-propen-1-one (Compound 9)

Substantially the same procedure as in Example 3 was repeated using Compound 1 (1.69 g) obtained in Example 1 and methanesulfonyl chloride (0.86 g) except that the reaction product was purified by silica gel column chromatography and that the obtained crude crystals were recrystallized from ethanol, to give Compound 9 (1.67 g).

$^1$H-NMR (270 MHz, CDCl$_3$) δ3.22 (s, 3H), 3.95 (s, 3H), 3.97 (s, 6H), 7.30 (s, 2H), 7.47 (m, 2H), 7.60 (d, J=15.5 Hz, 1H), 7.88 (s, 1H), 7.97 (m, 2H), 7.98 (d, J=15.8 Hz, 1H) EI-MS m/z=415 (M$^+$)

EXAMPLE 10

(E)-3-(1-Benzenesulfonylindol-3-yl)-1-(3,4,5-trimethoxyphenyl)-2-propen-1-one (Compound 10)

Substantially the same procedure as in Example 9 was repeated using Compound 1 (337.4 mg) obtained in Example 1 and benzenesulfonyl chloride (176.6 mg) to give Compound 10 (409.9 mg).

$^1$H-NMR (270 MHz, CDCl$_3$) δ3.95 (s, 3H), 3.97 (s, 6H), 7.329 (s, 2H), 7.30–7.64 (m, 6H), 7.85–8.07 (m, 6H) EI-MS m/z=477 (M$^+$)

EXAMPLE 11

(E)-3-[1-(4-Methyl-1,3-dioxol-2-on-5-yl) methylindol-3-yl]-1-(3,4,5-trimethoxyphenyl)-2-propen-1-one (Compound 11)

Substantially the same procedure as in Example 3 was repeated using Compound 1 (2.37 g) obtained in Example 1 and 4-chloromethyl-5-methyl-1,3-dioxol-2-one (1.63 g) except that the obtained crude crystals were further purified by preparative high-pressure liquid chromatography (HPLC), to give Compound 11 (188 mg).

EI-MS m/z=449 ($M^+$)

EXAMPLE 12

(E)-3-(2-Methylindol-3-yl)-1-(3,4,5-trimethoxyphenyl)-2-propen-1-one (Compound 12)

Substantially the same procedure as in Example 1 was repeated using 3',4',5'-trimethoxyacetophenone (2.10 g) and 2-methylindole-3-carboxaldehyde (1.59 g) except that the obtained crude crystals were recrystallized from ethanol, to give Compound 12 (2.13 g).

$^1$H-NMR (270 MHz, $CDCl_3$) δ2.63 (s, 3H), 3.93 (s, 3H), 3.97 (s, 6H), 7.22 (m, 2H), 7.32 (s, 2H), 7.38 (m, 1H), 7.47 (d, J=15.3 Hz, 1H), 7.91 (dd, J=6.4, 2.5 Hz, 1H), 8.17 (d, J=15.3 Hz, 1H), 10.66 (brs, 1H) EI-MS m/z=351 ($M^+$)

EXAMPLE 13

(E)-3-(2-Chloro-1-methylindol-3-yl)-1-(3,4,5-trimethoxyphenyl)-2-propen-1-one (Compound 13)

Process 1

3',4',5'-Trimethoxyacetophenone (15.0 g) and pyrrolidone hydrotribromide (35.39 g) were dissolved in tetrahydrofuran (225 ml), followed by stirring at 40° C. for one hour. The reaction solution was cooled to room temperature, insoluble materials were filtered off, and the filtrate was concentrated under reduced pressure. The residue was purified by silica gel column chromatography, and the obtained crude crystals were washed with hexane (100 ml) to give 2-bromo-3',4',5'-trimethoxyacetophenone (Compound VII-1, 12.2 g).

$^1$H-NMR (90 MHz, $CDCl_3$) δ3.92 (s, 6H), 3.94 (s, 3H), 4.41 (s, 2H), 7.24 (s, 2H) EI-MS m/z=288, 290 ($M^+$)

Process 2

Compound VII-1 (12.12 g) obtained in the above Process 1 and triethyl phosphite (6.97 g) were dissolved in toluene (83 ml), followed by heating under reflux for 24 hours. The reaction solution was concentrated under reduced pressure, and then purified by silica gel column chromatography to give 2-diethylphosphono-3',4',5'-trimethoxyacetophenone (Compound IIc-1, 8.36 g).

$^1$H-NMR (90 MHz, $CDCl_3$) δ1.30 (t, J=7.0 Hz, 6H), 3.60 (d, J=22.6 Hz, 2H), 3.92 (s, 9H), 4.14 (dq, J=8.1, 7.0 Hz, 4H), 7.30 (s, 2H) EI-MS m/z=346 ($M^+$)

Process 3

2-Chloroindole-3-carboxaldehyde (2.69 g) and methyl iodide (4.26 g) were dissolved in a mixed solvent of tetrahydrofuran (25 ml) and dimethylsulfoxide (25 ml), and sodium hydride (0.66 g, 60% mineral oil dispersion) was added thereto at 0° C. A 10% aqueous solution of citric acid was added to the reaction solution, and the mixture was extracted with ethyl acetate. The organic layer was washed with water and then a saturated saline, and dried over anhydrous magnesium sulfate. After concentration under reduced pressure, the residue was washed with hexane (30 ml) to give 2-chloro-1-methylindole-3-carboxaldehyde (2.54 g).

$^1$H-NMR (90 MHz, $CDCl_3$) δ3.80 (s, 3H), 7.29 (m, 3H), 8.29 (m, 1H), 10.11 (s, 1H) EI-MS m/z=193, 195 ($M^+$)

Process 4

Compound IIc-1 (692.6 mg) obtained in the above Process 2 was dissolved in tetrahydrofuran (136 ml), and potassium tert-butoxide (224.4 mg) and 2-chloro-1-methylindole-3-carboxaldehyde (287.2 mg) obtained in the above Process 3 were added thereto, followed by heating under reflux for 72 hours. The reaction solution was poured into ice-water, and the mixture was extracted with ethyl acetate. The organic layer was washed with water and then a saturated saline, and dried over anhydrous magnesium sulfate. After concentration under reduced pressure, the residue was purified by silica gel column chromatography, and the obtained crude crystals were recrystallized from 2-propanol to give Compound 13 (713.8 mg).

$^1$H-NMR (270 MHz, $CDCl_3$) δ3.83 (s, 3H), 3.95 (s, 3H), 3.97 (s, 6H), 7.31 (s, 2H), 7.32 (m, 1H), 7.35 (m, 2H), 7.59 (d, J=15.5 Hz, 1H), 7.93 (m, 1H), 8.12 (d, J=15.5 Hz, 1H) EI-MS m/z=385 ($M^+$)

EXAMPLE 14

(E)-3-[2-(4-Chlorophenyl)indol-3-yl]-1-(3,4,5-trimethoxyphenyl)-2-propen-1-one (Compound 14)

Substantially the same procedure as in Example 12 was repeated using 3',4',5'-trimethoxyacetophenone (0.84 g) and 2-(4-chlorophenyl)indole-3-carboxaldehyde (2.56 g) to give Compound 14 (3.04 g).

$^1$H-NMR (270 MHz, $CDCl_3$) δ3.94 (s, 9H), 7.29 (s, 2H), 7.34 (m, 2H), 7.45 (m, 1H), 7.46 (d, J=9.9 Hz, 2H), 7.51 (d, J=9.9 Hz, 2H), 7.63 (d, J=15.3 Hz, 1H), 8.03 (m, 1H), 8.11 (d, J=15.3 Hz, 1H), 8.80 (s, 1H) EI-MS m/z=447 ($M^+$)

EXAMPLE 15

(E)-3-(4-Methylindol-3-yl)-1-(3,4,5-trimethoxyphenyl)-2-propen-1-one (Compound 15)

Process 1

A mixture of N,N-dimethylformamide (6 ml) and phosphorus oxychloride (1.78 g) was stirred at room temperature for 30 minutes. 4-Methylindole (1.0 g) was added to the reaction solution, followed by stirring at room temperature for one hour. A 5N aqueous solution of sodium hydroxide (15 ml) was added thereto, followed by stirring at 100° C. for further 30 minutes. The reaction solution was cooled, and the precipitated crystals were collected by filtration to give 4-methylindole-3-carboxaldehyde (Compound III-1, 1.14 g).

$^1$H-NMR (90 MHz, $CDCl_3$) δ2.83 (s, 3H), 6.98–7.29 (m, 3H), 7.89 (d, J=3.0 Hz, 1H), 9.11 (brs, 1H), 10.10 (s, 1H) EI-MS m/z=159 ($M^+$)

Process 2

Substantially the same procedure as in Example 1 was repeated using 3',4',5'-trimethoxyacetophenone (2.10 g) and Compound III-1 (2.56 g) obtained in the above Process 1 except that the obtained crude crystals were recrystallized from a mixed solvent of ethanol and acetone, to give Compound 15 (0.67 g).

$^1$H-NMR (270 MHz, $CDCl_3$) δ2.80 (s, 3H), 3.94 (s, 3H), 3.95 (s, 6H), 6.99 (d, J=7.4 Hz, 1H), 7.15 (t, J=7.4 Hz, 1H), 7.295 (s, 2H), 7.295 (d, J=16.1 Hz, 1H), 7.30 (d, J=7.4 Hz, 1H), 7.80 (d, J=3.0 Hz, 1H), 8.48 (d, J=16.1 Hz, 1H), 8.63 (brs, 1H) EI-MS m/z=351 ($M^+$)

EXAMPLE 16

(E)-3-(1,4-Dimethylindol-3-yl)-1-(3,4,5-trimethoxyphenyl)-2-propen-1-one (Compound 16)

Process 1

Compound III-1 (38 mg) obtained in Process 1 of Example 15 was reacted according to the same method in Example 2. The insoluble matters were filtered off, and the filtrate was concentrated under reduced pressure. The residue was subjected to partitioning between ethyl acetate and water, and the organic layer was dried over anhydrous magnesium sulfate and concentrated under reduced pressure to give 1,4-dimethylindole-3-carboxaldehyde (28.5 mg).

$^1$H-NMR (90 MHz, CDCl$_3$) δ2.82 (s, 3H), 3.81 (s, 3H), 6.89–7.29 (m, 3H), 7.73 (s, 1H), 10.06 (s, 1H) EI-MS m/z=173 (M$^+$)

Process 2

Substantially the same procedure as in Process 4 of Example 13 was repeated using Compound IIc-1 (83 mg) obtained in Process 2 of Example 13 and 1,4-dimethylindole-3-carboxaldehyde (28 mg) obtained in the above Process 1 except that the reaction product was purified by silica gel column chromatography, to give Compound 16 (13.1 mg).

$^1$H-NMR (270 MHz, CDCl$_3$) δ2.80 (s, 3H), 3.86 (s, 3H), 3.94 (s, 3H), 3.96 (s, 6H), 7.00 (m, 1H), 7.15–7.30 (m, 5H), 7.69 (s, 1H), 8.48 (d, J=15.3 Hz, 1H) EI-MS m/z=365 (M$^+$)

EXAMPLE 17

(E)-3-(4-Nitroindol-3-yl)-1-(3,4,5-trimethoxyphenyl)-2-propen-1-one (Compound 17)

Substantially the same procedure as in Example 1 was repeated using 3',4',5'-trimethoxyacetophenoe (903 mg) and 4-nitroindole-3-carboxaldehyde (816 mg) to give Compound 17 (695 mg).

$^1$H-NMR (270 MHz, DMSO-d$_6$) δ3.83 (s, 3H), 3.91 (s, 6H), 7.37 (dd, J=8.4, 7.9 Hz, 1H), 7.38 (s, 2H), 7.54 (d, J=15.4 Hz, 1H), 7.91 (d, J=8.4 Hz, 1H), 7.92 (d, J=7.9 Hz, 1H), 8.21 (d, J=15.4 Hz, 1H), 8.65 (s, 1H), 12.66 (brs, 1H) EI-MS m/z=382 (M$^+$)

EXAMPLE 18

(E)-3-(4-Methoxyindol-3-yl)-1-(3,4,5-trimethoxyphenyl)-2-propen-1-one (Compound 18)

Process 1

Substantially the same procedure as in Process 1 of Example 15 was repeated using 4-methoxyindole (1 g) to give 4-methoxyindole-3-carboxaldehyde (1.17 g).

$^1$H-NMR (90 MHz, CDCl$_3$) δ3.97 (s, 3H), 6.52–7.35 (m, 4H), 8.24 (d, J=4.8 Hz, 1H), 10.33 (s, 1H) EI-MS m/z=175 (M$^+$)

Process 2

Substantially the same procedure as in Example 12 was repeated using 3',4',5'-trimethoxyacetophenone (1.2 g) and 4-methoxyindole-3-carboxaldehyde (1 g) obtained in the above Process 1 to give Compound 18 (1.65 g).

$^1$H-NMR (270 MHz, CDCl$_3$) δ3.77 (s, 3H), 3.91 (s, 6H), 3.95 (s, 3H), 6.67 (dd, J=7.2, 1.3 Hz, 1H), 7.04–7.14 (m, 2H), 7.36 (s, 2H), 7.73 (d, J=15.8 Hz, 1H), 8.24 (d, J=3.0 Hz, 1H), 8.37 (d, J=15.8 Hz, 1H), 8.68 (brs, 1H) EI-MS m/z=367 (M$^+$)

EXAMPLE 19

(E)-3-(4,7-Dimethoxyindol-3-yl)-1-(3,4,5-trimethoxy-phenyl)-2-propen-1-one (Compound 19)

Process 1

Substantially the same procedure as in Process 1 of Example 15 was repeated using 4,7-dimethoxyindole (0.78 g) to give 4,7-dimethoxyindole-3-carboxaldehyde (0.91 g).

$^1$H-NMR (90 MHz, CDCl$_3$) δ3.92 (s, 6H), 6.58 (s, 2H), 7.89 (s, 1H), 10.48 (s, 1H) EI-MS m/z=205 (M$^+$)

Process 2

Substantially the same procedure as in Example 1 was repeated using 3',4',5'-trimethoxyacetophenone (1.05 g) and 4,7-dimethoxyindole-3-carboxaldehyde (0.75 g) obtained in the above Process 1 except that the reaction product was recrystallized from a mixed solvent of ethanol and water, to give Compound 19 (1.00 g).

$^1$H-NMR (270 MHz, CDCl$_3$) δ3.93 (s, 3H), 3.94 (s, 3H), 3.94 (s, 3H), 3.95 (s, 6H), 6.50 (d, J=8.4 Hz, 1H), 6.59 (d, J=8.4 Hz, 2H), 7.30 (s, 2H), 7.57 (d, J=15.8 Hz, 1H), 7.62 (d, J=3.0 Hz, 1H), 8.38 (d, J=15.8 Hz, 1H), 8.78 (brs, 1H) EI-MS m/z=397 (M$^+$)

EXAMPLE 20

(E)-3-(5-Methylindol-3-yl)-1-(3,4,5-trimethoxyphenyl)-2-propen-1-one (Compound 20)

Substantially the same procedure as in Example 1 was repeated using 3',4',5'-trimethoxyacetophenone (2.1 g) and 5-methylindole-3-carboxaldehyde (1.59 g) except that the reaction solution was concentrated under reduced pressure, that the residue was purified by silica gel column chromatography, and that the obtained crude crystals were recrystallized from a mixed solvent of ethyl acetate and hexane, to give Compound 20 (1.16 g).

$^1$H-NMR (270 MHz, DMSO-d$_6$) δ2.46 (s, 3H), 3.77 (s, 3H), 3.92 (s, 6H), 7.06 (d, J=8.2 Hz, 1H), 7.36 (s, 2H), 7.37 (d, J=8.2 Hz, 1H), 7.60 (d, J=15.4 Hz, 1H), 7.82 (s, 1H), 8.02 (d, J=15.4 Hz, 1H), 8.07 (d, J=3.0 Hz, 1H), 11.77 (brs, 1H) EI-MS m/z=351 (M$^+$)

EXAMPLE 21

(E)-3-(5-Nitroindol-3-yl)-1-(3,4,5-trimethoxyphenyl)-2-propen-1-one (Compound 21)

3',4',5'-Trimethoxyacetophenone (1.31 g) and 5-nitroindole-3-carboxaldehyde (1.18 g) were dissolved in N,N-dimethylformamide (20 ml), and piperidine (528.7 mg) was added thereto, followed by stirring at 100° C. for 72 hours. The reaction solution was concentrated under reduced pressure, and the residue was purified by silica gel column chromatography. The obtained crude crystals were recrystallized from methanol to give Compound 21 (125 mg).

$^1$H-NMR (270 MHz, DMSO-d$_6$) δ3.79 (s, 3H), 3.93 (s, 6H), 7.41 (s, 2H), 7.67 (d, J=8.4 Hz, 1H), 7.79 (d, J=15.6 Hz, 1H), 8.07 (d, J=15.6 Hz, 1H), 8.11 (dd, J=8.4, 2.0 Hz, 1H), 8.41 (s, 1H), 8.93 (d, J=2.0 Hz, 1H), 12.48 (s, 1H) CI-MS m/z=382 (M)

EXAMPLE 22

(E)-3-(5-Dimethylamino-1-methylindol-3-yl)-1-(3,4,5-trimethoxyphenyl)-2-propen-1-one (Compound 22)

Process 1

5-Nitroindole-3-carboxaldehyde (2 g) was dissolved in N,N-dimethylformamide (40 ml), and potassium carbonate (4.0 g) and methyl iodide (5 ml) were added thereto, followed by stirring at 60° C. for 24 hours. The reaction solution was subjected to partitioning with chloroform, methanol and water, and the organic layer was dried over magnesium sulfate. After concentration under reduced pressure, the residue was rinsed with ethyl acetate to give 1-methyl-5-nitroindole-3-carboxaldehyde (Compound III-2, 1.99 g).

$^1$H-NMR (90 MHz, CDCl$_3$) δ3.95 (s, 3H), 7.42 (d, J=9.1 Hz, 1H), 7.83 (s, 1H), 8.23 (dd, J=9.1, 2.2 Hz, 1H), 9.18 (d, J=2.2 Hz, 1H), 10.04 (s, 1H) EI-MS m/z=204 (M$^+$)

Process 2

Compound III-2 (50 mg) obtained in the above Process 1 and 10% palladium charcoal were suspended in a mixed solvent of methanol (20 ml) and N,N-dimethylformamide (5 ml), and formalin (0.5 ml) was added thereto, followed by stirring at room temperature for 24 hours under an atmosphere of hydrogen. The catalyst was filtered off, and the filtrate was subjected to partitioning between chloroform and water. The organic layer was washed with water, dried over sodium sulfate and concentrated under reduced pressure to give 5-dimethylamino-1-methylindole-3-carboxaldehyde (45 mg).

$^1$H-NMR (90 MHz, DMSO-d$_6$) δ2.91 (s, 6H), 3.82 (s, 3H), 6.85 (m, 2H), 7.32 (m, 1H), 8.04 (s, 1H), 9.82 (s, 1H) EI-MS m/z=202 (M$^+$)

Process 3

5-Dimethylamino-1-methylindole-3-carboxaldehyde (45 mg) obtained in the above Process 2 and Compound IId-1 (229 mg) obtained in Process 2 of Example 13 were dissolved in tetrahydrofuran (10 ml), and potassium tert-butoxide (74 mg) was added thereto, followed by stirring for 72 hours. The reaction solution was subjected to partitioning with chloroform, methanol and water, and the organic layer was dried over magnesium sulfate. After concentration under reduced pressure, the residue was purified by silica gel column chromatography and then medium-pressure silica gel column chromatography to give Compound 22 (17 mg).

$^1$H-NMR (270 MHz, DMSO-d$_6$) δ2.97 (s, 6H), 3.78 (s, 3H), 3.81 (s, 3H), 3.91 (S, 6H), 6.91 (dd, J=9.1, 2.2 Hz, 1H), 7.21 (d, J=2.2 Hz, 1H), 7.36 (s, 2H), 7.39 (d, J=9.1 Hz, 1H), 7.54 (d, J=15.4 Hz, 1H), 7.96 (s, 1H), 7.99 (d, J=15.4 Hz, 1H) EI-MS m/z=394 (M$^+$)

EXAMPLE 23

(E)-3-(5-Ethoxycarbonylamino-1-methylindol-3-yl)-1-(3,4,5-trimethoxyphenyl)-2-propen-1-one (Compound 23)

Process 1

Compound III-2 (200 mg) obtained in Process 1 of Example 22 was suspended in a mixed solvent of methanol (25 ml) and water (25 ml), and sodium hydrosulfite (1.0 g) was added thereto, followed by heating under reflux for one hour.

Process 2

A 5% aqueous solution of sodium bicarbonate (20 ml) was added to the reaction solution obtained in the above Process 1, and ethyl chloroformate (125 mg) was added thereto, followed by stirring at room temperature for 24 hours. The reaction solution was subjected to partitioning between chloroform and water, and the organic layer was dried over magnesium sulfate. After concentration under reduced pressure, the residue was purified by silica gel column chromatography to give 5-ethoxycarbonylamino-1-methylindole-3-carboxaldehyde (38 mg).

$^1$H-NMR (90 MHz, DMSO-d$_6$) δ1.26 (t, J=7.0 Hz, 3H), 3.85 (s, 3H), 4.14 (q, J=7.0 Hz, 1H), 7.42 (s, 2H), 8.15 (s, 1H), 8.27 (s, 1H), 9.67 (s, 1H), 9.84 (s, 1H) EI-MS m/z=246 (M$^+$)

Process 3

Substantially the same procedure as in Process 3 of Example 22 was repeated using 5-ethoxycarbonylamino-1-methylindole-3-carboxaldehyde (20 mg) obtained in the above Process 2 and Compound IIc-1 (84 mg) obtained in Process 2 of Example 13 except that the residue was purified by silica gel column chromatography and that the obtained crude crystals were rinsed with ethyl acetate, to give Compound 23 (17 mg).

$^1$H-NMR (270 MHz, DMSO-d$_6$) δ1.29 (t, J=7.1 Hz, 3H), 3.78 (s, 3H), 3.83 (s, 3H), 3.95 (s, 6H), 4.15 (q, J=7.1 Hz, 2H), 7.26 (dd, J=8.9, 2.0 Hz, 1H), 7.35 (s, 2H), 7.46 (d, J=8.9 Hz, 1H), 7.56 (d, J=15.3 Hz, 1H), 7.97 (d, J=15.3 Hz, 1H), 8.02 (s, 1H), 8.49 (s, 1H), 9.63 (s, 1H) EI-MS m/z=438 (M$^+$)

EXAMPLE 24

(E)-3-(5-Acetamido-1-methylindol-3-yl)-1-(3,4,5-trimethoxyphenyl)-2-propen-1-one (Compound 24)

Process 1

Substantially the same procedure as in Process 1 of Example 23 was repeated using Compound III-2 (200 mg) obtained in Process 1 of Example 22. Pyridine (5 ml) and acetic anhydride (5 ml) were added to the reaction solution, followed by stirring at room temperature for 24 hours. The reaction solution was subjected to partitioning between chloroform and a 10% aqueous solution of citric acid, and the organic layer was dried over magnesium sulfate. After concentration under reduced pressure, the residue was suspended in toluene, and the mixture was concentrated again under reduced pressure to give 5-acetamido-1-methylindole-3-carboxaldehyde (53 mg).

$^1$H-NMR (270 MHz, DMSO-d$_6$) δ2.16 (s, 3H), 3.87 (s, 3H), 7.30 (d, J=8.9 Hz, 1H), 7.71 (s, 1H), 7.92 (dd, J=8.9, 1.9 Hz, 1H), 8.18 (d, J=1.9 Hz, 1H), 9.18 (brs, 1H), 9.94 (s, 1H) EI-MS m/z=216 (M$^+$)

Process 2

Substantially the same procedure as in Process 3 of Example 23 was repeated using 5-acetamido-1-methylindole-3-carboxaldehyde (37 mg) obtained in the above Process 1 and Compound IIc-1 (118 mg) obtained in Process 2 of Example 13 to give Compound 24 (37 mg).

$^1$H-NMR (270 MHz, DMSO-d$_6$) δ2.08 (s, 3H), 3.77 (s, 3H), 3.84 (s, 3H), 3.94 (s, 6H), 7.32 (dd, J=8.9, 1.5 Hz, 1H), 7.39 (s, 2H), 7.48 (d, J=8.9 Hz, 1H), 7.56 (d, J=15.8 Hz, 1H), 7.96 (d, J=15.8 Hz, 1H), 8.04 (s, 1H), 8.63 (d, J=1.5 Hz, 1H), 9.97 (s, 1H) FAB-MS m/z=409 (M$^+$+1)

EXAMPLE 25

(E)-3-(5-Methoxyindol-3-yl)-1-(3,4,5-trimethoxyphenyl)-2-propen-1-one (Compound 25)

Substantially the same procedure as in Example 1 was repeated using 3',4',5'-trimethoxyacetophenone (1.2 g) and 5-methoxyindole-3-carboxaldehyde (1 g) except that the obtained crude crystals were recrystallized from 2-propanol, to give Compound 25 (1.09 g).

$^1$H-NMR (270 MHz, DMSO-d$_6$) δ3.77 (s, 3H), 3.87 (s, 3H), 3.91 (s, 6H), 6.86 (dd, J=8.7, 2.3 Hz, 1H), 7.38 (d, J=8.7 Hz, 1H), 7.39 (s, 2H), 7.47 (d, J=2.3 Hz, 1H), 7.58 (d, J=15.5 Hz, 1H), 7.93 (d, J=2.5 Hz, 1H), 8.01 (d, J=15.5 Hz, 1H), 8.68 (s, 1H) EI-MS m/z=397 (M$^+$)

EXAMPLE 26

(E)-3-(5,6-Dimethoxyindol-3-yl)-1-(3,4,5-trimethoxy-phenyl)-2-propen-1-one (Compound 26)

Process 1

Substantially the same procedure as in Process 1 of Example 15 was repeated using 5,6-dimethoxyindole (1 g) to give 5,6-dimethoxyindole-3-carboxaldehyde (914 mg).

$^1$H-NMR (90 MHz, DMSO-d$_6$) δ3.81 (s, 6H), 7.02 (s, 1H), 7.57 (s, 1H), 8.02 (d, J=2.9 Hz, 1H), 9.85 (s, 1H), 11.77 (brs, 1H) EI-MS m/z=205 (M$^+$)

Process 2

Substantially the same procedure as in Example 1 was repeated using 3',4',5'-trimethoxyacetophenone (834 mg)

and 5,6-dimethoxyindole-3-carboxaldehyde (814 mg) obtained in the above Process 1 except that the obtained crude crystals were recrystallized from a mixed solvent of 2-propanol and acetone, to give Compound 26 (900 mg).

$^1$H-NMR (270 MHz, DMSO-d$_6$) δ3.77 (s, 3H), 3.82 (s, 3H), 3.90 (s, 3H), 3.91 (s, 6H), 7.00 (s, 1H), 7.39 (s, 2H), 7.48 (s, 1H), 7.58 (d, J=15.5 Hz, 1H), 7.93 (d, J=2.5 Hz, 1H), 8.01 (d, J=15.5 Hz, 1H), 8.68 (s, 1H) EI-MS m/z=397 (M$^+$)

EXAMPLE 27

(E)-3-(5-Hydroxy-6-methoxyindol-3-yl)-1-(3,4,5-trimethoxyphenyl)-2-propen-1-one (Compound 27)

Process 1

Substantially the same procedure as in Process 1 of Example 15 was repeated using 5-benzyloxy-6-methoxyindole (0.85 g) to give 5-benzyloxy-6-methoxyindole-3-carboxaldehyde (0.79 g)

$^1$H-NMR (90 MHz, CDCl$_3$) δ3.90 (s, 3H), 5.20 (s, 2H), 6.91 (s, 1H), 7.25–7.55 (s, 5H), 7.66 (d, J=3.3 Hz, 1H), 7.88 (s, 1H), 8.59 (brs, 1H), 9.97 (s, 1H) EI-MS m/z=281 (M$^+$)

Process 2

5-Benzyloxy-6-methoxyindole-3-carboxaldehyde (0.75 g) was suspended in a mixed solvent of methanol (60 ml) and ethyl acetate (20 ml), and 10% palladium on carbon (85 mg) was added thereto, followed by stirring at room temperature for one hour under an atmosphere of hydrogen. The catalyst was filtered off, and the filtrate was concentrated under reduced pressure to give 5-hydroxy-6-methoxyindole-3-carboxaldehyde (0.51 g).

$^1$H-NMR (90 MHz, CDCl$_3$) δ3.89 (s, 3H), 6.95 (s, 1H), 7.62 (s, 1H), 7.74 (d, J=3.1 Hz, 1H), 8.17 (s, 1H), 9.86 (s, 1H), 11.43 (s, 1H) EI-MS m/z=191 (M$^+$)

Process 3

Substantially the same procedure as in Example 12 was repeated using 3',4',5'-trimethoxyacetophenone (0.55 g) and 5-hydroxy-6-methoxyindole-3-carboxaldehyde (0.51 g) obtained in the above Process 2 to give Compound 27 (93 mg).

$^1$H-NMR (270 MHz, CDCl$_3$) δ3.94 (s, 3H), 3.95 (s, 3H), 3.96 (s, 6H), 5.62 (s, 1H), 6.92 (s, 1H), 7.31 (s, 2H), 7.43 (d, J=15.5 Hz, 1H), 7.49 (d, J=3.0 Hz, 1H), 7.50 (s, 1H), 8.05 (d, J=15.5 Hz, 1H), 8.53 (s, 1H) EI-MS m/z=383 (M$^+$)

EXAMPLE 28

(E)-3-(5-Benzyloxyindol-3-yl)-1-(3,4,5-trimethoxyphenyl)-2-propen-1-one (Compound 28)

Substantially the same procedure as in Example 1 was repeated using 3',4',5'-trimethoxyacetophenone (2.1 g) and 5-benzyloxyindole-3-carboxaldehyde (2.51 g) except that the obtained crude crystals were recrystallized twice from acetone, to give Compound 28 (107 mg).

$^1$H-NMR (270 MHz, CDCl$_3$) δ3.942 (s, 3H), 3.947 (s, 6H), 5.16 (s, 2H), 7.04 (dd, J=7.9, 2.2 Hz, 1H), 7.29 (s, 2H), 7.31–7.55 (m, 8H), 7.61 (d, J=2.9 Hz, 1H), 8.08 (d, J=15.7 Hz, 1H), 8.53 (s, 1H) EI-MS m/z=443 (M$^+$)

EXAMPLE 29

(E)-3-(5-Fluoroindol-3-yl)-1-(3,4,5-trimethoxyphenyl)-2-propen-1-one (Compound 29)

Substantially the same procedure as in Example 12 was repeated using 3',4',5'-trimethoxyacetophenone (2.1 g) and 5-fluoroindole-3-carboxaldehyde (1.63 g) to give Compound 29 (2.1 g).

$^1$H-NMR (270 MHz, CDCl$_3$) δ3.95 (s, 3H), 3.97 (s, 6H), 7.07 (td, J=8.9, 2.5 Hz, 1H), 7.31 (s, 2H), 7.39 (dd, J=8.9, 4.5 Hz, 1H), 7.44 (d, J=15.5 Hz, 1H), 7.62 (dd, J=9.4, 2.5 Hz, 1H), 7.66 (d, J=3.0 Hz, 1H), 8.05 (d, J=15.5 Hz, 1H), 8.82 (brs, 1H) EI-MS m/z=355 (M$^+$)

EXAMPLE 30

(E)-3-(5-Chloroindol-3-yl)-1-(3,4,5-trimethoxyphenyl)-2-propen-1-one (Compound 30)

Substantially the same procedure as in Example 12 was repeated using 3',4',5'-trimethoxyacetophenone (2.1 g) and 5-chloroindole-3-carboxaldehyde (1.8 g) to give Compound 30 (2.94 g).

$^1$H-NMR (270 MHz, DMSO-d$_6$) δ3.77 (s, 3H), 3.92 (s, 6H), 7.23 (dd, J=8.5, 2.0 Hz, 1H), 7.38 (s, 2H), 7.50 (d, J=8.5 Hz, 1H), 7.63 (d, J=15.5 Hz, 1H), 8.00 (d, J=15.5 Hz, 1H), 8.07 (d, J=2.0 Hz, 1H), 8.22 (s, 1H), 12.05 (brs, 1H) EI-MS m/z=371, 373 (M$^+$)

EXAMPLE 31

(E)-3-(5-Bromoindol-3-yl)-1-(3,4,5-trimethoxyphenyl)-2-propen-1-one (Compound 31)

Substantially the same procedure as in Example 12 was repeated using 3',4',5'-trimethoxyacetophenone (2.1 g) and 5-bromoindole-3-carboxaldehyde (2.24 g) except that the obtained crystals were recrystallized from ethyl acetate, to give Compound 31 (2.73 g).

$^1$H-NMR (270 MHz, DMSO-d$_6$) δ3.78 (s, 3H), 3.92 (s, 6H), 7.34 (dd, J=8.8, 2.0 Hz, 1H), 7.38 (s, 2H), 7.46 (d, J=8.8 Hz, 1H), 7.63 (d, J=15.3 Hz, 1H), 8.00 (d, J=15.3 Hz, 1H), 8.19 (d, J=2.0 Hz, 1H), 8.20 (s, 1H), 12.04 (brs, 1H) EI-MS m/z=415, 417 (M$^+$)

EXAMPLE 32

(E)-3-(6-Methylindol-3-yl)-1-(3,4,5-trimethoxyphenyl)-2-propen-1-one (Compound 32)

Process 1

Substantially the same procedure as in Process 1 of Example 15 was repeated using 6-methylindole (1.15 g) to give 6-methylindole-3-carboxaldehyde (1.34 g).

1H-NMR (270 MHz, CDCl$_3$) δ2.47 (s, 3H), 7.10 (d, J=8.0 Hz, 1H), 7.24 (brs, 1H), 7.75 (d, J=2.6 Hz, 1H), 8.18 (d, J=8.0 Hz, 1H), 9.99 (s, 1H), 10.55 (brs, 1H) EI-MS m/z=159 (M$^+$)

Process 2

Substantially the same procedure as in Example 12 was repeated using 3',4',5'-trimethoxyacetophenone (1.05 g) and 6-methylindole-3-carboxaldehyde (0.8 g) obtained in the above Process 1 to give Compound 32 (0.77 g).

$^1$H-NMR (270 MHz, CDCl$_3$) δ2.49 (s, 3H), 3.94 (s, 3H), 3.96 (s, 6H), 7.14 (d, J=8.2 Hz, 1H), 7.25 (s, 1H), 7.31 (s, 2H), 7.50 (d, J=15.5 Hz, 1H), 7.56 (d, J=3.0 Hz, 1H), 7.87 (d, J=8.2 Hz, 1H), 8.08 (d, J=15.5 Hz, 1H), 8.68 (brs, 1H) EI-MS m/z=351 (M$^+$)

EXAMPLE 33

(E)-3-(6-Trifluoromethylindol-3-yl)-1-(3,4,5-trimethoxyphenyl)-2-propen-1-one (Compound 33)

Process 1

Substantially the same procedure as in Process 1 of Example 15 was repeated using 6-trifluoromethylindole (1.85 g) to give 6-trifluoromethylindole-3-carboxaldehyde (1.90 g).

$^1$H-NMR (90 MHz, CDCl$_3$) δ7.44 (brd, J=8.4 Hz, 1H), 7.73 (brs, 1H), 7.80 (d, J=3.0 Hz, 1H), 8.33 (d, J=8.4 Hz, 1H), 10.03 (s, 1H) EI-MS m/z=213 (M$^+$)

Process 2

Substantially the same procedure as in Example 12 was repeated using 3',4',5'-trimethoxyacetophenone (2.1 g) and 6-trifluoromethylindole-3-carboxaldehyde (1.67 g) obtained in the above Process 1 to give Compound 33 (1.38 g).

$^1$H-NMR (270 MHz, CDCl$_3$) δ3.95 (s, 3H), 3.97 (s, 6H), 7.31 (s, 2H), 7.53 (d, J=15.8 Hz, 1H), 7.54 (brd, J=8.4 Hz, 1H), 7.75 (brs, 1H), 7.78 (d, J=3.0 Hz, 1H), 8.06 (d, J=8.4 Hz, 1H), 8.09 (d, J=15.8 Hz, 1H), 9.02 (brs, 1H) EI-MS m/z=405 (M$^+$)

EXAMPLE 34

(E)-3-(6-Nitroindol-3-yl)-1-(3,4,5-trimethoxyphenyl)-2-propen-1-one (Compound 34)

Substantially the same procedure as in Example 21 was repeated using 3',4',5'-trimethoxyacetophenone (1.25 g) and 6-nitroindole-3-carboxaldehyde (1.13 g) except that the obtained product was further purified by preparative HPLC, that the eluting solution was cooled, and that the precipitated crystals were collected by filtration, to give Compound 34 (26 mg).

$^1$H-NMR (270 MHz, DMSO-d$_6$) δ3.78 (s, 3H), 3.92 (s, 6H), 7.39 (s, 2H), 7.76 (d, J=15.9 Hz, 1H), 8.055 (dd, J=8.9, 2.0 Hz, 1H), 8.056 (d, J=15.9 Hz, 1H), 8.25 (d, J=8.9 Hz, 1H), 8.41 (d, J=2.0 Hz, 1H), 8.54 (s, 1H), 12.51 (brs, 1H) CI-MS m/z=382 (M)

EXAMPLE 35

(E)-3-(6-Dimethyl-1-methylindol-3-yl)-1-(3,4,5-trimethoxyphenyl)-2-propen-1-one (Compound 35)

Process 1

Substantially the same procedure as in Process 1 of Example 22 was repeated using 6-nitroindole-3-carboxaldehyde (2 g) to give 1-methyl-6-nitroindole-3-carboxaldehyde (Compound III-3, 1.91 g).

$^1$H-NMR (270 MHz, DMSO-d$_6$) δ4.04 (s, 3H), 8.12 (dd, J=8.2, 2.0 Hz, 1H), 8.29 (d, J=8.2 Hz, 1H), 8.32 (s, 1H), 8.43 (d, J=2.0 Hz, 1H) EI-MS m/z=204 (M$^+$)

Process 2

Substantially the same procedure as in Process 2 of Example 22 was repeated using Compound III-3 (350 mg) obtained in the above Process 1 to give 6-dimethylamino-1-methylindole-3-carboxaldehyde (203 mg).

$^1$H-NMR (90 MHz, DMSO-d$_6$) δ2.96 (s, 6H), 3.81 (s, 3H), 6.70 (d, J=1.8 Hz, 1H), 6.80 (dd, J=8.8, 1.8 Hz, 1H), 7.88 (d, J=8.8 Hz, 1H), 7.97 (s, 1H), 9.78 (s, 1H) EI-MS m/z=202 (M$^+$)

Process 3

Substantially the same procedure as in Example 20 was repeated using 3',4',5'-trimethoxyacetophenone (184 mg) and 6-dimethylamino-1-methylindole-3-carboxaldehyde (177 mg) obtained in the above Process 2 except that the obtained crude crystals were purified by preparative HPLC, to give Compound 35 (110 mg).

$^1$H-NMR (270 MHz, DMSO-d$_6$) δ2.98 (s, 6H), 3.77 (s, 3H), 3.78 (s, 3H), 3.91 (s, 6H), 6.72 (d, J=2.3 Hz, 1H), 6.84 (dd, J=8.9, 2.3 Hz, 1H), 7.33 (s, 2H), 7.53 (d, J=15.3 Hz, 1H), 7.84 (s, 1H), 7.88 (d, J=8.9 Hz, 1H), 7.93 (d, J=15.3 Hz, 1H) EI-MS m/z=394 (M$^+$)

EXAMPLE 36

(E)-3-(6-Ethoxycarbonylamino-1-methylindol-3-yl)-1-(3,4,5-trimethoxyphenyl)-2-propen-1-one (Compound 36)

Process 1

Substantially the same procedure as in Processes 1 and 2 of Example 23 was repeated using Compound III-3 (200 mg) obtained in Process 1 of Example 35 to give 6-ethoxycarbonylamino-1-methylindole-3-carboxaldehyde (38 mg).

$^1$H-NMR (90 MHz, DMSO-d$_6$) δ1.27 (d, J=7.0 Hz, 3H), 3.82 (s, 3H), 4.15 (q, J=7.0 Hz, 2H), 7.21 (dd, J=8.5, 1.8 Hz, 1H), 7.81 (d, J=1.8 Hz, 1H), 7.94 (d, J=8.5 Hz, 1H), 8.13 (s, 1H), 9.64 (s, 1H), 9.78 (s, 1H) EI-MS m/z=246 (M$^+$)

Process 2

Substantially the same procedure as in Process 3 of Example 23 was repeated using 6-ethoxycarbonylamino-1-methylindole-3-carboxaldehyde (20 mg) obtained in the above Process 1 and Compound II-c (84 mg) obtained in Process 2 of Example 13 to give Compound 36 (17 mg).

$^1$H-NMR (270 MHz, DMSO-d$_6$) δ1.28 (t, J=7.0 Hz, 3H), 3.77 (s, 3H), 3.79 (s, 3H), 3.91 (s, 6H), 4.16 (q, J=7.0 Hz, 1H), 7.23 (dd, J=8.5, 1.3 Hz, 1H), 7.35 (s, 2H), 7.54 (d, J=15.3 Hz, 1H), 7.81 (s, 1H), 7.94 (d, J=15.3 Hz, 1H), 7.96 (d, J=8.5 Hz, 1H), 8.01 (s, 1H), 9.71 (s, 1H) EI-MS m/z=438 (M$^+$)

EXAMPLE 37

(E)-3-(6-Acetamidoindol-3-yl)-1-(3,4,5-trimethoxyphenyl)-2-propen-1-one (Compound 37)

Process 1

Substantially the same procedure as in Example 3 was repeated using 6-nitroindole-3-carboxaldehyde (2.3 g) and acetic anhydride (2.47 g) to give 1-acetyl-6-nitroindole-3-carboxaldehyde (2.62 g).

$^1$H-NMR (90 MHz, DMSO-d$_6$) δ2.81 (s, 3H), 8.31 (s, 2H), 9.20 (s, 2H), 10.13 (s, 1H) EI-MS m/z=232 (M$^+$)

Process 2

Substantially the same procedure as in Process 1 of Example 24 was repeated using 1-acetyl-6-nitroindole-3-carboxaldehyde (100 mg) obtained in the above Process 1 to give 6-acetamidoindole-3-carboxaldehyde (28 mg).

$^1$H-NMR (90 MHz, DMSO-d$_6$) δ2.08 (s, 3H), 7.18 (dd, J=8.4, 1.7 Hz, 1H), 7.95 (d, J=8.4 Hz, 1H), 8.10 (d, J=1.7 Hz, 1H), 8.16 (d, J=2.8 Hz, 1H), 9.88 (s, 1H), 9.93 (brs, 1H), 11.95 (brs, 1H) EI-MS m/z=202 (M$^+$)

Process 3

Substantially the same procedure as in Example 1 was repeated using 3',4',5'-trimethoxyacetophenone (252 mg) and 6-acetamidoindole-3-carboxaldehyde (243 mg) obtained in the above Process 2 except that the obtained crude crystals were recrystallized from a mixed solvent of ethanol, acetone and water, to give Compound 37 (98 mg).

$^1$H-NMR (270 MHz, DMSO-d$_6$) δ2.08 (s, 3H), 3.77 (s, 3H), 3.87 (s, 6H), 7.23 (dd, J=8.6, 1.5 Hz, 1H), 7.35 (s, 2H), 7 55 (d, J=15.5 Hz, 1H), 7.95 (d, J=8.6 Hz, 1H), 7.99 (d, J=15.5 Hz, 1H), 8.03 (d, J=3.0 Hz, 1H), 8.08 (d, J=1.5 Hz, 1H), 9.96 (s, 1H), 11.77 (brs, 1H) EI-MS m/z=394 (M$^+$)

EXAMPLE 38

(E)-3-(6-Acetamido-1-methylindol-3-yl)-1-(3,4,5-trimethoxyphenyl)-2-propen-1-one (Compound 38)

Process 1

Substantially the same procedure as in Process 1 of Example 24 was repeated using Compound III-3 (200 mg) obtained in Process 1 of Example 35 to give 6-acetamido-1-methylindole-3-carboxaldehyde (68 mg).

$^1$H-NMR (90 MHz, DMSO-d$_6$) δ2.18 (s, 3H), 3.85 (s, 3H), 7.12 (dd, J=8.7, 1.6 Hz, 1H), 7.70 (s, 1H), 8.11 (d, J=8.7 Hz, 1H), 8.19 (d, J=1.6 Hz, 1H), 8.16 (d, J=2.8 Hz, 1H), 9.30 (brs, 1H), 9.92 (brs, 1H) EI-MS m/z=216 (M$^+$)

Process 2

Substantially the same procedure as in Process 3 of Example 23 was repeated using 6-acetamido-1-methylindole-3-carboxaldehyde (51 mg) obtained in the above Process 1 and Compound IIc-1 (245 mg) obtained in Process 2 of Example 13 to give Compound 38 (52 mg).

$^1$H-NMR (270 MHz, DMSO-d$_6$) δ2.09 (s, 3H), 3.77 (s, 3H), 3.80 (s, 3H), 3.92 (s, 6H), 7.29 (dd, J=8.4, 1.5 Hz, 1H), 7.35 (s, 2H), 7.55 (d, J=15.3 Hz, 1H), 7.95 (d, J=15.3 Hz, 1H), 7.98 (d, J=8.4 Hz, 1H), 8.01 (d, J=1.5 Hz, 1H), 8.02 (s, 1H), 10.03 (s, 1H) EI-MS m/z=408 (M$^+$)

EXAMPLE 39

(E)-3-(6-Methoxyindol-3-yl)-1-(3,4,5-trimethoxyphenyl)-2-propen-1-one (Compound 39)

Substantially the same procedure as in Example 1 was repeated using 3',4',5'-trimethoxyacetophenone (659 mg) and 6-methoxyindole-3-carboxaldehyde (550 mg) except that the reaction solution was concentrated under reduced pressure, that the residue was purified by silica gel column chromatography, and that the obtained crude crystals were recrystallized from ethanol, to give Compound 39 (369 mg).

$^1$H-NMR (270 MHz, CDCl$_3$) δ3.88 (s, 3H), 3.94 (s, 3H), 3.97 (s, 6H), 6.96 (m, 2H), 7.30 (s, 2H), 7.48 (d, J=15.4 Hz, 1H), 7.53 (s, 1H), 7.86 (d, J=8.9 Hz, 1H), 8.05 (d, J=15.4 Hz, 1H), 8.52 (brs, 1H) EI-MS m/z=367 (M$^+$)

EXAMPLE 40

(E)-3-(6,7-Dimethoxyindol-3-yl)-1-(3,4,5-trimethoxy-phenyl)-2-propen-1-one (Compound 40)
Process 1

Substantially the same procedure as in Process 1 of Example 15 was repeated using 6,7-dimethoxyindole (590 mg) to give 6,7-dimethoxyindole-3-carboxaldehyde (577 mg).

$^1$H-NMR (90 MHz, CDCl$_3$) δ3.94 (s, 3H), 4.02 (s, 3H), 7.00 (d, J=8.5 Hz, 1H), 7.74 (d, J=3.1 Hz, 1H), 7.93 (d, J=8.5 Hz, 1H), 8.95 (brs, 1H), 10.00 (s, 1H) EI-MS m/z=205 (M$^+$)
Process 2

Substantially the same procedure as in Example 1 was repeated using 3',4',5'-trimethoxyacetophenone (525 mg) and 6,7-dimethoxyindole-3-carboxaldehyde obtained in the above Process 1 except that water was added to the reaction solution, that the precipitated crystals were collected by filtration, and that the obtained crude crystals were recrystallized from ethanol, to give Compound 40 (586 mg).

$^1$H-NMR (270 MHz, CDCl$_3$) δ3.94 (s, 3H), 3.95 (s, 3H), 3.97 (s, 6H), 4.04 (s, 3H), 7.02 (d, J=8.7 Hz, 1H), 7.30 (s, 2H), 7.46 (d, J=15.6 Hz, 1H), 7.55 (d, J=3.0 Hz, 1H), 7.62 (d, J=8.7 Hz, 1H), 8.04 (d, J=15.6 Hz, 1H), 8.71 (s, 1H) EI-MS m/z 397 (M$^+$)

EXAMPLE 41

(E)-3-(6-Hydroxy-7-methoxyindol-3-yl)-1-(3,4,5-trimethoxyphenyl)-2-propen-1-one (Compound 41)
Process 1

Substantially the same procedure as in Process 1 of Example 15 was repeated using 6-benzyloxy-7-methoxyindole (3.2 g) to give 6-benzyloxy-7-methoxyindole-3-carboxaldehyde (3.42 g).

$^1$H-NMR (90 MHz, CDCl$_3$) δ4.04 (s, 3H), 5.17 (s, 2H), 7.00 (d, J=8.5 Hz, 1H), 7.39 (m, 5H), 7.75 (d, J=2.8 Hz, 1H), 7.89 (d, J=8.5 Hz, 1H), 8.85 (brs, 1H), 10.00 (s, 1H) EI-MS m/z=281 (M$^+$)
Process 2

Substantially the same procedure as in Process 2 of Example 27 was repeated using 6-benzyloxy-7-methoxyindole-3-carboxaldehyde (1.41 g) obtained in the above Process 1 to give 6-hydroxy-7-methoxyindole-3-carboxaldehyde (0.47 g).

$^1$H-NMR (90 MHz, DMSO-d$_6$) δ3.88 (s, 3H), 6.79 (d, J=8.4 Hz, 1H), 7.58 (d, J=8.4 Hz, 1H), 7.99 (s, 1H), 9.06 (s, 1H), 9.84 (s, 1H), 11.94 (s, 1H) EI-MS m/z=191 (M$^+$)
Process 3

Substantially the same procedure as in Example 1 was repeated using 3',4',5'-trimethoxyacetophenone (420 mg) and 6-hydroxy-7-methoxyindole-3-carboxaldehyde (382 mg) obtained in the above Process 2 except that the reaction solution was concentrated under reduced pressure, that the residue was purified by silica gel column chromatography, and that the obtained crude crystals were recrystallized from ethyl acetate and then from a mixed solvent of ethanol and water, to give Compound 41 (214 mg).

$^1$H-NMR (270 MHz, CDCl$_3$) δ3.92 (s, 3H), 3.96 (s, 6H), 4.01 (s, 3H), 6.94 (d, J=8.4 Hz, 1H), 7.40 (s, 2H), 7 41 (d, J=15.5 Hz, 1H), 7.50 (d, J=8.4 Hz, 1H), 7.53 (d, J=3.0 Hz, 1H), 8.03 (d, J=15.5 Hz, 1H), 8.14 (s, 1H), 10.72 (s, 1H) EI-MS m/z=383 (M$^+$)

EXAMPLE 42

(E)-3-(6-Chloroindol-3-yl)-1-(3,4,5-trimethoxyphenyl)-2-propen-1-one (Compound 42)

Substantially the same procedure as in Example 1 was repeated using 3',4',5'-trimethoxyacetophenone (2.1 g) and 6-chloroindole-3-carboxaldehyde (1.8 g) except that the obtained product was recrystallized from ethyl acetate, to give Compound 42 (2.57 g).

$^1$H-NMR (270 MHz, DMSO-d$_6$) δ3.77 (s, 3H), 3.91 (s, 6H), 7.21 (dd, J=8.7, 1.8 Hz, 1H), 7.37 (s, 2H), 7.53 (d, J=1.8 Hz, 1H), 7.62 (d, J=15.8 Hz, 1H), 8.01 (d, J=15.8 Hz, 1H), 8.07 (d, J=8.7 Hz, 1H), 8.17 (s, 1H), 11.98 (s, 1H) EI-MS m/z=371, 373 (M$^+$)

EXAMPLE 43

(E) -3-(7-Methylindol-3-yl)-1-(3,4,5-trimethoxyphenyl)-2-propen-1-one (Compound 43)
Process 1

Substantially the same procedure as in Process 1 of Example 15 was repeated using 7-methylindole (500 mg) to give 7-methylindole-3-carboxaldehyde (595 mg).

$^1$H-NMR (90 MHz, CDCl$_3$) δ2.52 (s, 3H), 7.15–7.30 (m, 2H), 7.89 (s, 1H), 8.15 (dd, J=7.5, 1.5 Hz, 1H), 8.80 (brs, 1H), 10.06 (s, 1H) EI-MS m/z=159 (M$^+$)
Process 2

Substantially the same procedure as in Example 12 was repeated using 3',4',5'-trimethoxyacetophenone (630 mg) and 7-methylindole-3-carboxaldehyde (480 mg) obtained in the above Process 1 to give Compound 43 (610 mg).

$^1$H-NMR (270 MHz, CDCl$_3$) δ2.54 (s, 3H), 3.94 (s, 3H), 3.97 (s, 6H), 7.13 (d, J=7.4 Hz, 1H), 7.22 (t, J=7.4 Hz, 1H), 7.31 (s, 2H), 7.53 (d, J=15.8 Hz, 1H), 7.64 (d, J=2.5 Hz, 1H), 7.85 (d, J=7.4 Hz, 1H), 8.10 (d, J=15.8 Hz, 1H), 8.58 (brs, 1H) EI-MS m/z=351 (M$^+$)

EXAMPLE 44

(E)-3-(7-Nitroindol-3-yl)-1-(3,4,5-trimethoxyphenyl)-2-propen-1-one (Compound 44)

Substantially the same procedure as in Example 1 was repeated using 3',4',5'-trimethoxyacetophenone (630 mg) and 7-nitroindole-3-carboxaldehyde (552 mg) to give Compound 44 (491 mg).

$^1$H-NMR (270 MHz, CDCl$_3$) δ3.94 (s, 3H), 3.98 (s, 6H), 7.37 (s, 1H), 7.38 (t, J=7.9 Hz, 1H), 7.53 (d, J=15.8 Hz, 1H), 7.90 (d, J=3.0 Hz, 1H), 8.10 (d, J=15.8 Hz, 1H), 8.25 (d, J=7.9 Hz, 1H), 8.10 (d, J=7.9 Hz, 1H), 11.56 (brs, 1H) EI-MS m/z=382 (M$^+$)

EXAMPLE 45

(E)-3-(7-Nitro-1-methylindol-3-yl)-1-(3,4,5-trimethoxy-phenyl)-2-propen-1-one (Compound 45)

Substantially the same procedure as in Example 2 was repeated using Compound 44 (435 mg) obtained in Example 44 except that insoluble matters were filtered off, that the resulting filtrate was concentrated under reduced pressure, that water was added thereto, and that the precipitated crystals were collected by filtration, to give Compound 45 (417 mg).

$^1$H-NMR (270 MHz, CDCl$_3$) δ3.91 (s, 3H), 3.95 (s, 3H), 3.97 (s, 6H), 7.29 (s, 2H), 7.33 (t, J=7.9 Hz, 1H), 7.46 (d, J=15.5 Hz, 1H), 7.59 (s, 1H), 7.89 (d, J=7.9 Hz, 1H), 8.05 (d, J=15.5 Hz, 1H), 8.20 (d, J=7.9 Hz, 1H) EI-MS m/z=396 (M$^+$)

EXAMPLE 46

(E)-3-(7-Methoxyindol-3-yl)-1-(3,4,5-trimethoxyphenyl)-2-propen-1-one (Compound 46)

Substantially the same procedure as in Example 39 was repeated using 3',4',5'-trimethoxyacetophenone (1.74 g) and 7-methoxyindole-3-carboxaldehyde (1.45 g) to give Compound 46 (1.47 g).

$^1$H-NMR (270 MHz, CDCl$_3$) δ3.94 (s, 3H), 3.97 (s, 6H), 3.99 (s, 3H), 6.77 (d, J=7.9 Hz, 1H), 7.23 (t, J=7.9 Hz, 1H), 7.31 (s, 2H), 7.51 (d, J=15.5 Hz, 1H), 7.58 (d, J=7.9 Hz, 1H), 7.59 (d, J=2.5 Hz, 1H), 8.09 (d, J=15.5 Hz, 1H), 8.79 (brs, 1H) EI-MS m/z=367 (M$^+$)

EXAMPLE 47

(E)-3-(1-Benzylindol-3-yl)-1-(3,4,5-trimethoxyphenyl)-2-propen-1-one (Compound 47)

Substantially the same procedure as in Example 3 was repeated using Compound 1 (2.37 g) obtained in Example 1 and benzyl bromide (1.8 g) except that the obtained crude crystals were recrystallized from ethanol and then from a mixed solvent of ethyl acetate and hexane, to give Compound 47 (2.11 g).

$^1$H-NMR (270 MHz, CDCl$_3$) δ3.94 (s, 3H), 3.96 (s, 6H), 5.35 (s, 2H), 7.15 (m, 2H), 7.22–7.39 (m, 8H), 7.49 (d, J=15.5 Hz, 1H), 7.55 (s, 1H), 7.99 (m, 1H), 8.08 (d, J=15.5 Hz, 1H) EI-MS m/z=427 (M$^+$)

EXAMPLE 48

(E)-3-(Indol-3-yl)-2-methyl-1-(3,4,5-trimethoxyphenyl)-2-propen-1-one (Compound 48)
Process 1

3,4,5-Trimethoxybenzaldehyde (3.92 g) was dissolved in tetrahydrofuran (100 ml), and ethylmagnesium bromide (1M tetrahydrofuran solution, 22 ml) was added thereto under ice-cooling. A 10% aqueous solution of citric acid was added to the reaction solution, and the mixture was extracted with ethyl acetate. The organic layer was washed with water and then with a saturated saline, dried over magnesium sulfate, and concentrated under reduced pressure. The residue was dissolved in acetone (100 ml), and Jones' reagent was added thereto under ice-cooling, followed by stirring for 30 minutes. 2-Propanol (10 ml) was added to the reaction solution, and the solution was then concentrated under reduced pressure, followed by partitioning between ethyl acetate and water. The organic layer was washed with water and then a saturated saline, dried over magnesium sulfate, and concentrated under reduced pressure. The residue was purified by silica gel column chromatography to give 3,'4',5'-trimethoxypropiophenone (2.3 g).

$^1$H-NMR (90 MHz, CDCl$_3$) δ1.23 (t, J=7.2 Hz, 3H), 2.97 (q, J=7.2 Hz, 2H), 3.92 (s, 9H), 7.22 (s, 2H) EI-MS m/z=224 (M$^+$)
Process 2

Substantially the same procedure as in Example 1 was repeated using 3',4',5'-trimethoxypropiophenone (1.12 g) obtained in the above Process 1 and indole-3-carboxaldehyde (0.73 g) except that the obtained crystals were recrystallized from a mixed solvent of ethanol, acetone, ethyl acetate, N,N-dimethylformamide and water, to give Compound 48 (0.81 g).

$^1$H-NMR (270 MHz, DMSO-d$_6$) δ2.23 (s, 3H), 3.79 (s, 3H), 3.82 (s, 6H), 6.96 (s, 2H), 7.11 (m, 1H), 7.19 (m, 1H), 7.47 (m, 2H), 7.64 (s, 1H), 7.89 (s, 1H), 11.90 (s, 1H) EI-MS m/z=351 (M$^+$)

EXAMPLE 49

(E)-3-(Indol-3-yl)-2-propyl-1-(3,4,5-trimethoxyphenyl)-2-propen-1-one (Compound 49)
Process 1

Substantially the same procedure as in Process 1 of Example 48 was repeated using 3,4,5-trimethoxybenzaldehyde (3.92 g) and butyl lithium (1.56M hexane solution, 15 ml) to give 1-(3,4,5-trimethoxyphenyl)-1-pentanone (2.84 g).

$^1$H-NMR (90 MHz, CDCl$_3$) δ0.96 (t, J=6.3 Hz, 3H), 1.20–1.90 (m, 4H), 2.93 (t, J=7.0 Hz, 2H), 3.92 (s, 9H), 7.20 (s, 2H) EI-MS m/z=252 (M$^+$)
Process 2

Substantially the same procedure as in Example 1 was repeated using 1-(3,4,5-trimethoxyphenyl)-1-pentanone (1.26 g) obtained in the above Process 1 and indole-3-carboxaldehyde (0.73 g) except that water was added to the reaction solution, that the precipitated crystals were collected by filtration, and that the obtained crude crystals were recrystallized from a mixed solvent of ethanol and water, to give Compound 49 (0.51 g).

$^1$H-NMR (270 MHz, DMSO-d$_6$) δ1.04 (t, J=7.6 Hz, 3H), 1.60 (m, 2H), 2.71 (t, J=7.6 Hz, 2H), 3.79 (s, 3H), 3.81 (s, 6H), 6.96 (s, 2H), 7.09 (m, 1H), 7.18 (m, 1H), 7.42 (d, J=6.4 Hz, 1H), 7.48 (d, J=7.9 Hz, 1H), 7.53 (s, 1H), 7.77 (d, J=2.5 Hz, 1H), 11.81 (s, 1H) EI-MS m/z=379 (M$^+$)

EXAMPLE 50

(E)-3-[1-(4-Methylbenzoyl)indol-3-yl]-1-(3,4,5-trimethoxyphenyl)-2-propen-1-one (Compound 50)
Process 1

4-Methylbenzoic acid (2.72 g) and triethylamine (2.53 g) were suspended in dichloromethane (50 ml), and a dichloromethane solution (10 ml) of thionyl chloride (1.19 g) was added thereto, followed by stirring for one hour. The reaction solution was diluted with dichloromethane, and washed with a 10% aqueous solution of citric acid. The organic layer was dried over anhydrous magnesium sulfate, and concentrated under reduced pressure to give acid anhydride (2.50 g).

IR (KBr tablet) 1780, 1720 cm$^{-1}$ EI-MS m/z=254 (M$^+$)
Process 2

Substantially the same procedure as in Example 3 was repeated using Compound 1 (1.35 g) obtained in Example 1 and the acid anhydride (2.03 g) obtained in the above Process 1 except that the reaction product was purified by silica gel column chromatography, and that the obtained crude crystals were recrystallized from a mixed solvent of ethanol and acetone, to give Compound 50 (1.48 g)

$^1$H-NMR (270 MHz, CDCl$_3$) δ2.50 (s, 3H), 3.95 (s, 3H), 3.96 (s, 6H), 7.28 (s, 2H), 7.38 (d, J=7.9 Hz, 2H), 7.47 (m, 2H), 7.59 (d, J=15.8 Hz, 1H), 7.68 (d, J=7.9 Hz, 2H), 7.73 (s, 1H), 7.92 (d, J=15.8 Hz, 1H), 7.92 (m, 1H), 8.41 (m, 1H) EI-MS m/z=455 (M$^+$)

EXAMPLE 51

(E)-3-[1-(4-Methoxybenzoyl)indol-3-yl]-1-(3,4,5-trimethoxyphenyl)-2-propen-1-one (Compound 51)

Process 1

Substantially the same procedure as in Process 1 of Example 50 was repeated using 4-methoxybenzoic acid (3.04 g) to give an acid anhydride (2.87 g).

IR (KBr tablet) 1780, 1720 cm$^{-1}$ EI-MS m/z=286 (M$^+$)

Process 2

Substantially the same procedure as in Example 3 was repeated using Compound 1 (1.35 g) obtained in Example 1 and the acid anhydride (2.29 g) obtained in the above Process 1 except that the reaction product was purified by silica gel column chromatography, and that the obtained crude crystals were recrystallized from ethanol, to give Compound 51 (1.08 g).

$^1$H-NMR (270 MHz, CDCl$_3$) δ3.93 (s, 3H), 3.95 (s, 3H), 3.96 (s, 6H), 7.05 (d, J=8.7 Hz, 2H), 7.29 (s, 2H), 7.45 (m, 2H), 7.70 (d, J=15.6 Hz, 1H), 7.76 (s, 1H), 7.78 (d, J=8.7 Hz, 2H), 7.94 (d, J=15.6 Hz, 1H), 7.97 (m, 1H), 8.35 (m, 1H) EI-MS m/z=471 (M$^+$)

EXAMPLE 52

(E)-3-[1-(3-Methylbenzoyl)indol-3-yl]-1-(3,4,5-trimethoxyphenyl)-2-propen-1-one (Compound 52)

Process 1

Substantially the same procedure as in Process 1 of Example 50 was repeated using 3-methylbenzoic acid (2.72 g) to give an acid anhydride (2.58 g).

IR (KBr tablet) 1780, 1720 cm$^{-1}$ EI-MS m/z=254 (M$^+$)

Process 2

Substantially the same procedure as in Process 2 of Example 51 was repeated using Compound 1 (1.35 g) obtained in Example 1 and the acid anhydride (2.03 g) obtained in the above Process 1 to give Compound 52 (1.65 g).

$^1$H-NMR (270 MHz, CDCl$_3$) δ2.48 (s, 3H), 3.95 (s, 3H), 3.96 (s, 6H), 7.28 (s, 2H), 7.47 (m, 4H), 7.53 (m, 1H), 7.58 (brs, 1H), 7.59 (d, J=15.6 Hz, 1H), 7.70 (s, 1H), 7.91 (d, J=15.6 Hz, 1H), 7.97 (m, 1H), 8.43 (m, 1H) EI-MS m/z=455 (M$^+$)

EXAMPLE 53

(E)-3-[1-(3-Methoxybenzoyl)indol-3-yl]-1-(3,4,5-trimethoxyphenyl)-2-propen-1-one (Compound 53)

Process 1

Substantially the same procedure as in Process 1 of Example 50 was repeated using 3-methoxybenzoic acid (3.04 g) to give an acid anhydride (2.93 g).

IR (KBr tablet) 1780, 1720 cm$^{-1}$ EI-MS m/z=286 (M$^+$)

Process 2

Substantially the same procedure as in Process 2 of Example 50 was repeated using Compound 1 (1.35 g) obtained in Example 1 and the acid anhydride (2.29 g) obtained in the above Process 1 to give Compound 53 (1.46 g).

$^1$H-NMR (270 MHz, CDCl$_3$) δ3.89 (s, 3H), 3.95 (s, 3H), 3.96 (s, 6H), 7.19 (m, 1H), 7.28 (s, 2H), 7.29 (m, 2H), 7.48 (m, 3H), 7.59 (d, J=15.6 Hz, 1H), 7.72 (s, 1H), 7.91 (d, J=15.6 Hz, 1H), 7.97 (m, 1H), 8.43 (m, 1H) EI-MS m/z=471 (M$^+$)

EXAMPLE 54

(E)-3-[1-(2-Methylbenzoyl)indol-3-yl]-1-(3,4,5-trimethoxyphenyl)-2-propen-1-one (Compound 54)

Process 1

Substantially the same procedure as in Process 1 of Example 50 was repeated using 2-methylbenzoic acid (2.72 g) to give an acid anhydride (2.55 g).

IR (KBr tablet) 1780, 1720 cm$^{-1}$ EI-MS m/z=254 (M$^+$)

Process 2

Substantially the same procedure as in Process 2 of Example 50 was repeated using Compound 1 (1.35 g) obtained in Example 1 and the acid anhydride (2.03 g) obtained in the above Process 1 to give Compound 54 (1.45 g).

$^1$H-NMR (270 MHz, CDCl$_3$) δ2.37 (s, 3H), 3.94 (s, 3H), 3.95 (s, 6H), 7.27 (s, 2H), 7.33–7.51 (m, 7H), 7.56 (d, J=15.8 Hz, 1H), 7.85 (d, J=15.8 Hz, 1H), 7.95 (m, 1H), 8.41 (m, 1H) EI-MS m/z=455 (M$^+$)

EXAMPLE 55

(E)-3-[1-(2-Methoxybenzoyl)indol-3-yl]-1-(3,4,5-trimethoxyphenyl)-2-propen-1-one (Compound 55)

Process 1

Substantially the same procedure as in Process 1 of Example 50 was repeated using 2-methoxybenzoic acid (3.04 g) to give an acid anhydride (2.90 g).

IR (KBr tablet) 1780, 1720 cm$^{-1}$ EI-MS m/z=286 (M$^+$)

Process 2

Substantially the same procedure as in Process 2 of Example 50 was repeated using Compound 1 (1.35 g) obtained in Example 1 and the acid anhydride (2.29 g) obtained in the above Process 1 to give Compound 55 (0.98 g)

$^1$H-NMR (270 MHz, CDCl$_3$) δ3.80 (s, 3H), 3.94 (s, 3H), 3.95 (s, 6H), 7.07 (d, J=8.4 Hz, 1H), 7.13 (td, J=7.5, 1.0 Hz, 1H), 7.27 (s, 2H), 7.45 (s, 1H), 7.48 (m, 3H), 7.56 (d, J=15.8 Hz, 1H), 7.57 (m, 1H), 7.86 (d, J=15.8 Hz, 1H), 7.94 (m, 1H), 8.50 m, 1H) EI-MS m/z=471 (M$^+$)

EXAMPLE 56

(E)-3-[1-(4-Acetamidobenzoyl)indol-3-yl]-1-(3,4,5-trimethoxyphenyl)-2-propen-1-one (Compound 56)

Process 1

4-Acetamidobenzoic acid (2.15 g) was dissolved in a mixed solvent of dichloromethane (10 ml) and tetrahydrofuran (10 ml), and thionyl chloride (1.43 g) and pyridine (20 mg) were added thereto, followed by heating under reflux for one hour. After the reaction solution was cooled, the solution was poured into a tetrahydrofuran solution (5 ml) of p-nitrophenol (1.39 g), which was separately prepared, under ice-cooling. Triethylamine (2.43 g) was further added to the mixture, followed by stirring for 14 hours. The reaction solution was diluted with chloroform, and washed with a 10% aqueous solution of citric acid. The crystals precipitated in the organic layer were collected by filtration to give an activated ester (2.41 g).

$^1$H-NMR (90 MHz, DMSO-d$_6$) δ2.12 (s, 3H), 7.57 (d, J=9.1 Hz, 2H), 7.79 (d, J=8.9 Hz, 2H), 8.09 (d, J=8.9 Hz, 2H), 8.32 (d, J=9.1 Hz, 2H), 10.33 (s, 1H) EI-MS m/z=300 (M$^+$)

Process 2

Substantially the same procedure as in Process 2 of Example 50 was repeated using Compound 1 (1.35 g) obtained in Example 1 and the activated ester (2.40 g) obtained in the above Process 1 to give Compound 56 (1.37 g).

$^1$H-NMR (270 MHz, CDCl$_3$) δ2.26 (s, 3H), 3.95 (s, 3H), 3.96 (s, 6H), 7.29 (s, 2H), 7.47 (m, 2H), 7.56 (s, 1H), 7.59 (d, J=15.8 Hz, 1H), 7.732 (d, J=9.2 Hz, 2H), 7.733 (s, 1H), 7.78 (d, J=9.2 Hz, 2H), 7.93 (d, J=15.8 Hz, 1H), 7.97 (m, 1H), 8.37 (m, 1H) FAB-MS m/z=499 (M$^+$+1)

EXAMPLE 57

(E)-3-[1-(4-Dimethylaminobenzoyl)indol-3-yl]-1-(3, 4,5-trimethoxyphenyl)-2-propen-1-one (Compound 57)

Process 1

Substantially the same procedure as in Process 1 of Example 56 was repeated using 4-dimethylaminobenzoic acid (2.15 g) except that the crystals were not precipitated to give a chloroform solution of an activated ester.

Process 2

Substantially the same procedure as in Process 2 of Example 50 was repeated using Compound 1 (3.38 g) obtained in Example 1 and the chloroform solution of an activated ester obtained in the above Process 1, to give Compound 57 (2.95 g).

$^1$H-NMR (270 MHz, CDCl$_3$) δ3.12 (S, 6H), 3.95 (s, 3H), 3.97 (s, 6H), 6.75 (d, J=8.9 Hz, 2H), 7.30 (s, 2H), 7.43 (m, 2H), 7.59 (d, J=15.6 Hz, 1H), 7.74 (d, J=8.9 Hz, 2H), 7.86 (s, 1H), 7.97 (m, 1H), 7.98 (d, J=15.6 Hz, 1H), 8.29 (m, 1H) EI-MS m/z=484 (M$^+$)

EXAMPLE 58

(E)-3-[1-(3,4-Dimethoxybenzoyl)indol-3-yl]-1-(3,4, 5-trimethoxyphenyl)-2-propen-1-one (Compound 58)

Process 1

Substantially the same procedure as in Process 1 of Example 56 was repeated using 3,4-dimethoxybenzoic acid (1.39 g) except that the crystals were not precipitated and that the organic layer was concentrated under reduced pressure, to give an activated ester (3.30 g).

$^1$H-NMR (90 MHz, CDCl$_3$) δ3.97 (s, 3H), 3.98 (s, 3H), 6.97 (d, J=8.5 Hz, 1H), 7.40 (d, J=9.0 Hz, 2H), 7.65 (d, J=1.9 Hz, 1H), 7.87 (dd, J=8.5, 1.9 Hz, 1H), 8.32 (d, J=9.0 Hz, 2H) EI-MS m/z=303 (M$^+$)

Process 2

Substantially the same procedure as in Process 2 of Example 50 was repeated using Compound 1 (1.69 g) obtained in Example 1 and the activated ester obtained in the above Process 1 to give Compound 58 (0.53 g).

$^1$H-NMR (270 MHz, CDCl$_3$) δ3.95 (s, 3H), 3.97 (s, 9H), 4.01 (s, 3H), 7.00 (d, J=8.9 Hz, 1H), 7.29 (s, 2H), 7.38 (m, 2H), 7.47 (m, 2H), 7.61 (d, J=15.5 Hz, 1H), 7.81 (s, 1H), 7.95 (d, J=15.5 Hz, 1H), 7.97 (m, 1H), 8.35 (m, 1H) EI-MS m/z=501 (M$^+$)

EXAMPLE 59

(E)-3-[1-(3,4,5-Trimethoxybenzoyl)indol-3-yl]-1-(3, 4,5-trimethoxyphenyl)-2-propen-1-one (Compound 59)

Substantially the same procedure as in Example 3 was repeated using Compound 1 (1.69 g) obtained in Example 1 and 3,4,5-trimethoxybenzoyl chloride (2.31 g) except that the obtained crude crystals were recrystallized from a mixed solvent of ethanol and acetone, to give Compound 59 (1.22)

$^1$H-NMR (270 MHz, CDCl$_3$) δ3.91 (s, 6H), 3.95 (s, 3H), 3.96 (s, 6H), 3.97 (s, 3H), 7.00 (s, 2H), 7.29 (s, 2H), 7.48 (m, 2H), 7.61 (d, J=15.8 Hz, 1H), 7.78 (s, 1H), 7.94 (d, J=15.8 Hz, 1H), 7.99 (m, 1H), 8.37 (m, 1H) EI-MS m/z=531 (M$^+$)

EXAMPLE 60

(E)-3-(1-Nicotinoylindol-3-yl)-1-(3,4,5-trimethoxyphenyl)-2-propen-1-one (Compound 60)

Substantially the same procedure as in Example 59 was repeated using Compound 1 (1.43 g) obtained in Example 1 and nicotinoyl chloride hydrochloride (1.51 g) to give Compound 60 (0.37 g).

$^1$H-NMR (270 MHz, CDCl$_3$) δ3.95 (s, 3H), 3.96 (s, 6H), 7.28 (s, 2H), 7.47–7.66 (m, 5H), 7.90 (d, J=15.8 Hz, 1H), 7.98 (m, 1H), 8.14 (brd, J=7.9 Hz, 1H), 8.46 (m, 1H), 8.91 (brd, J=4.6 Hz, 1H), 9.03 (d, J=2.0 Hz, 1H) FAB-MS m/z=443 (M$^+$+1)

EXAMPLE 61

(E)-3-(1-Isonicotinoylindol-3-yl)-1-(3,4,5-trimethoxy-phenyl)-2-propen-1-one (Compound 61)

Substantially the same procedure as in Example 59 was repeated using Compound 1 (1.43 g) obtained in Example 1 and isonicotinoyl chloride hydrochloride (1.51 g) to give Compound 61 (0.48 g).

$^1$H-NMR (270 MHz, CDCl$_3$) δ3.95 (s, 3H), 3.96 (s, 6H), 7.28 (s, 2H), 7.47–7.65 (m, 6H), 7.89 (d, J=15.5 Hz, 1H), 7.98 (m, 1H), 8.46 (m, 1H), 8.91 (m, 2H) FAB-MS m/z=443 (M$^+$+1)

EXAMPLE 62

(E)-2-Ethyl-3-(indol-3-yl)-1-(3,4,5-trimethoxyphenyl)-2-propen-1-one (Compound 62)

Process 1

Substantially the same procedure as in Process 1 of Example 48 was repeated using 3,4,5-trimethoxybenzaldehyde (43.12 g) and propylmagnesium bromide (1.0 M tetrahydrofuran solution, 330 ml) to give 1-(3,4,5-trimethoxyphenyl)-1-butanone (17.43 g).

$^1$H-NMR (90 MHz, CDCl$_3$) δ1.01 (t, J=7.2 Hz, 3H), 1.77 (m, 2H), 2.91 (t, J=7.2 Hz, 2H), 3.92 (s, 9H), 7.22 (s, 2H) EI-MS m/z=238 (M$^+$)

Process 2

Substantially the same procedure as in Example 1 was repeated using 1-(3,4,5-trimethoxyphenyl)-1-butanone (1.90 g) obtained in the above Process 1 and indole-3-carboxaldehyde (1.16 g) except that the reaction solution was concentrated under reduced pressure, that the residue was purified by silica gel column chromatography, and that the obtained crude crystals were recrystallized from ethanol, to give Compound 62 (0.88 g).

$^1$H-NMR (270 MHz, CDCl$_3$) δ1.27 (t, J=7.4 Hz, 3H), 2.83 (q, J=7.4 Hz, 2H), 3.90 (s, 6H), 3.95 (s, 3H), 7.03 (s, 2H), 7.22 (m, 1H), 7.28 (m, 1H), 7.44 (d, J=8.4 Hz, 1H), 7.54 (d, J=7.4 Hz, 1H), 7.57 (s, 1H), 7.63 (d, J=3.0 Hz, 1H), 8.62 (s, 1H) EI-MS m/z=365 (M$^+$)

EXAMPLE 63

(E)-2-Methyl-3-(6-methylindol-3-yl)-1-(3,4,5-trimethoxyphenyl)-2-propen-1-one (Compound 63)

Substantially the same procedure as in Example 1 was repeated using 3,4,5-trimethoxypropiophenone (0.67 g)

obtained in Process 1 of Example 48 and 6-methylindole-3-carboxaldehyde (0.48 g) obtained in Process 1 of Example 32 except that the reaction solution was concentrated under reduced pressure, that the residue was purified by silica gel column chromatography, and that the obtained crude crystals were recrystallized from a mixed solvent of hexane and ethyl acetate, and then from ethanol, to give Compound 62 (0.17 g).

$^1$H-NMR (270 MHz, CDCl$_3$) δ2.30 (d, J=1.0 Hz, 3H), 2.47 (s, 3H), 3.89 (s, 6H), 3.95 (s, 3H), 7.021 (s, 2H), 7.024 (brd, J=8.2 Hz, 1H), 7.22 (s, 1H), 7.45 (d, J=8.2 Hz, 1H), 7.56 (d, J=2.5 Hz, 1H), 7.66 (s, 1H), 8.53 (s, 1H) EI-MS M/z=365 (M$^+$)

EXAMPLE 64

3-(Indol-3-yl)-2-phenyl-1-(3,4,5-trimethoxyphenyl)-2-propen-1-one (Compound 64)

Process 1

Substantially the same procedure as in Process 1 of Example 48 was repeated using 3,4,5-trimethoxybenzaldehyde (3.92 g) and benzylmagnesium bromide (2.0 M diethyl ether solution, 23 ml) to give 3,4,5-trimethoxydeoxybenzoin (3.51 g).

$^1$H-NMR (90 MHz, CDCl$_3$) δ3.84 (s, 6H), 3.89 (s, 3H), 4.22 (s, 2H), 7.25 (s, 7H) EI-MS m/z=286 (M$^+$)

Process 2

Substantially the same procedure as in Example 1 was repeated using 3,4,5-trimethoxydeoxybenzoin (1.43 g) obtained in the above Process 1 and indole-3-carboxyaldehdye (0.73 g) except that the reaction solution was concentrated under reduced pressure, that the residue was purified by silica gel column chromatography, and that the obtained crude product was further purified by preparative medium-pressure silica gel column chromatography, to give Compound 64 (0.89 g).

EI-MS m/z=413 (M$^+$)

EXAMPLE 65

(E)-2-Butyl-3-(indol-3-yl)-1(3,4,5-trimethoxyphenyl)-2-propen-1-one (Compound 65)

Process 1

Substantially the same procedure as in Process 1 of Example 48 was repeated using 3,4,5-trimethoxybenzaldehyde (3.92 g) and pentylmagnesium bromide (2.0 M diethyl ether solution, 12 ml) to give 1-(3,4,5 -trimethoxyphenyl)-1-hexanone (3.27 g).

$^1$H-NMR (90 MHz, CDCl$_3$) δ0.92 (t, J=5.9 Hz, 3H), 1.34 (m, 4H), 1.74 (m, 2H), 2.92 (t, J=7.2 Hz, 2H), 3.91 (s, 9H), 7.22 (s, 2H) EI-MS m/z=266 (M$^+$)

Process 2

Substantially the same procedure as in Example 1 was repeated using 1-(3,4,5-trimethoxyphenyl)-1-hexanone (2.66 g) obtained in the above Process 1 and indole-3-carboxaldehyde (1.45 g) except that the reaction solution was concentrated under reduced pressure, that the residue was purified by silica gel column chromatography, and that the obtained crude crystals were recrystallized from ethyl acetate, to give Compound 65 (0.33 g).

$^1$H-NMR (270 MHz, CDCl$_3$) δ0.97 (m, 3H), 1.53 (m, 2H), 1.63 (m, 2H), 2.81 (t, J=7.7 Hz, 2H), 3.89 (s, 6H), 3.95 (s, 3H), 7.04 (s, 2H), 7.18 (m, 1H), 7.27 (m, 1H), 7.43 (d, J=8.4 Hz, 1H), 7.54 (d, J=8.4 Hz, 1H), 7.56 (s, 1H), 7.59 (d, J=2.9 Hz, 1H), 8.69 (s, 1H) EI-MS m/z=393 (M$^+$)

EXAMPLE 66

(E)-3-(6-Ethylindol-3-yl)-2-methyl-1-(3,4,5-trimethoxy-phenyl)-2-propen-1-one (Compound 66)

Process 1

6-Hydroxymethyl-1-toluenesulfonylindole (2.50 g) was dissolved in ethyl acetate (240 ml), and manganese dioxide (24 g) was added thereto, followed by stirring at room temperature for 24 hours. Manganese dioxide was filtered off and the filtrate was concentrated under reduced pressure. The residue was dissolved in tetrahydrofuran (100 ml), the resultant solution was cooled to −78° C., and a pentane solution of methyllithium (1M solution, 10 ml) was added thereto. One hour after, acetic anhydride (1 ml) was added to the solution at the same temperature, followed by partitioning between ethyl acetate and water. The organic layer was dried over anhydrous magnesium sulfate and concentrated under reduced pressure. The residue was dissolved in acetic acid (10 ml), and 10% palladium on carbon (1.63 g) was added thereto, followed by stirring at room temperature for 48 hours under an atmosphere of hydrogen. The catalyst was filtered off, the filtrate was concentrated under reduced pressure, and the residue was purified by silica gel column chromatography to give Compound (XIV) (0.78 g).

$^1$H-NMR (90 MHz, CDCl$_3$) δ1.24 (t, J=7.5 Hz, 3H), 2.36 (s, 3H), 2.65 (t, J=7.5 Hz, 2H), 2.82 (dd, J=8.7, 8.0 Hz, 2H), 3.90 (dd, J=8.7, 8.0 Hz, 2H), 6.78 (d, J=7.8 Hz, 1H), 6.97 (d, J=7.8 Hz, 1H), 7.20 (d, J=8.4 Hz, 2H), 7.49 (s, 1H), 7.67 (d, J=8.4 Hz, 2H) EI-MS m/z=301 (M$^+$)

Process 2

Compound (XIV) (1.12 g) obtained in the above Process 1 was dissolved in chlorobenzene (50 ml), and manganese dioxide (7.72 g) was added thereto, followed by stirring at room temperature for 72 hours. Manganese dioxide was filtered off, and the filtrate was concentrated under reduced pressure. The residue was dissolved in methanol (30 ml), and potassium hydroxide (1.16 g) was added thereto, followed by heating under reflux for 15 hours. The mixture was subjected to partitioning between chloroform and a 10% aqueous solution of citric acid, and the organic layer was concentrated under reduced pressure. Substantially the same procedure as in Process 1 of Example 15 was repeated using the residue to give 6-ethylindole-3-carboxaldehyde (0.22 g).

$^1$H-NMR (90 MHz, CDCl$_3$) δ1.27 (t, J=7.6 Hz, 3H), 2.76 (q, J=7.6 Hz, 2H), 7.11–7.24 (m, 2H), 7.76 (s, 1H), 8.20 (d, J=8.2 Hz, 1H), 8.99 (brs, 1H), 10.01 (s, 1H) EI-MS m/z=173 (M$^+$)

Process 3

Substantially the same procedure as in Example 20 was repeated using 3,4,5-trimethoxypropiophenone (0.42 g) obtained in Process 1 of Example 48 and 6-ethylindole-3-carboxaldehyde (0.37 g) obtained in the above Process 2 to give Compound 66 (0.19 g).

$^1$H-NMR (270 MHz, CDCl$_3$) δ1.29 (t, J=7.5 Hz, 3H), 2.31 (s, 3H), 2.77 (q, J=7.5 Hz, 2H), 3.89 (s, 6H), 3.96 (s, 3H), 7.01 (d, J=8.0 Hz, 1H), 7.02 (s, 2H), 7.25 (s, 1H), 7.48 (d, J=8.0 Hz, 1H), 7.58 (d, J=2.5 Hz, 1H), 7.67 (s, 1H), 8.69 (brs, 1H) EI-MS m/z=379 (M$^+$)

EXAMPLE 67

(E)-3-(1-Diglycolylindol-3-yl)-1-(3,4,5-trimethoxyphenyl)-2-propen-1-one (Compound 67)

Substantially the same procedure as in Example 3 was repeated using Compound 1 (0.17 g) obtained in Example 1 and diglycolic anhydride (0.12 g) except that the obtained crude crystals were washed with ethyl acetate, to give Compound 67 (0.48 g)

$^1$H-NMR (270 MHz, DMSO-d$_6$) δ3.79 (s, 3H), 3.92 (s, 6H), 4.28 (s, 2H), 4.96 (s, 2H), 7.40 (s, 2H), 7.45 (m, 2H), 7.87 (d, J=15.6 Hz, 1H), 7.95 (d, J=15.8 Hz, 1H), 8.14 (m, 1H), 8.32 (m, 1H), 8.62 (s, 1H) EI-MS m/z=453 (M$^+$)

EXAMPLE 68

(E)-3-(6-Isopropylindol-3-yl)-1-(3,4,5-trimethoxyphenyl)-2-propen-1-one (Compound 68)

Process 1

Substantially the same procedure as in Process 1 of Example 15 was repeated using 6-isopropylindole (3.18 g) except that the crystals precipitated in the reaction solution were filtered off, that the filtrate was extracted with ethyl acetate, and that the extract was dried over anhydrous magnesium sulfate and concentrated under reduced pressure, to give 6-isopropylindole-3-carboxaldehyde (0.39 g).

$^1$H-NMR (90 MHz, CDCl$_3$) δ1.31 (d, J=8.7 Hz, 6H), 2.70 (m, 1H), 7.08 (m, 1H), 7.24 (s, 1H), 7.74 (brs, 1H), 8.18 (d, J=9.0 Hz, 1H), 9.28 (s, 1H), 9.97 (s, 1H) EI-MS m/z 187 (M$^+$)

Process 2

Substantially the same procedure as in Process 2 of Example 62 was repeated using 3,4,5-trimethoxyacetophenone (0.42 g) and 6-isopropylindole-3-carboxaldehyde (0.37 g) to give Compound 68 (0.19 g).

$^1$H-NMR (270 MHz, CDCl$_3$) δ1.32 (d, J=6.9 Hz, 6H), 3.05 (m, 1H), 3.95 (s, 3H), 3.96 (s, 6H), 7.22 (dd, J=8.5, 1.5 Hz, 1H), 7.30 (s, 3H), 7.53 (d, J=15.4 Hz, 1H), 7.58 (d, J=2.5 Hz, 1H), 7.92 (d, J=8.5 Hz, 1H), 8.08 (d, J=15.4 Hz, 1H), 8.61 (s, 1H) EI-MS m/z=379 (M$^+$)

EXAMPLE 69

(E)-1-(3,5-Dimethoxyphenyl)-3-(indol-3-yl)-2-propen-1-one (Compound 69)

3',5'-Dimethoxyacetophenone (1.10 g) and indole-3-carboxaldehyde (1.45 g) were dissolved in ethanol (20 ml), and piperidine (0.85 g) was added thereto, followed by heating under reflux for 32 hours. The reaction solution was cooled to room temperature, and the precipitated crystals were collected by filtration, followed by recrystallization from ethanol to give Compound 69 (1.79 g).

$^1$H-NMR (270 MHz, DMSO-d$_6$) δ3.85 (s, 6H), 6.70 (t, J=2.5 Hz, 1H), 7.19 (t, J=2.5 Hz, 2H), 7.21–7.27 (m, 2H), 7.50 (m, 1H) 7.56 (d, J=15.6 Hz, 1H), 8.04 (m, 1H), 8.05 (d, J=15.6 Hz, 1H), 8.14 (d, J=2.5 Hz, 1H), 11.91 (s, 1H) EI-MS m/z=307 (M$^+$) Elemental analysis: C$_{19}$H$_{17}$NO$_3$ Calcd.(%): C, 74.25; H, 5.58; N, 4.56 Found (%): C, 74.15; H, 5.79; N, 4.24

EXAMPLE 70

(E)-1-(4-Hydroxy-3,5-dimethoxyphenyl)-3-(indol-3-yl)-2-propen-1-one (Compound 70)

4'-Hydroxy-3',5'-dimethoxyacetophenone (1.96 g) and indole-3-carboxaldehyde (1.45 g) were dissolved in ethanol (20 ml), and piperidine (0.85 g) was added thereto, followed by heating under reflux for 32 hours. The reaction solution was concentrated under reduced pressure, and the residue was purified by silica gel column chromatography. The obtained crude crystals were recrystallized from ethyl acetate to give Compound 70 (0.62 g).

$^1$H-NMR (270 MHz, DMSO-d$_6$) δ3.91 (s, 6H), 7.19–7.26 (m, 2H), 7.40 (s, 2H), 7.48 (m, 1H), 7.65 (d, J=15.6 Hz, 1H), 8.02 (d, J=15.6 Hz, 1H), 8.05 (m, 1H), 8.11 (d, J=2.5 Hz, 1H), 9.26 (s, 1H), 11.91 (s, 1H) EI-MS m/z=323 (M$^+$) Elemental analysis: C$_{19}$H$_{17}$NO$_4$ Calcd.(%): C, 70.57; H, 5.30; N, 4.33 Found (%): C, 70.56; H, 5.34; N, 4.38

EXAMPLE 71

(E)-1-(4-Benzyloxy-3,5-dimethoxyphenyl)-3-(indol-3-yl)-2-propen-1-one (Compound 71)

4'-Hydroxy-3',5'-dimethoxyacetophenone (1.57 g) and benzyl bromide (1.35 g) were dissolved in acetone (50 ml), and potassium carbonate (1.70 g) was added thereto, followed by heating under reflux for 24 hours. Insoluble matters were filtered off, and the filtrate was concentrated under reduced pressure. The residue was washed with hexane and collected by filtration. The obtained crystals (1.96 g) and indole-3-carboxaldehyde (0.99 g) were dissolved in ethanol (10 ml), and piperidine (0.85 g) was added thereto, followed by heating under reflux for 32 hours. The reaction solution was concentrated under reduced pressure, and the residue was purified by silica gel column chromatography. The obtained crude crystals were recrystallized from a mixed solvent of ethyl acetate and hexane to give Compound 71 (0.17 g).

$^1$H-NMR (270 MHz, DMSO-d$_6$) δ3.92 (s, 6H), 5.03 (s, 2H), 7.21–7.25 (m, 2H), 7.31–7.41 (m, 5H), 7.45–7.52 (m, 3H), 7.63 (d, J=15.3 Hz, 1H), 8.05 (m, 1H), 8.06 (d, J=15.3 Hz, 1H), 8.15 (d, J=3.0Hz, 1H), 11.91 (s, 1H) EI-MS m/z=413 (M$^+$) Elemental analysis: C$_{26}$H$_{23}$NO$_4$ Calcd.(%): C, 75.53; H, 5.61; N, 3.39 Found (%): C, 75.41; H, 5.45; N, 3.38

EXAMPLE 72

3-(Indol-3-yl)-2-methyl-1-(3,4,5-triethoxyphenyl)-2-propen-1-one (Compound 72)

Process 1

3,4,5-Triethoxybenzoic acid (2.54 g) was dissolved in tetrahydrofuran (250 ml), and lithium aluminum hydride (1.20 g) was added thereto, followed by heating under reflux for 24 hours. Ethyl acetate and then a 2N aqueous solution of sodium hydroxide were added to the reaction solution, insoluble matters were filtered off, and the filtrate was concentrated under reduced pressure. The residue was dissolved in ethyl acetate (100 ml), and manganese dioxide (5.10 g) was added thereto, followed by stirring for 120 hours. Insoluble matters were filtered off, and the filtrate was concentrated under reduced pressure. The residue was dissolved in tetrahydrofuran (100 ml), and ethylmagnesium bromide (1M tetrahydrofuran solution, 15 ml) was added thereto, followed by stirring at room temperature for 30 minutes. 1N Hydrochloric acid was added to the reaction solution and the mixture was extracted with ethyl acetate. The organic layer was washed with a saturated saline, dried over anhydrous magnesium sulfate and concentrated under reduced pressure. The residue was dissolved in acetone (100 ml), and Jones' reagent (2 ml) was added thereto under ice-cooling, followed by stirring at the same temperature for 30 minutes. 2-Propanol (10 ml) was added to the reaction solution and the mixture was concentrated under reduced pressure. The residue was subjected to partitioning between ethyl acetate and water. The organic layer was washed with a saturated saline, dried over anhydrous magnesium sulfate and concentrated under reduced pressure. The residue was purified by silica gel column chromatography to give 3',4',5'-triethoxypropiophenone (0.76 g).

$^1$H-NMR (270 MHz, CDCl$_3$) δ1.21 (t, J=7.2 Hz, 3H), 1.37 (t, J=6.9 Hz, 3H), 1.45 (t, J=6.9 Hz, 6H), 2.95 (q, J=7.2 Hz, 2H), 4.12(q, J=6.9 Hz,4H), 4.14 (q, J=6.9 Hz, 2H), 7.21 (s, 2H) EI-MS m/z=266 (M$^+$)

Process 2

3',4',5'-Triethoxypropiophenone (0.67 g) obtained in the above Process 1 and indole-3-carboxaldehyde (0.37 g) were dissolved in ethanol (5 ml), and piperidine (0.43 g) was added thereto, followed by heating under reflux for 32 hours. The reaction solution was concentrated under reduced pressure, and the residue was purified by silica gel column chromatography. The obtained crude crystals were recrystallized from ethanol to give Compound 72 (0.25 g).

¹H-NMR (270 MHz, CDCl₃) δ1.41 (t, J=7.0 Hz, 3H), 1.42 (t, J=7.0 Hz, 6H), 2.31 (d, J=1.0 Hz, 3H), 4.10 (q, J=7.0 Hz, 4H), 4.18(q, J=7.0 Hz, 2H), 7.00 (s, 2H), 7.18 (m, 1H), 7.28 (m, 1H), 7.44 (d, J=7.8 Hz, 1H), 7.57 (d, J=7.9 Hz, 1H), 7.63 (d, J=2.6 Hz, 1H), 7.66 (brs, 1H), 8.71 (brs, 1H) EI-MS m/z=393 (M⁺) Elemental analysis: $C_{24}H_{27}NO_4$ Calcd.(%): C, 73.26; H, 6.92; N, 3.56 Found (%): C, 73.43; H, 7.32; N, 3.54

EXAMPLE 73

1-(4-Ethoxy-3,5-dimethoxyphenyl)-3-(indol-3-yl)-2-methyl-2-propen-1-one (Compound 73)

Process 1

4-Hydroxy-3,5-dimethoxybenzaldehyde (3.64 g) and ethyl iodide (6.24 g) were dissolved in N,N-dimethylformamide (30 ml), and sodium hydride (60% oil dispersion, 1.00 g) was added thereto, followed by stirring at 80° C. for 24 hours. The reaction solution was subjected to partitioning between ethyl acetate and 1N hydrochloric acid. The organic layer was washed successively with a 5% aqueous solution of sodium bicarbonate, water and a saturated saline, dried over anhydrous magnesium sulfate and concentrated under reduced pressure. The residue (3.71 g) was dissolved in tetrahydrofuran (88 ml), and ethylmagnesium bromide (1M tetrahydrofuran solution, 26.5 ml) was added thereto, followed by stirring at room temperature for 30 minutes. 1N Hydrochloric acid was added to the reaction solution and the mixture was extracted with ethyl acetate. The organic layer was washed with a saturated saline, dried over anhydrous magnesium sulfate and concentrated under reduced pressure. The residue was dissolved in acetone (100 ml), and Jones' reagent (5.3 ml) was added thereto under ice-cooling, followed by stirring at the same temperature for 30 minutes. 2-Propanol (5.3 ml) was added to the reaction solution and the mixture was concentrated under reduced pressure. The residue was subjected to partitioning between ethyl acetate and water. The organic layer was washed with a saturated saline, dried over anhydrous magnesium sulfate and concentrated under reduced pressure. The residue was purified by silica gel column chromatography to give 4'-ethoxy-3',5'-dimethoxypropiophenone (3.37 g).

¹H-NMR (90 MHz, CDCl₃) δ1.23 (t, J=7.3 Hz, 3H), 1.34 (t, J=7.0 Hz, 3H), 2.97 (q, J=7.3 Hz, 2H), 3.90 (s, 6H), 4.13 (q, J=7.0 Hz, 2H), 7.22 (s, 2H) EI-MS m/z=238 (M⁺)

Process 2

4'-Ethoxy-3',5'-dimethoxypropiophenone (1.67 g) obtained in the above Process 1 and indole-3-carboxaldehyde (1.02 g) were dissolved in ethanol (14 ml), and piperidine (0.60 g) was added thereto, followed by heating under reflux for 144 hours. The reaction solution was concentrated under reduced pressure, and the residue was purified by silica gel column chromatography. The obtained crude crystals were recrystallized from ethyl acetate to give Compound 73 (1.20 g).

¹H-NMR (270 MHz, CDCl₃) δ1.41 (t, J=7.1 Hz, 3H), 2.31 (d, J=1.0 Hz, 3H), 3.87 (s, 6H), 4.16 (q, J=7.1 Hz, 2H), 7.01 (s, 2H), 7.18 (m, 1H), 7.27 (m, 1H), 7.43 (brd, J=7.9 Hz, 1H), 7.56 (brd, J=7.6 Hz, 1H), 7.63 (d, J=3.0 Hz, 1H), 7.68 (brs, 1H), 8.75 (brs, 1H) EI-MS m/z=365 (M⁺) Elemental analysis: $C_{22}H_{23}NO_4$ Calcd.(%): C, 72.31; H, 6.34; N, 3.83 Found (%): C, 72.44; H, 6.41; N, 3.75

EXAMPLE 74

3-(Indol-3-yl)-1-(4-isobutyloxy-3,5-dimethoxyphenyl)-2-methyl-2-propen-1-one (Compound 74)

Process 1

Substantially the same procedure as in Process 1 of Example 73 was repeated using 4-hydroxy-3,5-dimethoxybenzaldehyde (3.64 g) and isobutyl bromide (5.48 g) to give 4'-isobutyloxy-3',5'-dimethoxypropiophenone (1.92 g).

¹H-NMR (90 MHz, CDCl₃) δ1.02 (d, J=6.8 Hz, 6H), 1.22 (t, J=7.2 Hz, 3H), 2.06 (m, 1H), 2.96 (q, J=7.2 Hz, 2H), 3.81 (d, J=6.6 Hz, 2H), 3.89 (s, 6H), 7.22 (s, 2H) EI-MS m/z=266 (M⁺)

Process 2

4'-Isobutyloxy-3',5'-dimethoxypropiophenone (1.33 g) obtained in the above Process 1 and indole-3-carboxaldehyde (0.73 g) were dissolved in ethanol (10 ml), and piperidine (0.85 g) was added thereto, followed by heating under reflux for 48 hours. The reaction solution was concentrated under reduced pressure, and the residue was purified by silica gel column chromatography. The obtained crude crystals were recrystallized from a mixed solvent of ethyl acetate and hexane to give Compound 74 (0.90 g).

¹H-NMR (270 MHz, CDCl₃) δ1.06 (d, J=6.7 Hz, 6H), 2.11 (m, 1H), 2.31 (d, J=1.0 Hz, 3H), 3.85 (d, J=6.7 Hz, 2H), 3.87 (s, 6H), 7.02 (s, 2H), 7.19 (m, 1H), 7.28 (m, 1H), 7.44 (brd, J=8.2 Hz, 1H), 7.57 (brd, J=7.9 Hz, 1H), 7.64 (d, J=2.6 Hz, 1H), 7.68 (brs, 1H), 8.73 (brs, 1H) EI-MS m/z=393 (M⁺) Elemental analysis: $C_{24}H_{27}NO_4$ Calcd.(%): C, 73.26; H, 6.92; N, 3.56 Found (%): C, 73.20; H, 7.31; N, 3.53

EXAMPLE 75

1-(4-Ethyl-3-dimethoxyphenyl)-3-(indol-3-yl)-2-methyl-2-propen-1-one (Compound 75)

Process 1

3,4,5-Trimethoxybenznitrile (3.86 g) was dissolved in tetrahydrofuran (100 ml), and ethylmagnesium bromide (1M tetrahydrofuran solution, 60 ml) was added thereto, followed by heating under reflux for 12 hours. 1N Hydrochloric acid was added to the reaction solution, and the mixture was stirred at the same temperature for one hour and extracted with ethyl acetate. The organic layer was washed with a saturated saline, dried over anhydrous magnesium sulfate and concentrated under reduced pressure. The residue was purified by silica gel column chromatography to give 4'-ethyl-3',5'-dimethoxypropiophenone (2.37 g).

¹H-NMR (90 MHz, CDCl₃) δ1.08 (t, J=7.3 Hz, 3H), 1.23 (t, J=7.3 Hz, 3H), 2.69 (q, J=7.3 Hz, 2H), 2.97 (q, J=7.3 Hz, 2H), 3.87(s, 6H), 7.15 (s, 2H) EI-MS m/z=222 (M⁺)

Process 2

4'-Ethyl-3',5'-dimethoxypropiophenone (1.11 g) obtained in the above Process 1 and indole-3-carboxaldehyde (1.45 g) were dissolved in ethanol (10 ml), and piperidine (0.85 g) was added thereto, followed by heating under reflux for 27 hours. The reaction solution was concentrated under reduced pressure, and the residue was purified by silica gel column chromatography. The obtained crude crystals were recrystallized from a mixed solvent of ethyl acetate and 2-propanol and then from a mixed solvent of ethyl acetate and hexane to give Compound 75 (0.45 g).

¹H-NMR (270 MHz, CDCl₃) δ1.14 (t, J=7.4 Hz, 3H), 2.32 (d, J=1.0 Hz, 3H), 2.74 (q, J=7.4 Hz, 2H), 3.85 (s, 6H), 6.96 (s, 2H), 7.19 (m, 1H), 7.28 (m, 1H), 7.44 (brd, J=8.4 Hz, 1H), 7.59 (brd, J=7.9 Hz, 1H), 7.63 (d, J=2.5 Hz, 1H), 7.72 (brs, 1H), 8.68 (brs, 1H) EI-MS m/z=365 (M⁺) Elemental analysis: $C_{22}H_{23}NO_3$ Calcd.(%): C, 75.62; H, 6.63; N, 4.01 Found (%): C, 75.78; H, 6.78; N, 3.98

EXAMPLE 76

3-(Indol-3-yl)-1-(3-methoxy-4,5-methylenedioxyphenyl)-2-methyl-2-propen-1-one (Compound 76)

Process 1

3-Methoxy-4,5-methylenedioxybenzaldehyde (5.55 g) was dissolved in tetrahydrofuran (150 ml), and ethylmagnesium bromide (IM tetrahydrofuran solution, 46.2 ml) was added thereto, followed by stirring at room temperature for 30 minutes. 1N Hydrochloric acid was added to the reaction solution, and the mixture was extracted with ethyl acetate. The organic layer was washed successively with water, a 5% aqueous solution of sodium bicarbonate and a saturated saline, dried over anhydrous magnesium sulfate and concentrated under reduced pressure. The residue was dissolved in acetone (300 ml), and Jones' reagent (5.3 ml) was added thereto under ice-cooling, followed by stirring at the same temperature for 30 minutes. 2-Propanol (5.3 ml) was added to the reaction solution and the mixture was concentrated under reduced pressure. The residue was subjected to partitioning between ethyl acetate and water. The organic layer was washed successively with water and a saturated saline, dried over anhydrous magnesium sulfate and concentrated under reduced pressure. The residue was purified by silica gel column chromatography to give 3'-methoxy-4',5'-methylenedioxypropiophenone (5.27 g).

$^1$H-NMR (90 MHz, CDCl$_3$) δ1.21 (t, J=7.3 Hz, 3H), 2.91 (q, J=7.3 Hz, 2H), 3.94 (s, 3H), 6.05 (s, 2H), 7.13 (d, J=. 1.5 Hz, 1H), 7.27 (d, J=1.5 Hz, 1H) EI-MS m/z=208 (M$^+$)

Process 2

3'-Methoxy-4',5'-methylenedioxypropiophenone (1.46 g) obtained in the above Process 1 and indole-3-carboxaldehyde (1.02 g) were dissolved in ethanol (14 ml), and piperidine (0.69 g) was added thereto, followed by heating under reflux for 120 hours. The precipitated crystals were collected by filtration, and the obtained crude crystals were recrystallized from a mixed solvent of ethyl acetate and hexane to give Compound 76 (0.64 g).

$^1$H-NMR (270 MHz, CDCl$_3$) δ2.29 (s, 3H), 3.92 (s, 3H), 6.08 (s, 2H), 6.98 (d, J=1.5 Hz, 1H), 7.06 (d, J=1.5 Hz, 1H), 7.19 (m, 1H), 7.27 (m, 1H), 7.43 (brd, J=7.9 Hz, 1H), 7.58–7.61 (m 3H), 8.68 (brs, 1H) EI-MS m/z=335 (M$^+$) Elemental analysis: C$_{20}$H$_{17}$NO$_4$ Calcd.(%): C, 71.63; H, 5.11; N, 4.18 Found (%): C, 71.31; H, 5.14; N, 4.06

EXAMPLE 77

1-(5-Ethoxy-3,4-dimethoxyphenyl)-3-(indol-3-yl)-2-methyl-2-propen-1-one (Compound 77)

Process 1

Substantially the same procedure as in Process 1 of Example 73 was repeated using 5-hydroxy-3,4-dimethoxybenzaldehyde (3.34 g) and ethyl iodide (5.72 g) to give 5'-ethoxy-3',4'-dimethoxypropiophenone (1.92 g).

$^1$H-NMR (90 MHz, CDCl$_3$) δ1.22 (t, J=7.3 Hz, 3H), 1.46 (t, J=7.0 Hz, 3H), 2.96 (q, J=7.3 Hz, 2H), 3.91 (s, 6H), 4.14 (q, J=7.0 Hz, 2H), 7.22 (s, 2H) EI-MS m/z=238 (M$^+$)

Process 2

5-Ethoxy-3',4'-dimethoxypropiophenone (1.19 g) obtained in the above Process 1 and indole-3-carboxaldehyde (0.73 g) were dissolved in ethanol (10 ml), and piperidine (0.43 g) was added thereto, followed by heating under reflux for 72 hours. The precipitated crystals were collected by filtration, and the obtained crude crystals were recrystallized from a mixed solvent of acetone and hexane to give Compound 77 (0.75 g).

$^1$H-NMR (270 MHz, CDCl$_3$) δ1.44 (t, J=7.1 Hz, 3H), 2.32 (d, J=1.0 Hz, 3H), 3.89 (s, 3H), 3.96 (s, 3H), 4.12 (q, J=7.1 Hz, 2H), 7.01 (s, 2H), 7.19 (m, 1H), 7.28 (m, 1H), 7.44 (brd, J=7.9 Hz, 1H), 7.58 (brd, J=7.9 Hz, 1H), 7.64 (d, J=3.0 Hz, 1H), 7.67 (brs, 1H), 8.76 (brs, 1H) EI-MS m/z=365 (M$^+$) Elemental analysis: C$_{22}$H$_{23}$NO$_4$ Calcd.(%): C, 72.31; H, 6.34; N, 3.83 Found (%): C, 72.36; H, 6.62; N, 3.80

EXAMPLE 78

1-(3-Bromo-4-dimethoxyphenyl)-3-(indol-3-yl)-2-methyl-2-propen-1-one (Compound 78)

Process 1

Substantially the same procedure as in Process 1 of Example 73 was repeated using 5-bromovanillin (5.78 g) and methyl iodide (7.10 g) to give 3'-bromo-4',5'-dimethoxypropiophenone (5.45 g).

$^1$H-NMR (90 MHz, CDCl$_3$) δ1.21 (t, J=7.3 Hz, 3H), 2.94 (q, J=7.3 Hz, 2H), 3.92 (s, 6H), 7.49 (d, J=1.9 Hz, 1H), 7.74 (d, J=1.9 Hz, 1H) EI-MS m/z=272, 274 (M$^+$)

Process 2

3'-Bromo-4',5'-dimethoxypropiophenone (1.37 g) obtained in the above Process 1 and indole-3-carboxaldehyde (0.73 g) were dissolved in ethanol (10 ml), and piperidine (0.43 g) was added thereto, followed by heating under reflux for 72 hours. The reaction solution was concentrated under reduced pressure, and the residue was purified by silica gel column chromatography. The obtained crude crystals were recrystallized from ethyl acetate to give Compound 78 (0.49 g).

$^1$H-NMR (270 MHz, CDCl$_3$) δ2.30 (d, J=0.7 Hz, 3H), 3.92 (s, 3H), 3.96 (s, 3H), 7.21 (m, 1H), 7.23 (d, J=2.1 Hz, 1H), 7.29 (m, 1H), 7.44 (brd, J=7.8 Hz, 1H), 7.55 (d, J=2.1 Hz, 1H), 7.61 (brd, J=7.8 Hz, 1H), 7.64 (d, J=2.1 Hz, 1H), 7.65 (brs, 1H), 8.71 (brs, 1H) EI-MS m/z=399, 401 (M$^+$) Elemental analysis: C$_{20}$H$_{18}$BrNO$_3$ Calcd.(%): C, 60.01; H, 4.53; N, 3.50 Found (%): C, 60.18; H, 4.61; N, 3.40

EXAMPLE 79

1-(4-Ethoxy-3,5-dimethoxyphenyl)-2-methyl-3-(6-methylindol-3-yl)-2-propen-1-one (Compound 79)

4'-Ethoxy-3',5'-dimethoxypropiophenone (1.19 g) obtained in Process 1 of Example 73 and 6-methylindole-3-carboxaldehyde [Journal of the Organic Chemistry (J. Org. Chem.), 44, 3741 (1979)] (0.80 g) were dissolved in ethanol (10 ml), and piperidine (0.49 g) was added thereto, followed by heating under reflux for 48 hours. The reaction solution was concentrated under reduced pressure, and the residue was purified by silica gel column chromatography. The obtained crude crystals were recrystallized from ethyl acetate to give Compound 79 (1.20 g).

$^1$H-NMR (270 MHz, CDCl$_3$) δ1.41 (t, J=7.1 Hz, 3H), 2.30 (d, J=1.3 Hz, 3H), 2.47 (s, 3H), 3.87 (s, 6H), 4.17 (q, J=7.1 Hz, 2H), 7.01 (dd, J=7.6, 0.7 Hz, 1H), 7.02 (s, 2H), 7.22 (s, 1H), 7.44 (d, J=7.6 Hz, 1H), 7.56 (d, J=2.6 Hz, 1H), 7.66 (S, 1H), 8.53 (brs, 1H) FAB-MS m/z=380 (M$^+$+1) Elemental analysis: C$_{23}$H$_{25}$NO$_4$ Calcd.(%): C, 72.80; H, 6.64; N, 3.69 Found (%): C, 72.82; H, 6.78; N, 3.69

EXAMPLE 80

1-(3-Methoxy-4,5-methylenedioxyphenyl)-2-methyl-3-(6-methylindol-3-yl)-2-propen-1-one (Compound 80)

3'-Methoxy-4',5'-methylenedioxypropiophenone (1.04 g) obtained in Process 1 of Example 76 and 6-methylindole-3-carboxaldehyde [Journal of the Organic Chemistry (J. Org. Chem.), 44, 3741 (1979)] (0.80 g) were dissolved in ethanol (10 ml), and piperidine (0.49 g) was added thereto, followed by heating under reflux for 48 hours. The precipitated crystals were collected by filtration, and the obtained crude crystals were recrystallized from a mixed solvent of ethyl acetate and hexane to give Compound 80 (0.64 g).

$^1$H-NMR (270 MHz, CDCl$_3$) δ2.29 (d, J=1.0 Hz, 3H), 2.24 (s, 3H), 3.93 (s, 3H), 6.08 (s, 2H), 6.98 (d, J=1.3 Hz, 1H), 7.02 (d, J=7.6 Hz, 1H), 7.06 (d, J=1.3 Hz, 1H), 7.22 (s, 1H), 7.47 (d, J=7.6 Hz, 1H), 7.54 (d, J=2.6 Hz, 1H), 7.59 (brs, 1H), 8.51 (brs, 1H) FAB-MS m/z=350 (M$^+$+1) Elemental analysis: C$_{21}$H$_{19}$NO$_4$ Calcd.(%): C, 72.19; H, 5.48; N, 4.01 Found (%): C, 72.41; H, 5.47; N, 3.99

EXAMPLE 81

1-(3-Bromo-4-isobutyloxy-5-methoxyphenyl)-3-(indol-3-yl)-2-methyl-2-propen-1-one (Compound 81)

Process 1

Substantially the same procedure as in Process 1 of Example 73 was repeated using 5-bromovanillin (11.65 g) and isobutyl bromide (27.40 g) to give 3'-bromo-4'-isobutyloxy-5'-methoxypropiophenone (1.93 g).

$^1$H-NMR (270 MHz, CDCl$_3$) δ1.06 (d, J=6.6 Hz, 6H), 1.21 (t, J=7.0 Hz, 3H), 2.13 (m, 1H), 2.94 (q, J=7.0 Hz, 2H), 3.84 (d, J=6.6 Hz, 2H), 3.89 (s, 3H), 7.48 (d, J=1.9 Hz, 1H), 7.74 (d, J=1.9 Hz, 1H) EI-MS m/z=314, 316 (M$^+$)

Process 2

3'-Bromo-4'-isobutyloxy-5'-methoxypropiophenone (0.64 g) obtained in the above Process 1 and indole-3-carboxaldehyde (0.59 g) were dissolved in ethanol (1 ml), and piperidine (0.35 g) was added thereto, followed by heating under reflux for 25 hours. The reaction solution was concentrated under reduced pressure, and the residue was purified by silica gel column chromatography. The obtained crude crystals were recrystallized from a mixed solvent of ethyl acetate and hexane to give Compound 81 (0.54 g).

$^1$H-NMR (270 MHz, CDCl$_3$) δ1.10 (d, J=6.4 Hz, 6H), 2.17 (m, 1H), 2.30 (d, J=0.7 Hz, 3H), 3.88 (d, J=6.4 Hz, 2H), 3.89 (s, 3H), 7.22 (m, 1H), 7.27 (d, J=1.7 Hz, 1H), 7.30 (m, 1H), 7.44 (m, 1H), 7.55 (d, J=1.7 Hz, 1H), 7.58 (d, J=8.1 Hz, 1H), 7.63 (d, J=2.0 Hz, 1H), 7.63 (s, 1H), 8.67 (s, 1H) EI-MS m/z=441, 443 (M$^+$) Elemental analysis: C$_{23}$H$_{24}$BrNO$_3$ Calcd.(%): C, 62.45; H, 5.47; N, 3.17 Found (%) : C, 62.65; H, 5.49; N, 3.15

EXAMPLE 82

1-(3-Bromo-4-isobutyloxy-5-methoxyphenyl)-2-methyl-3-(6-methylindol-3-yl)-2-methyl-2-propen-1-one (Compound 82)

3'-Bromo-4'-isobutyloxy-5'-methoxypropiophenone (1.58 g) obtained in Process 1 of Example 81 and 6-methylindole-3-carboxaldehyde [Journal of the Organic Chemistry (J. Org. Chem.), 44, 3741 (1979)] (0.80 g) were dissolved in ethanol (2 ml), and piperidine (0.85 g) was added thereto, followed by heating under reflux for 48 hours. The reaction solution was concentrated under reduced pressure, and the residue was purified by silica gel column chromatography. The obtained crude crystals were recrystallized from a mixed solvent of ethyl acetate and hexane to give Compound 82 (1.02 g).

$^1$H-NMR (270 MHz, CDCl$_3$) δ1.10 (d, J=6.3 Hz, 6H), 2.17 (m, 1H), 2.29 (d, J=1.0 Hz, 3H), 2.47 (s, 3H), 3.87 (d, J=6.3 Hz, 2H), 3.88 (s, 3H), 7.04 (dd, J=8.3, 1.0 Hz, 1H), 7.22 (s, 1H), 7.26 (d, J=1.7 Hz, 1H), 7.45 (d, J=8.3 Hz, 1H), 7.54 (d, J=1.7 Hz, 1H), 7.56(d, J=3.0 Hz, 1H), 7.62 (s, 1H), 8.57 (brs, 1H) EI-MS m/z=455, 457 (M$^+$) Elemental analysis: C$_{24}$H$_{26}$BrNO$_3$ Calcd.(%): C, 63.28; H, 5.76; N, 3.08 Found (%): C, 63.66; H, 6.11; N, 2.88

EXAMPLE 83

1-(4-Isobutyloxy-3,5-dimethoxyphenyl)-2-methyl-3-(6-methylindol-3-yl)-2-methyl-2-propen-1-one (Compound 83)

Process 1

4-Hydroxy-3,5-dimethoxybenzaldehyde (36.40 g) was dissolved in a mixed solvent of tetrahydrofuran (250 ml) and N,N-dimethylformamide (250 ml), and isobutyl bromide (54.80 g) and tetra-n-butylammonium fluoride (1M tetrahydrofuran solution, 400 ml) were added thereto, followed by heating under reflux for 15 hours. The reaction solution was cooled to room temperature, and subjected to partitioning between hexane and water. The organic layer was washed with water, dried over anhydrous magnesium sulfate and concentrated under reduced pressure to give 4'-isobutyloxy-3',5'-dimethoxybenzaldehyde (41.17 g).

$^1$H-NMR (90 MHz, CDCl$_3$) δ1.30 (d, J=6.6 Hz, 6H), 2.04 (m, 1H), 3.84 (d, J=6.6 Hz, 2H), 3.91 (s, 6H), 7.12 (s, 2H), 9.86 (s, 1H) EI-MS m/z=238 (M$^+$)

Process 2

Substantially the same procedure as in Process 1 of Example 76 was repeated using 4'-isobutyloxy-3',5'-dimethoxybenzaldehyde (1.37 g) obtained in the above Process 1 to give 4'-isobutyloxy-3',5'-dimethoxypropiophenone (1.37 g).

Process 3

4'-Isobutyloxy-3',5'-dimethoxypropiophenone (1.33 g) obtained in the above Process 2 and 6-methylindole-3-carboxaldehyde [Journal of the Organic Chemistry (J. Org. Chem.), 44, 3741 (1979)] (0.80 g) were dissolved in ethanol (2 ml), and piperidine (0.43 g) was added thereto, followed by heating under reflux for 80 hours. The reaction solution was concentrated under reduced pressure, and the residue was purified by silica gel column chromatography. The obtained crude crystals were recrystallized from a mixed solvent of ethyl acetate and hexane to give Compound 83 (0.96 g).

$^1$H-NMR (270 MHz, CDCl$_3$) δ1.00 (d, J=7.8 Hz, 6H), 2.05 (m, 1H), 2.25 (s, 3H), 2.41 (s, 3H), 3.79 (d, J=7.8 Hz, 2H), 3.81 (s, 6H), 6.956 (d, J=7.8 Hz, 1H), 6.957 (s, 2H), 7.16 (s, 1H), 7.38 (d, J=7.8 Hz, 1H), 7.50 (d, J=2.6 Hz, 1H), 7.60 (s, 1H), 8.53 (s, 1H) EI-MS m/z=407 (M$^+$) Elemental analysis: C$_{25}$H$_{29}$NO$_4$ Calcd.(%): C, 73.69; H, 7.17; N, 3.44 Found (%): C, 74.13; H, 7.23; N, 3.40

EXAMPLE 84

1-(4-Ethoxy-3,5-dimethoxyphenyl)-3-(6-ethylindol-3-yl)-2-methyl-2-propen-1-one (Compound 84)

Process 1

Phosphorus oxychloride (3.82 g) was added to N,N-dimethylformamide (20 ml), and the mixture was stirred at room temperature for 10 minutes. A solution of 6-ethylindole [Journal of the Chemical Society (J. Chem. Soc.), 7165 (1965)] in N,N-dimethylformamide (6 ml) was added to the reaction solution, and the mixture was stirred at room temperature for one hour. Ice (20 g) and then a 5N aqueous solution of sodium hydroxide (34 ml) were added to the reaction solution, and the mixture was heated under reflux for one hour. The reaction solution was ice-cooled, and the precipitated crystals were collected by filtration to give 6-ethylindole-3-carboxaldehyde (2.76 g).

$^1$H-NMR (90 MHz, CDCl$_3$) δ1.27 (t, J=7.6 Hz, 3H), 2.76 (q, J=7.6 Hz, 2H), 7.11–7.24 (m, 2H), 7.76 (s, 1H), 8.20 (d, J=8.2 Hz, 1H), 8.99 (s, 1H), 10.01 (s, 1H) EI-MS m/z=173 (M$^+$)

Process 2

Substantially the same procedure as in Process 2 of Example 74 was repeated using 4'-ethoxy-3', 5'-dimethoxypropiophenone (1.90 g) obtained in Process 1 of Example 73 and 6-ethylindole-3-carboxaldehyde (1.38 g) to give Compound 84 (0.84 g).

$^1$H-NMR (270 MHz, CDCl$_3$) δ1.30 (t, J=7.4 Hz, 3H), 1.41 (t, J=7.4 Hz, 3H), 2.30 (d, J=1.0 Hz, 3H), 2.76 (q, J=7.4 Hz, 2H), 3.87(s, 6H), 4.17 (q, J=7.4 Hz, 2H), 7.02 (s, 2H), 7.05 (dd, J=8.2, 1.5 Hz, 1H), 7.24 (s, 1H), 7.46 (d, J=8.2 Hz, 1H), 7.57 (d, J=2.5 Hz, 1H), 7.67 (s, 1H), 8.61 (s, 1H) EI-MS m/z=393 (M$^+$) Elemental analysis: C$_{24}$H$_{27}$NO$_4$ Calcd. (%): C, 73.26; H, 6.92; N, 3.56 Found (%): C, 73.46; H, 7.02; N, 3.52

EXAMPLE 85

1-(4-Ethoxy-3,5-dimethoxyphenyl)-3-(6-isopropylindol-3-yl)-2-methyl-2-propen-1-one (Compound 85)

Process 1

Substantially the same procedure as in Process 1 of Example 84 was repeated using 6-isopropylindole [Organic Synthesis (Org. Syn.), 63, 214 (1985)] (3.18 g) to give 6-isopropylindole-3-carboxaldehyde (3.56 g).

$^1$H-NMR (90 MHz, CDCl$_3$) δ1.31 (d, J=8.7 Hz, 6H), 2.70 (m, 1H), 7.08 (m, 1H), 7.24 (s, 1H), 7.74 (brs, 1H), 8.18 (d, J=9.0 Hz, 1H), 9.28 (s, 1H), 9.97 (s, 1H) EI-MS m/z=187 (M$^+$)

Process 2

Substantially the same procedure as in Process 2 of Example 74 was repeated using 4'-ethoxy-3',5'-dimethoxypropiophenone (2.38 g) obtained in Process 1 of Example 73 and 6-isopropylindole-3-carboxaldehyde obtained in the above Process 1 (1.87 g) to give Compound 85 (1.80 g).

$^1$H-NMR (270 MHz, CDCl$_3$) δ1.30 (d, J=6.9 Hz, 6H), 1.41 (t, J=7.0 Hz, 3H), 2.30 (d, J=1.0 Hz, 3H), 3.03 (m, 1H), 3.88 (s, 6H), 4.17 (q, J=7.0 Hz, 2H), 7.02 (s, 2H), 7.08 (dd, J=8.4, 1.5 Hz, 1H), 7.28 (s, 1H), 7.47 (d, J=8.4 Hz, 1H), 7.57 (d, J=2.5 Hz, 1H), 7.66 (s, 1H), 8.60 (s, 1H) EI-MS m/z=407 (M$^+$) Elemental analysis: C$_{25}$H$_{29}$NO$_4$ Calcd.(%): C, 73.69; H, 7.17; N, 3.44 Found (%): C, 73.85; H, 7.27; N, 3.43

EXAMPLE 86

3-(6-Chloroindol-3-yl)-1-(4-ethoxy-3,5-dimethoxyphenyl)-2-methyl-2-propen-1-one (Compound 86)

Process 1

Substantially the same procedure as in Process 1 of Example 84 was repeated using 6-chloroindole (4.11 g) to give 6-chloroindole-3-carboxaldehyde (4.78 g).

$^1$H-NMR (270 MHz, DMSO-d$_6$) δ7.24 (dd, J=8.5, 1.8 Hz, 1H), 7.56 (d, J=1.8 Hz, 1H), 8.07 (d, J=8.5 Hz, 1H), 8.32 (s, 1H), 9.93 (s, 1H), 12.20 (s, 1H) FAB-MS m/z=180, 182 (M$^+$+1)

Process 2

Substantially the same procedure as in Process 2 of Example 74 was repeated using 4'-ethoxy-3',5'-dimethoxypropiophenone (2.38 g) obtained in Process 1 of Example 73 and 6-chloroindole-3-carboxaldehyde obtained in the above Process 1 (1.80 g) to give Compound 86 (1.69 g).

$^1$H-NMR (270 MHz, CDCl$_3$) δ1.41 (t, J=7.0 Hz, 3H), 2.31 (d, J=0.9 Hz, 3H), 3.88 (s, 6H), 4.17 (q, J=7.0 Hz, 2H), 7.01 (s, 2H), 7.15 (dd, J=8.6, 1.8 Hz, 1H), 7.43 (d, J=1.8 Hz, 1H), 7.46 (d, J=8.6 Hz, 1H), 7.58 (s, 1H), 7.61 (d, J=2.6 Hz, 1H), 8.72 (s, 1H) EI-MS m/z=399, 401 (M$^+$) Elemental analysis: C$_{22}$H$_{22}$ClNO$_4$ Calcd.(%): C, 66.08; H, 5.55; N, 3.50 Found (%): C, 66.28; H, 5.64; N, 3.48

EXAMPLE 87

1-(3,5-Dimethoxy-4-propoxyphenyl)-2-methyl-3-(6-methylindol-3-yl)-2-propen-1-one (Compound 87)

Process 1

Substantially the same procedure as in Process 1 of Example 73 was repeated using 4-hydroxy-3,5-dimethoxybenzaldehyde (9.10 g) and propyl iodide (12.75 g) to give 3',5'-dimethoxy-4'-propoxypropiophenone (4.85 g).

$^1$H-NMR (270 MHz, CDCl$_3$) δ1.00 (t, J=7.0 Hz, 3H), 1.21 (t, J=7.3 Hz, 3H), 1.76 (m, 2H), 2.96 (q, J=7.3 Hz, 2H), 3.88 (s, 6H), 4.00 (t, J=7.0 Hz, 2H), 7.21 (s, 2H) EI-MS m/z=252 (M$^+$)

Process 2

Substantially the same procedure as in Process 2 of Example 74 was repeated using 3',5'-dimethoxy-4'-propoxypropiophenone (2.48 g) obtained in the above Process 1 and 6-methylindole-3-carboxaldehyde [Journal of the Organic Chemistry (J. Org. Chem.), 44, 3741 (1979)] (1.59 g) to give Compound 87 (1.73 g).

$^1$H-NMR (270 MHz, CDCl$_3$) δ1.05 (t, J=7.1 Hz, 3H), 1.83 (m, 2H), 2.31 (s, 3H), 2.48 (s, 3H), 3.88 (s, 6H), 4.05 (t, J=7.1 Hz, 2H), 7.021 (s, 2H), 7.024 (m, 1H), 7.23 (s, 1H), 7.44 (d, J=8.3 Hz, 1H), 7.57 (d, J=2.6 Hz, 1H), 7.67 (s, 1H ), 8.59 (s, 1H) EI-MS m/z=393 (M$^+$) Elemental analysis: C$_{24}$H$_{27}$NO$_4$ Calcd.(%): C, 73.26; H, 6.92; N, 3.56 Found (%): C, 73.44; H, 7.02; N, 3.51

EXAMPLE 88

1-(4-Buthoxy-3,5-dimethoxyphenyl)-2-methyl-3-(6-methylindol-3-yl)-2-propen-1-one (Compound 88)

Process 1

Substantially the same procedure as in Process 1 of Example 73 was repeated using 4-hydroxy-3,5-dimethoxybenzaldehyde (9.10 g) and butyl bromide (10.28 g) to give 4'-butoxy-3',5'-dimethoxypropiophenone (5.42 g).

$^1$H-NMR (270 MHz, CDCl$_3$) δ0.93 (t, J=7.3 Hz, 3H), 1.20 (t, J=7.3 Hz, 3H), 1.46 (m, 2H), 1.74 (m, 2H), 2.96 (q, J=7.3 Hz, 2H), 3.90 (s, 6H), 4.02 (t, J=7.3 Hz, 2H), 7.20 (s, 2H) EI-MS m/z=266 (M$^+$)

Process 2

Substantially the same procedure as in Process 2 of Example 74 was repeated using 4'-butoxy-3',5'-dimethoxypropiophenone (2.66 g) obtained in the above Process 1 and 6-methylindole-3-carboxaldehyde [Journal of the Organic Chemistry (J. Org. Chem.), 44, 3741 (1979)] (1.59 g) to give Compound 88 (1.43 g).

$^1$H-NMR (270 MHz, CDCl$_3$) δ0.97 (t, J=7.4 Hz, 3H), 1.53 (m, 2H), 1.81 (m, 2H), 2.29 (s, 3H), 2.45 (s, 3H), 3.85 (s, 6H), 4.07 (t, J=6.8 Hz, 2H), 6.996 (s, 2H), 6.999 (d, J=7.6 Hz, 1H), 7.20 (s, 1H), 7.41 (d, J=7.6 Hz, 1H), 7.54 (d, J=2.6 Hz, 1H), 7.64 (s, 1H), 8.55 (s, 1H) EI-MS m/z=407 (M$^+$) Elemental analysis: C$_{25}$H$_{29}$NO$_4$ Calcd.(%): C, 73.69; H, 7.17; N, 3.44 Found (%): C, 73.85; H, 7.29; N, 3.46

EXAMPLE 89

1-(2,5-Dimethoxyphenyl)-3-(indol-3-yl)-2-propen-1-one (Compound 89)

2',5'-Dimethoxyacetophenone (1.80 g) and indole-3-carboxaldehyde (1.45 g) were dissolved in ethanol (20 ml), and piperidine (0.85 g) was added thereto, followed by heating under reflux for 72 hours. The precipitated crystals were collected by filtration, and the obtained crude crystals were recrystallized from ethanol to give Compound 89 (1.35 g).

$^1$H-NMR (270 MHz, CDCl$_3$) δ3.82 (s, 3H), 3.89 (s, 3H), 6.96 (d, J=8.9 Hz, 1H), 7.04 (dd, J=8.9, 3.0 Hz, 1H), 7.23 (d, J=3.0 Hz, 1H), 7.28 (m, 2H), 7.43 (m, 1H), 7.51 (d, J=15.8 Hz, 1H), 7.55 (d, J=3.5 Hz, 1H), 7.92 (d, J=15.8 Hz, 1H), 7.97 (m, 1H), 8.56(brs, 1H) EI-MS m/z=307 (M$^+$) Elemental analysis: C$_{19}$H$_{17}$NO$_3$ Calcd.(%): C, 74.25; H, 5.58; N, 4.56 Found (%) : C, 74.30; H, 5.60; N, 4.44

EXAMPLE 90

1-(2,5-Dimethoxyphenyl)-3-(indol-3-yl)-2-methyl-2-propen-1-one (Compound 90)

Process 1

Substantially the same procedure as in Process 1 of Example 76 was repeated using 2,5-dimethoxybenzaldehyde (11.62 g) to give 2',5'-dimethoxypropiophenone (7.83 g).

$^1$H-NMR (90 MHz, CDCl$_3$) δ1.15 (t, J=7.3 Hz, 3H), 2.99 (q, J=7.3 Hz, 2H), 3.78 (s, 3H), 3.84 (s, 3H), 6.82–7.08 (m, 2H), 7.23 (d, J=2.9 Hz, 1H) EI-MS m/z=194 (M$^+$)

Process 2

2',5'-Dimethoxypropiophenone (1.94 g) obtained in the above Process 1 and indole-3-carboxaldehyde (1.45 g) were dissolved in ethanol (20 ml), and piperidine (0.85 g) was added thereto, followed by heating under reflux for 72 hours. The reaction solution was concentrated under reduced pressure, and the residue was purified by silica gel column chromatography. The obtained crude crystals were recrystallized from a mixed solvent of ethyl acetate and hexane to give Compound 90 (0.64 g).

$^1$H-NMR (270 MHz, CDCl$_3$) δ2.28 (d, J=1.0 Hz, 3H), 3.74 (s, 3H), 3.79 (s, 3H), 6.87 (d, J=2.6 Hz, 1H), 6.93 (d, J=8.8 Hz, 1H), 6.98 (dd, J=8.8, 2.6 Hz, 1H), 7.15 (m, 1H), 7.24 (m, 1H), 7.37–7.46 (m, 2H), 7.607 (brs, 1H), 7.613 (d, J=3.0 Hz, 1H), 8.76 (brs, 1H) EI-MS m/z=321 (M$^+$) Elemental analysis: C$_{20}$H$_{19}$NO$_3$ Calcd.(%): C, 74.75; H, 5.96; N, 4.36 Found (%): C, 75.11; H, 6.12; N, 4.28

EXAMPLE 91

3-(Indol-3-yl)-2-methyl-1-(2,4,5-trimethoxyphenyl)-2-propen-1-one (Compound 91)

Process 1

Substantially the same procedure as in Process 1 of Example 76 was repeated using 2,4,5-trimethoxybenzaldehyde (1.96 g) to give 2',4',5'-trimethoxypropiophenone (0.50 g).

$^1$H-NMR (270 MHz, CDCl$_3$) δ1.16 (t, J=7.3 Hz, 3H), 2.99 (q, J=7.3 Hz, 2H), 3.88 (s, 3H), 3.91 (s, 3H), 3.95 (s, 3H), 6.50 (s, 1H), 7.43 (s, 1H) FAB-MS m/z=225 (M$^+$+1)

Process 2

2',4',5'-Trimethoxypropiophenone (0.45 g) obtained in the above Process 1 and indole-3-carboxaldehyde (0.28 g) were dissolved in ethanol (5 ml), and piperidine (0.17 g) was added thereto, followed by heating under reflux for 144 hours. The reaction solution was concentrated under reduced pressure, and the residue was purified by silica gel column chromatography. The obtained crude crystals were recrystallized from a mixed solvent of ethyl acetate and hexane to give Compound 91 (0.21 g).

$^1$H-NMR (270 MHz, CDCl$_3$) δ2.28 (d, J=0.7 Hz, 3H), 3.77 (s, 3H), 3.85 (s, 3H), 3.98 (s, 3H), 6.62 (s, 1H), 6.92 (s, 1H), 7.16 (m, 1H), 7.23 (d, J=2.1 Hz, 1H), 7.42 (brd, J=8.2 Hz, 1H), 7.50 (d, J=7.9 Hz, 1H), 7.62–7.65 (m, 2H), 8.74 (brs, 1H) EI-MS m/z=351 (M$^+$) Elemental analysis: C$_{21}$H$_{21}$NO$_4$.0.2H$_2$O Calcd.(%): C, 71.05; H, 6.08; N, 3.95 Found (%): C, 71.05; H, 6.13; N, 3.83

EXAMPLE 92

3-(Indol-3-yl)-2-methyl-1-(2,3,4-trimethoxyphenyl)-2-propen-1-one (Compound 92)

Process 1

Substantially the same procedure as in Process 1 of Example 76 was repeated using 2,3,4-trimethoxybenzaldehyde (1.96 g) to give 2',3',4'-trimethoxypropiophenone (1.94 g).

$^1$H-NMR (90 MHz, CDCl$_3$) δ1.17 (t, J=7.3 Hz, 3H), 2.97 (q, J=7.3 Hz, 2H), 3.75 (s, 3H), 3.90 (s, 3H), 3.96 (s, 3H), 6.70 (d, J=9.0 Hz, 1H), 7.43 (d, J=9.0 Hz, 1H) FAB-MS m/z=225 (M$^+$+1)

Process 2

2',3',4'-Trimethoxypropiophenone (1.12 g) obtained in the above Process 1 and indole-3-carboxaldehyde (0.73 g) were dissolved in ethanol (10 ml), and piperidine (0.43 g) was added thereto, followed by heating under reflux for 72 hours. The precipitated crystals were collected by filtration, and the obtained crude crystals were recrystallized from ethanol to give Compound 92 (0.49 g).

$^1$H-NMR (270 MHz, CDCl$_3$) δ2.29 (d, J=1.0 Hz, 3H), 3.86 (s, 3H), 3.92 (s, 3H), 3.94 (s, 3H), 6.74 (d, J=8.6 Hz, 1H), 7.06 (d, J=8.6 Hz, 1H), 7.15 (m, 1H), 7.25 (m, 1H), 7.41 (brd, J=7.9 Hz, 1H), 7.48 (brd, J=7.9 Hz, 1H), 7.58 (brs, 1H), 7.62 (d, J=3.0 Hz, 1H), 8.74 (brs, 1H) EI-MS m/z=351 (M$^+$) Elemental analysis: C$_{21}$H$_{21}$NO$_4$ Calcd.(%): C, 71.78; H, 6.02; N, 3.99 Found (%): C, 71.78; H, 6.19; N, 3.90

EXAMPLE 93

(Z)-3-(Indol-3-yl)-2-methoxy-1-(3,4,5-trimethoxyphenyl)-2-propen-1-one (Compound 93)

2-Methoxy-3',4',5'-trimethoxyacetophenone (300.0 mg) obtained in Reference Example 4 and indole-3-carbaldehyde (362.5 mg) were dissolved in ethanol (10 ml), and piperidine (212.9 mg) was added thereto, followed by heating under reflux for 9 hours. The reaction solution was ice-cooled and the precipitated crystals were collected by filtration. The obtained crude crystals were recrystallized from ethyl acetate to give Compound 93 (254.8 mg).

$^1$H-NMR (270 MHz, CDCl$_3$) δ3.88 (s, 3H), 3.92 (s, 6H), 3.97 (s, 3H), 7.11 (s, 1H), 7.15–7.29 (m, 2H), 7.19 (s, 2H), 7.43 (dd, J=7.6, 1.3 Hz, 1H), 7.65 (d, J=7.6 Hz, 1H), 8.11 (d, J=2.6 Hz, 1H), 8.67 (brs, 1H) EI-MS m/z=367 (M$^+$) Elemental Analysis: C$_{21}$H$_{21}$NO$_5$ Calcd.(%): C, 68.65; H, 5.76; N, 3.81 Found (%): C, 68.60; H, 5.68; N, 3.75

EXAMPLE 94

(Z)-2-Ethoxy-3-(indol-3-yl)-1-(3,4,5-trimethoxyphenyl)-2-propen-1-one (Compound 94)

2-Ethoxy-3',4',5'-trimethoxyacetophenone (509.0 mg) obtained in Reference Example 5 and indole-3-carbaldehyde (435.0 mg) were dissolved in ethanol (12 ml), and piperidine (255.5 mg) was added thereto, followed by heating under reflux for 24 hours. The reaction solution was concentrated under reduced pressure and the residue was purified by silica gel column chromatography. The obtained crude crystals were recrystallized from a mixed solvent of ethyl acetate and hexane (1:1) to give Compound 94 (112.5 mg).

$^1$H-NMR (270 MHz, CDCl$_3$) δ1.42 (t, J=7.0 Hz, 3H), 3.92 (s, 6H), 3.96 (s, 3H), 4.11 (q, J=7.0 Hz, 2H), 7.10 (s, 1H), 7.15–7.32 (m, 2H), 7.21 (s, 2H), 7.43 (d, J=8.6 Hz, 1H), 7.66 (d, J=7.6 Hz, 1H), 8.17 (d, J=2.6 Hz, 1H), 8.58 (brs, 1H). EI-MS m/z=381 (M$^+$) Elemental Analysis: $C_{22}H_{23}NO_5$ Calcd.(%): C, 69.28; H, 6.08; N, 3.67 Found (%): C, 69.52; H, 6.27; N, 3.57

EXAMPLE 95

(Z)-3-(Indol-3-yl)-2-propyloxy-1-(3,4,5-trimethoxyphenyl)-2-propen-1-one (Compound 95)

3',4',5'-Trimethoxy-2-propyloxyacetophenone (690.0 mg) obtained in Reference Example 6 and indole-3-carbaldehyde (373.3 mg) were dissolved in ethanol (10 ml), and piperidine (254.6 mg) was added thereto, followed by heating under reflux for 24 hours. The reaction solution was concentrated under reduced pressure and the residue was purified by silica gel column chromatography. The obtained crude crystals were recrystallized from a mixed solvent of ethyl acetate, hexane, and isopropyl ether (2:2:3) to give Compound 95 (701.5 mg).

$^1$H-NMR (270 MHz, CDCl$_3$) δ1.02 (t, J=7.2 Hz, 3H), 1.82 (sext, J=7.2 Hz, 2H), 3.92 (s, 6H), 3.96 (s, 3H), 4.01 (t, J=7.2 Hz, 2H), 7.05 (s, 1H), 7.16–7.31 (m, 2H), 7.21 (s, 2H), 7.43 (d, J=7.9 Hz, 1H), 7.64 (d, J=7.9 Hz, 1H), 8.15 (d, J=2.5 Hz, 1H), 8.57 (brs, 1H) EI-MS m/z=395 (M$^+$) Elemental Analysis: $C_{23}H_{25}NO_5$ Calcd.(%): C, 69.86; H, 6.37; N, 3.54 Found (%): C, 69.88; H, 6.45; N, 3.53

EXAMPLE 96

(Z)-2-Isopropyloxy-3-(indol-3-yl)-1-(3,4,5-trimethoxyphenyl)-2-propen-1-one (Compound 96)

2-Isopropyloxy-3',4',5'-trimethoxyacetophenone (443.0 mg) obtained in Reference Example 7 and indole-3-carbaldehyde (360.0 mg) were dissolved in ethanol (10 ml), and piperidine (211.0 mg) was added thereto, followed by heating under reflux for 48 hours. The reaction solution was concentrated under reduced pressure and the residue was purified by silica gel column chromatography. The obtained crude crystals were recrystallized from a mixed solvent of ethyl acetate and hexane (1:1) to give Compound 96 (386.0 mg).

$^1$H-NMR (270 MHz, CDCl$_3$) δ1.34 (d, J=6.2 Hz, 6H), 3.92 (s, 6H), 3.96 (s, 3H), 4.51 (m, 1H), 7.09 (s, 1H), 7.15–7.29 (m, 2H), 7.23 (s, 2H), 7.42 (dd, J=7.3, 1.0 Hz, 1H), 7.66 (d, J=7.6 Hz, 1H), 8.21 (d, J=2.6 Hz, 1H), 8.54 (brs, 1H) EI-MS m/z 395 (M$^+$) Elemental Analysis: $C_{23}H_{25}NO_5$ Calcd.(%): C, 69.86; H, 6.37; N, 3.54 Found (%): C, 69.88; H, 6.57; N, 3.50

EXAMPLE 97

(Z)-3-(Indol-3-yl)-1-(3,4,5-trimethoxyphenyl)-2-(2-trimethylsilylethoxy)-2-propen-1-one (Compound 97)

3',4',5'-Trimethoxy-2-(2-trimethylsilylethoxy)-acetophenone (720.0 mg) obtained in Reference Example 8 and indole-3-carbaldehyde (640.0 mg) were dissolved in ethanol (15 ml), and piperidine (376.1 mg) was added thereto, followed by heating under reflux for 24 hours. The reaction solution was concentrated under reduced pressure and the residue was purified by silica gel column chromatography. The obtained crude crystals were purified by preparative high pressure liquid chromatography (HPLC) (YMC pack ODS, SH-343-5, S-5, 120A, 250×20 mm, acetonitrile:water=80:20) to give Compound 97 (83.7 mg).

$^1$H-NMR (270 MHz, CDCl$_3$) δ0.01 (s, 9H), 1.23 (m, 2H), 3.92 (s, 6H), 3.96 (s, 3H), 4.14 (m, 2H), 7.07 (s, 1H), 7.20 (s, 2H), 7.22 (m, 1H), 7.28 (m, 1H), 7.43 (dd, J=8.1, 0.9 Hz, 1H), 7.64 (d, J=7.3 Hz, 1H), 8.22 (d, J=2.6 Hz, 1H), 8.57 (brs, 1H) EI-MS m/z=453 (M$^+$) Elemental Analysis: $C_{25}H_{31}NO_5Si$ Calcd.(%): C, 66.20; H, 6.89; N, 3.09 Found (%): C, 66.14; H, 6.72; N, 3.15

EXAMPLE 98

(Z)-3-(Indol-3-yl)-1-(3,4,5-trimethoxyphenyl)-2-(2-trimethylsilylpropyloxy)-2-propen-1-one (Compound 98)

3',4',5'-Trimethoxy-2-(3-trimethylsilylpropyloxy)-acetophenone(843.0 mg) obtained in Reference Example 9 and indole-3-carbaldehyde (359.5 mg) were dissolved in ethanol (10 ml), and piperidine (211.1 mg) was added thereto, followed by heating under reflux for 24 hours. The reaction solution was concentrated under reduced pressure and the residue was purified by silica gel column chromatography. The obtained crude crystals were recrystallized from a mixed solvent of ethyl acetate, hexane, and isopropyl ether (2:2:3) to give Compound 98 (547.1 mg).

$^1$H-NMR (270 MHz, CDCl$_3$) δ–0.01 (s, 9H), 0.57 (m, 2H), 1.80 (m, 2H), 3.93 (s, 6H), 3.97 (s, 3H), 4.01 (m, 2H), 7.05 (s, 1H), 7.16–7.33 (m, 2H), 7.21 (s, 2H), 7.44 (d, J=7.4 Hz, 1H), 7.66 (d, J=7.9 Hz, 1H), 8.16 (d, J=3.0 Hz, 1H), 8.56 (s, 1H) EI-MS m/z=467 (M$^+$) Elemental Analysis: $C_{26}H_{33}NO_5Si$ Calcd.(%): C, 66.78; H, 7.11; N, 3.00 Found (%): C, 66.77; H, 7.30; N, 2.94

EXAMPLE 99

(Z)-3-(Indol-3-yl)-2-(2-methylphenoxy)-1-(3,4,5-trimethoxyphenyl)-2-propen-1-one (Compound 99)

3',4',5'-Trimethoxy-2-(2-methylphenoxy)-acetophenone (600.0 mg) obtained in Reference Example 10 and indole-3-carbaldehyde (551.0 mg) were dissolved in ethanol (20 ml), and piperidine (323.0 mg) was added thereto, followed by heating under reflux for 48 hours. The reaction solution was concentrated under reduced pressure and the residue was purified by silica gel column chromatography. The obtained crude crystals were purified by preparative HPLC (YMC pack ODS, SH-343-5, S-5, 120A, 250×20 mm, acetonitrile:water=70:30) to give Compound 99 (601.4 mg).

$^1$H-NMR (270 MHz, CDCl$_3$) δ2.49 (s, 3H), 3.88 (s, 6H), 3.92 (s, 3H), 6.81 (dd, J=7.9, 1.3 Hz, 1H), 6.89 (dd, J=7.3, 1.3 Hz, 1H), 7.00 (ddd, J=7.9, 7.3, 1.3 Hz, 1H), 7.15 (s, 2H), 7.19 (dd, J=7.3, 1.3 Hz, 1H), 7.23–7.30 (m, 2H), 7.40 (m, 1H), 7.61 (s, 1H), 7.73 (m, 1H), 7.86 (d, J=2.6 Hz, 1H), 8.54 (brs, 1H) EI-MS m/z=443 (M$^+$) Elemental Analysis: $C_{27}H_{25}NO_5$ Calcd.(%): C, 73.12; H, 5.68; N, 3.16 Found (%): C, 72.87; H, 5.80; N, 2.99

EXAMPLE 100

(Z)-2-(4-Bromophenoxy)-3-(indol-3-yl)-1-(3,4,5-trimethoxyphenyl)-2-propen-1-one (Compound 100)

2-(4-Bromophenoxy)-3',4',5'-trimethoxyacetophenone (906.8 mg) obtained in Reference Example 11 and indole-3-carbaldehyde (652.5 mg) were dissolved in ethanol (15 ml), and piperidine (382.5 mg) was added thereto, followed by heating under reflux for 24 hours. The reaction solution was concentrated under reduced pressure and the residue was purified by silica gel column chromatography to give Compound 100 (1.18 g).

¹H-NMR (270 MHz, CDCl₃) δ3.90 (s, 6H), 3.94 (s, 3H), 6.92 (d, J=9.1 Hz, 2H), 7.18 (s, 2H), 7.21–7.32 (m, 2H), 7.35 (d, J=9.1 Hz, 2H), 7.42 (dd, J=6.6, 2.0 Hz, 1H), 7.69 (s, 1H), 7.73 (dd, J=6.2, 2.1 Hz, 1H), 7.83 (d, J=3.0 Hz, 1H), 8.59 (brs, 1H) EI-MS m/z=507, 509 (M⁺) Elemental Analysis: $C_{26}H_{22}BrNO_5$ Calcd.(%): C, 61.43; H, 4.36; N, 2.76 Found (%): C, 61.33; H, 4.41; N, 2.53

EXAMPLE 101

(Z)-3-(Indol-3-yl)-2-methylthio-1-(3,4,5-trimethoxyphenyl)-2-propen-1-one (Compound 101)

2-Methylthio-3',4',5'-trimethoxyacetophenone (900.0 mg) obtained in Reference Example 12 and indole-3-carbaldehyde (1.02 g) were dissolved in ethanol (35 ml), and piperidine (598.4 mg) was added thereto, followed by heating under reflux for 48 hours. The reaction solution was concentrated under reduced pressure and the residue was purified by silica gel column chromatography. The obtained crude crystals were purified by preparative HPLC (YMC pack ODS, SH-343-5, S-5, 120A, 250×20 mm, acetonitrile:water=70:30) to give Compound 101 (752.9 mg).

¹H-NMR (270 MHz, CDCl₃) δ2.39 (s, 3H), 3.90 (s, 6H), 3.97 (s, 3H), 7.16–7.30 (m, 2H), 7.20 (s, 2H), 7.44 (d, J=7.9 Hz, 1H), 7.58 (d, J=7.9 Hz, 1H), 7.67 (s, 1H), 8.33 (d, J=2.6 Hz, 1H), 8.73 (brs, 1H) EI-MS m/z=383 (M⁺) Elemental Analysis: $C_{21}H_{21}NO_4S$ Calcd.(%): C, 65.78; H, 5.52; N, 3.65 Found (%): C, 66.04; H, 5.37; N, 3.58

EXAMPLE 102

(Z)-3-(Indol-3-yl)-1-(3,4,5-trimethoxyphenyl)-2-(2-trimethylsilylethylthio)-2-propen-1-one (Compound 102)

3',4',5'-Trimethoxy-2-(2-trimethylsilylethylthio)-acetophenone (1.00 g) obtained in Reference Example 13 and indole-3-carbaldehyde (0.85 g) were dissolved in ethanol (30 ml), and piperidine (0.50 g) was added thereto, followed by heating under reflux for 48 hours. The reaction solution was concentrated under reduced pressure and the residue was purified by silica gel column chromatography. The obtained crude crystals were purified by preparative HPLC (YMC pack ODS, SH-343-5, S-5, 120A, 250×20 mm, acetonitrile:water=80:20) to give Compound 102 (0.76 g).

¹H-NMR (270 MHz, CDCl₃) δ−0.05 (s, 9H), 0.89 (m, 2H), 2.90 (m, 2H), 3.89 (s, 6H), 3.97 (s, 3H), 7.16–7.30 (m, 2H), 7.20 (s, 2H), 7.44 (d, J=7.9 Hz, 1H), 7.60 (d, J=7.6 Hz, 1H), 7.71 (s, 1H), 8.39 (d, J=3.0 Hz, 1H), 8.67 (brs, 1H) EI-MS m/z=469 (M⁺) Elemental Analysis: $C_{25}H_{31}NO_4SSi$ Calcd.(%): C, 63.93; H, 6.65; N, 2.98 Found (%): C, 63.95; H, 6.70; N, 2.92

EXAMPLE 103

(Z)-2-(4-Fluorophenylthio)-3-(indol-3-yl)-1-(3,4,5-trimethoxyphenyl)-2-propen-1-one (Compound 103)

2-(4-Fluorophenylthio)-3',4',5'-trimethoxy-acetophenone (1.19 g) obtained in Reference Example 14 and indole-3-carbaldehyde (1.03 g) were dissolved in ethanol (35 ml), and piperidine (0.60 g) was added thereto, followed by heating under reflux for 24 hours. The reaction solution was concentrated under reduced pressure and the residue was purified by silica gel column chromatography. The obtained crude crystals were recrystallized from a mixed solvent of ethyl acetate and hexane (1:1) to give Compound 103 (0.83 g).

¹H-NMR (270 MHz, CDCl₃) δ3.84 (s, 6H), 3.93 (s, 3H), 6.89 (t, J=8.6 Hz, 2H), 7.03 (s, 2H), 7.21–7.33 (m, 4H), 7.44 (d, J=7.6 Hz, 1H), 7.69 (d, J=7.3 Hz, 1H), 8.01 (s, 1H), 8.40 (d, J=3.0 Hz, 1H), 8.78 (brs, 1H) EI-MS m/z=463 (M⁺) Elemental Analysis: $C_{26}H_{22}FNO_4S$ Calcd.(%): C, 67.37; H, 4.78; N, 3.02 Found (%): C, 67.32; H, 4.82; N, 2.95

EXAMPLE 104

(Z)-2-(2-Hydroxyethylthio)-3-(indol-3-yl)-1-(3,4,5-trimethoxyphenyl)-2-propen-1-one (Compound 104)

2-(2-Hydroxyethylthio)-3',4',5'-trimethoxyacetophenone (858.0 mg) obtained in Reference Example 15 and indole-3-carbaldehyde (435.0 mg) were dissolved in ethanol (10 ml), and piperidine (255.0 mg) was added thereto, followed by heating under reflux for 24 hours. The reaction solution was concentrated under reduced pressure and the residue was purified by silica gel column chromatography. The obtained crude crystals were purified by preparative HPLC (YMC pack ODS, SH-343-5, S-5, 120A, 250×20 mm, acetonitrile:water=50:50) to give Compound 104 (636.5 mg).

¹H-NMR (270 MHz, CDCl₃) δ3.04 (t, J=5.6 Hz, 2H), 3.16 (t, J=5.6 Hz, 1H), 3.71 (q, J=5.6 Hz, 2H), 3.88 (s, 6H), 3.97 (s, 3H), 7.12 (s, 2H), 7.20–7.32 (m, 2H), 7.46 (d, J=7.9 Hz, 1H), 7.56 (d, J=7.9 Hz, 1H), 7.95 (s, 1H), 8.60 (d, J=3.0 Hz, 1H), 8.88 (brs, 1H) FAB-MS m/z=414 (M⁺+1) Elemental Analysis: $C_{22}H_{23}NO_5S \cdot 0.5H_2O$ Calcd.(%): C, 62.54; H, 5.73; N, 3.32 Found (%): C, 62.56; H, 5.55; N, 3.02

EXAMPLE 105

(Z)-2-(2-Hydroxyethylthio)-3-(6-methylindol-3-yl)-1-(3,4,5-trimethoxyphenyl)-2-propen-1-one (Compound 105)

2-(2-Hydroxyethylthio)-3',4',5'-trimethoxy-acetophenone (1.00 g) obtained in Reference Example 15 and 6-methylindole-3-carbaldehyde [J. Org. Chem., 44, 3741 (1979)] (0.56 g) were dissolved in ethanol (10 ml), and piperidine (0.30 g) was added thereto, followed by heating under reflux for 72 hours. The reaction solution was concentrated under reduced pressure and the residue was purified by silica gel column chromatography. The obtained crude crystals were recrystallized from a mixed solvent of ethyl acetate and hexane (1:1) to give Compound 105 (911.3 mg).

¹H-NMR (270 MHz, CDCl₃) δ2.47 (s, 3H), 3.03 (t, J=5.4 Hz, 2H), 3.09 (s, 1H), 3.70 (t, J=5.4 Hz, 2H), 3.88 (s, 6H), 3.97 (s, 3H), 7.04 (d, J=8.4 Hz, 1H), 7.12 (s, 2H), 7.24 (s, 1H), 7.42 (d, J=8.4 Hz, 1H), 7.94 (s, 1H), 8.53 (d, J=2.5 Hz, 1H), 8.75 (brs, 1H) EI-MS m/z=427 (M⁺) Elemental Analysis: $C_{23}H_{25}NO_5S$ Calcd.(%): C, 64.62; H, 5.89; N, 3.28 Found (%): C, 64.37; H, 6.13; N, 3.14

EXAMPLE 106

(Z)-2-(β-D-Glucosylthio)-3-(6-methylindol-3-yl)-1-(3,4,5-trimethoxyphenyl)-2-propen-1-one (Compound 106)

2-(β-D-Glucosylthio)-3',4',5'-trimethoxy-acetophenone (1.01 g) obtained in Reference Example 17 and 6-methylindole-3-carbaldehyde (0.40 g) were dissolved in ethanol (10 ml), and piperidine (0.21 g) was added thereto, followed by heating under reflux for 24 hours. The reaction solution was concentrated under reduced pressure and the residue was purified by silica gel column chromatography.

The obtained crude crystals were recrystallized from ethanol and purified by preparative HPLC (YMC pack ODS, SH-343-5, S-5, 120A, 250×20 mm, acetonitrile:water= 40:60). The eluate was concentrated under reduced pressure and the residue was recrystallized from a mixed solvent of ethanol and isopropyl ether (1:1) to give Compound 106 (322.2 mg).

$^1$H-NMR (270 MHz, DMSO-d$_6$) δ2.40 (s, 3H), 2.78 (m, 1H), 3.16–3.32 (m, 5H), 3.79 (s, 3H), 3.80 (s, 3H), 3.81 (s, 3H), 4.24 (t, J=5.6 Hz, 1H), 4.76 (d, J=8.6 Hz, 1H), 4.82 (d, J=4.6 Hz, 1H), 5.09 (d, J=2.9 Hz, 1H), 5.46 (d, J=5.0 Hz, 1H), 6.94 (d, J=8.3 Hz, 1H), 7.09 (s, 2H), 7.26 (s, 1H), 7.33 (d, J=8.3 Hz, 1H), 7.52 (s, 1H), 8.12 (d, J=2.5 Hz, 1H), 11.73 (s, 1H) FAB-MS m/z=545 (M$^+$+1) Elemental Analysis: C$_{27}$H$_{31}$NO$_9$S.0.8H$_2$O Calcd.(%): C, 57.91; H, 5.87; N, 2.50 Found (%): C, 57.88; H, 5.77; N, 2.40

EXAMPLE 107

(Z)-2-Carboxymethylthio-3-(indol-3-yl)-1-(3,4,5-trimethoxyphenyl)-2-propen-1-one (Compound 107)

2-Carboxymethylthio-3',4',5'-trimethoxy-acetophenone (0.60 g) obtained in Reference Example 18 and indole-3-carbaldehyde (0.29 g) were dissolved in ethanol (5 ml), and piperidine (0.34 g) was added thereto, followed by heating under reflux for 40 hours. The reaction solution was concentrated under reduced pressure and the residue was purified by silica gel column chromatography. The obtained crude crystals were purified by preparative HPLC (YMC pack ODS, SH-343-5, S-5, 120A, 250×20 mm, acetonitrile:a 0.1M aqueous solution of ammonium acetate=30:70). The eluate was concentrated under reduced pressure and the residue was subjected to partitioning between chloroform and a 10% aqueous solution of citric acid. The organic layer was concentrated under reduced pressure to give Compound 107 (343.3 mg).

$^1$H-NMR (270 MHz, CDCl$_3$) δ3.62 (s, 2H), 3.88 (s, 6H), 3.99 (s, 3H), 7.11 (s, 2H), 7.21 (m, 1H), 7.31 (m, 1H), 7.47 (d, J=7.9 Hz, 1H), 7.52 (d, J=7.9 Hz, 1H), 7.99 (s, 1H), 8.52 (d, J=3.0 Hz, 1H), 9.10 (brs, 1H), CO2H; not detected FAB-MS m/z=428 (M$^+$+1) Elemental Analysis: C$_{22}$H$_{21}$NO$_6$S.0.4H$_2$O Calcd.(%): C, 60.79; H, 5.05; N, 3.22 Found (%): C, 60.76; H, 4.86; N, 3.17

EXAMPLE 108

(Z)-3-(Indol-3-yl)-2-methoxycarbonylmethylthio-1-(3,4,5-trimethoxyphenyl)-2-propen-1-one (Compound 108)

Compound 107 (50.0 mg) obtained in Example 107 was dissolved in a mixed solvent of chloroform (10 ml) and methanol (5 ml), and a solution (0.5 ml) of trimethylsilyl-diazomethane in hexane, followed by stirring for 10 minutes. Acetic acid (20.0 mg) was added to the reaction solution and the mixture was subjected to partitioning between chloroform and a 5% aqueous solution of sodium bicarbonate. The organic layer was concentrated under reduced pressure and the residue was purified by silica gel column chromatography. The obtained crude crystals were recrystallized from isopropyl ether to give Compound 108 (36.9 mg).

$^1$H-NMR (270 MHz, CDCl$_3$) δ3.58 (s, 3H), 3.68 (s, 2H), 3.90 (s, 6H), 3.97 (s, 3H), 7.15 (s, 2H), 7.19 (m, 1H), 7.28 (m, 1H), 7.48 (m, 1H), 7.54 (d, J=7.9 Hz, 1H), 7.83 (s, 1H), 8.46 (d, J=2.7 Hz, 1H), 8.78 (s, 1H) EI-MS m/z=441 (M$^+$) Elemental Analysis: C$_{23}$H$_{23}$NO$_6$S Calcd.(%): C, 62.57; H, 5.25; N, 3.17 Found (%): C, 62.40; H, 5.26; N, 3.13

EXAMPLE 109

(Z)-2-(2-Diethylaminoethylthio)-3-(indol-3-yl)-1-(3,4,5-trimethoxyphenyl)-2-propen-1-one (Compound 109)

2-(2-Diethylaminoethylthio)-3',4',5'-trimethoxy-acetophenone (671.0 mg) obtained in Reference Example 19 and indole-3-carbaldehyde (290.0 mg) were dissolved in ethanol (5 ml), and piperidine (170.0 mg) was added thereto, followed by heating under reflux for 44 hours. The reaction solution was concentrated under reduced pressure and the residue was purified by silica gel column chromatography. The obtained crude crystals were purified by preparative HPLC (YMC pack ODS, SH-343-5, S-5, 120A, 250×20 mm, acetonitrile:a 0.1M aqueous solution of ammonium acetate=50:50). The eluate was concentrated under reduced pressure and the residue was subjected to partitioning between chloroform and a 5% aqueous solution of sodium bicarbonate. The organic layer was concentrated under reduced pressure to give Compound 109 (410.6 mg).

$^1$H-NMR (270 MHz, CDCl$_3$) δ0.95 (t, J=7.1 Hz, 6H), 2.49 (q, J=7.1 Hz, 4H), 2.71 (m, 2H), 2.94 (m, 2H), 3.89 (s, 6H), 3.97 (s, 3H), 7.18 (s, 2H), 7.19 (m, 1H), 7.27 (m, 1H), 7.44 (d, J=7.9 Hz, 1H), 7.57 (d, J=7.6 Hz, 1H), 7.73 (s, 1H), 8.43 (d, J=2.3 Hz, 1H), 8.87 (s, 1H) FAB-MS m/z=469 (M$^+$+1) Elemental Analysis: C$_{26}$H$_{32}$N$_2$O$_4$S.0.6H$_2$O Calcd.(%): C, 65.14; H, 6.98; N, 5.84 Found (%): C, 65.25; H, 7.16; N, 5.86

EXAMPLE 110

(Z)-3-(Indol-3-yl)-2-(4-phenoxybutylthio)-1-(3,4,5-trimethoxyphenyl)-2-propen-1-one (Compound 110)

2-(4-Phenoxybutylthio)-3',4',5'-trimethoxy-acetophenone (195.0 mg) obtained in Reference Example 20 and indole-3-carbaldehyde(72.5 mg) were dissolved in ethanol (3 ml), and piperidine (42.6 mg) was added thereto, followed by heating under reflux for 4 hours. The reaction solution was concentrated under reduced pressure and the residue was purified by silica gel column chromatography. The obtained crude crystals were purified by preparative HPLC (YMC pack ODS, SH-343-5, S-5, 120A, 250×20 mm, acetonitrile:water=70:30). The eluate was concentrated under reduced pressure and the the obtained crude crystals were recrystallized from isopropyl ether to give Compound 110 (94.0 mg).

$^1$H-NMR (270 MHz, CDCl$_3$) δ1.71–1.93 (m, 4H), 2.95 (t, J=7.1 Hz, 2H), 3.87 (s, 6H), 3.89 (t, J=6.9 Hz, 2H), 3.97 (s, 3H), 6.77 (d, J=7.9 Hz, 2H), 6.89 (t, J=7.3 Hz, 1H), 7.16–7.31 (m, 4H), 7.18 (s, 2H), 7.44 (d, J=8.3 Hz, 1H), 7.58 (d, J=7.9 Hz, 1H), 7.75 (s, 1H), 8.42(d, J=1.0 Hz, 1H), 8.68 (brs, 1H) EI-MS m/z=517 (M$^+$) Elemental Analysis: C$_{30}$H$_{31}$NO$_5$S Calcd.(%): C, 69.61; H, 6.04; N, 2.71 Found (%): C, 69.57; H, 6.36; N, 2.72

EXAMPLE 111

(E)-2-(3,4-Dihydroxybutyl)-3-(indol-3-yl)-1-(3,4,5-trimethoxyphenyl)-2-propen-1-one (Compound 111)

5,6-Dihydroxy-1-(3,4,5-trimethoxyphenyl)hexan-1-one (787.2 mg) obtained in Reference Example 21 and indole-3-carbaldehyde(382.8 mg) were dissolved in ethanol (7 ml), and piperidine (261.1 mg) was added thereto, followed by heating under reflux for 48 hours. N,N,N'-Trimethylethylenediamine (269.8 mg) was added to the reaction solution and the mixture was heated under reflux further for 48 hours. The reaction solution was concentrated under reduced pressure and the residue was purified by silica gel column chromatography. The obtained crude crystals were recrystallized from a mixed solvent of ethyl acetate and hexane (3:2) and then from ethanol to give Compound 111 (98.4 mg).

$^1$H-NMR (270 MHz, CDCl$_3$) δ1.67–1.94 (m, 2H), 2.33 (brt, J=5.8 Hz, 1H), 2.89 (m, 1H), 3.03 (m, 1H), 3.54 (m, 1H), 3.67 (m, 1H), 3.78 (m, 1H), 3.88 (s, 6H), 3.96 (brs, 1H), 3.97 (s, 3H), 7.00 (s, 2H), 7.17–7.31 (m, 2H), 7.44 (d, J=7.9 Hz, 1H), 7.54 (d, J=7.9 Hz, 1H), 7.77 (s, 1H), 7.87 (d, J=2.6 Hz, 1H), 8.92 (brs, 1H) FAB-MS m/z=426 (M$^+$+1) Elemental Analysis: C$_{24}$H$_{27}$NO$_6$·0.5H$_2$O Calcd.(%): C, 66.35; H, 6.50; N, 3.22 Found (%): C, 66.40; H, 6.67; N, 3.18

EXAMPLE 112

(E)-2-(3,4-Dihydroxybutyl)-3-(6-methylindol-3-yl)-1-(3,4,5-trimethoxyphenyl)-2-propen-1-one (Compound 112)

5,6-Dihydroxy-1-(3,4,5-trimethoxyphenyl)hexan-1-one (870.0 mg) obtained in Reference Example 21 and 6-methylindole-3-carbaldehyde (465.0 mg) were dissolved in ethanol (8 ml), and piperidine (288.8 mg) was added thereto, followed by heating under reflux for 48 hours. The reaction solution was concentrated under reduced pressure and the residue was purified by silica gel column chromatography. The obtained crude crystals were recrystallized from a mixed solvent of ethyl acetate and hexane (5:3) and then from a mixed solvent of ethanol and water (1:1) to give Compound 112 (142.7 mg).

$^1$H-NMR (270 MHz, CDCl$_3$) δ1.70–1.95 (m, 2H), 2.36 (brs, 1H), 2.47 (s, 3H), 2.87 (m, 1H), 3.03 (m, 1H), 3.54 (m, 1H), 3.65 (m, 1H), 3.77 (m, 1H), 3.88 (s, 6H), 3.96 (s, 3H), 4.04 (brs, 1H), 7.00 (s, 2H), 7.02 (d, J=8.8 Hz, 1H), 7.22 (s, 1H), 7.41 (d, J=8.8 Hz, 1H), 7.75 (s, 1H), 7.79 (d, J=2.3 Hz, 1H), 8.79 (s, 1H) FAB-MS m/z=440 (M$^+$+1) Elemental Analysis: C$_{25}$H$_{29}$NO$_6$·0.3H$_2$O Calcd.(%): C, 67.49; H, 6.71; N, 3.15 Found (%): C, 67.55; H, 6.93; N, 3.15

EXAMPLE 113

(Z)-2-(2,3-Dihydroxypropylthio)-3-(indol-3-yl)-1-(3,4,5-trimethoxyphenyl)-2-propen-1-one (Compound 113)

2-(2,3-Dihydroxypropylthio)-3',4',5'-trimethoxyacetophenone (3.16 g) obtained in Reference Example 16 and indole-3-carbaldehyde (1.45 g) were dissolved in ethanol (50 ml), and piperidine (0.85 g) was added thereto, followed by heating under reflux for 72 hours. The reaction solution was concentrated under reduced pressure and the residue was purified by silica gel column chromatography. The obtained crude crystals were recrystallized from a mixed solvent of ethanol and water (1:4) to give Compound 113 (2.04 g).

$^1$H-NMR (270 MHz, CDCl$_3$) δ2.31 (t, J=5.9 Hz, 1H), 2.83 (dd, J=13.9, 8.9 Hz, 1H), 3.09 (dd, J=13.9, 4.0 Hz, 1H), 3.58 (dt, J=11.2, 5.9 Hz, 1H), 3.69 (m, 1H), 3.79 (m, 1H), 3.88 (s, 6H), 3.97 (s, 3H), 4.11 (d, J=3.5 Hz, 1H), 7.11 (s, 2H), 7.21 (m, 1H), 7.29 (m, 1H), 7.46 (brd, J=7.9 Hz, 1H), 7.54 (brd, J=7.4 Hz, 1H), 7.97 (s, 1H), 8.61 (d, J=3.0 Hz, 1H), 9.01 (s, 1H) EI-MS m/z=443 (M$^+$) Elemental Analysis: C$_{23}$H$_{25}$NO$_6$S·0.9H$_2$O Calcd.(%): C, 60.09; H, 5.88; N, 3.05 Found (%): C, 60.11; H, 6.01; N, 3.03

EXAMPLE 114

(Z)-2-(2,3-Dihydroxypropylthio)-3-(1-methylindol-3-yl)-1-(3,4,5-trimethoxyphenyl)-2-propen-1-one (Compound 114)

2-(2,3-Dihydroxypropylthio)-3',4',5'-trimethoxyacetophenone (1.00 g) obtained in Reference Example 16 and 1-methylindole-3-carbaldehyde (0.50 g) were dissolved in ethanol (8 ml), and piperidine (0.31 g) was added thereto, followed by heating under reflux for 48 hours. The reaction solution was concentrated under reduced pressure and the residue was purified by silica gel column chromatography. The obtained crude crystals were recrystallized from a mixed solvent of ethanol and water (1:1) to give Compound 114 (844.8 mg).

$^1$H-NMR (270 MHz, CDCl$_3$) δ2.24 (t, J=6.3 Hz, 1H), 2.82 (dd, J=13.6, 8.7 Hz, 1H), 3.10 (dd, J=13.6, 3.5 Hz, 1H), 3.57 (m, 1H), 3.69 (m, 1H), 3.78 (m, 1H), 3.87 (s, 6H), 3.94 (s, 3H), 3.97 (s, 3H), 4.24 (d, J=4.0 Hz, 1H), 7.08 (s, 2H), 7.22 (m, 1H), 7.33 (m, 1H), 7.39 (d, J=7.9 Hz, 1H), 7.53 (d, J=7.9 Hz, 1H), 8.00 (s, 1H), 8.52 (s, 1H) FAB-MS m/z=458 (M$^+$+1) Elemental Analysis: C$_{24}$H$_{27}$NO$_6$S Calcd.(%): C, 63.00; H, 5.95; N, 3.06 Found (%): C, 62.85; H, 5.97; N, 3.02

EXAMPLE 115

(Z)-2-(2,3-Dihydroxypropylthio)-3-(4-methylindol-3-yl)-1-(3,4,5-trimethoxyphenyl)-2-propen-1-one (Compound 115)

2-(2,3-Dihydroxypropylthio)-3',4',5'-trimethoxyacetophenone (397.5 mg) obtained in Reference Example 16 and 4-methylindole-3-carbaldehyde (W095/14003) (200.0 mg) were dissolved in ethanol (2 ml), and piperidine (107.3 mg) was added thereto, followed by heating under reflux for 48 hours. The reaction solution was concentrated under reduced pressure and the residue was purified by silica gel column chromatography. The obtained crude crystals were recrystallized from a mixed solvent of ethyl acetate and hexane (2:1) and purified by preparative HPLC (YMC pack ODS, SH-343-5, S-5, 120A, 250×20 mm, acetonitrile:water=40:60). The eluate was concentrated under reduced pressure and the residue was recrystallized from isopropyl ether to give Compound 115 (249.0 mg).

$^1$H-NMR (270 MHz, CDCl$_3$) δ2.38 (t, J=5.8 Hz, 1H), 2.41 (s, 3H), 2.83 (dd, J=13.9, 8.6 Hz, 1H), 3.08 (dd, J=13.9, 4.0 Hz, 1H), 3.57 (dt, J=11.3, 5.8 Hz, 1H), 3.70 (m, 1H), 3.81 (m, 1H), 3.88 (s, 6H), 3.94 (s, 3H), 4.13 (d, J=3.3 Hz, 1H), 6.93 (d, J=7.6 Hz, 1H), 7.05 (s, 2H), 7.14 (t, J=7.6 Hz, 1H), 7.30 (d, J=7.6 Hz, 1H), 8.32 (s, 1H), 8.69 (d, J=3.0 Hz, 1H), 9.07 (s, 1H) FAB-MS m/z=458 (M$^+$+1) Elemental Analysis: C$_{24}$H$_{27}$NO$_6$S Calcd.(%): C, 63.00; H, 5.95; N, 3.06 Found (%): C, 63.00; H, 5.96; N, 3.05

EXAMPLE 116

(Z)-3-(4-Chloroindol-3-yl)-2-(2,3-dihydroxypropylthio)-1-(3,4,5-trimethoxyphenyl)-2-propen-1-one (Compound 116)

2-(2,3-Dihydroxypropylthio)-3',4',5'-trimethoxyacetophenone (948.0 mg) obtained in Reference Example 16 and 4-chloroindole-3-carbaldehyde [Can. J. Chem., 41, 1585 (1963)] (537.0 mg) were dissolved in ethanol (6 ml), and piperidine (296.7 mg) was added thereto, followed by heating under reflux for 48 hours. The reaction solution was concentrated under reduced pressure and the residue was purified by silica gel column chromatography. The obtained crude crystals were recrystallized from a mixed solvent of ethyl acetate and hexane (5:3) to give Compound 116 (909.9 mg).

$^1$H-NMR (270 MHz, CDCl$_3$) δ2.48 (brs, 1H), 2.87 (dd, J=13.6, 8.4 Hz, 1H), 3.08 (dd, J=13.6, 4.0 Hz, 1H), 3.58 (m, 1H), 3.72 (m, 1H), 3.83 (m, 1H), 3.91 (s, 6H), 3.94 (s, 3H), 4.00 (d, J=3.6 Hz, 1H), 7.11 (s, 2H), 7.15–7.17 (m, 2H), 7.38 (m, 1H), 8.64 (d, J=2.6 Hz, 1H), 8.77 (s, 1H), 9.37 (s, 1H) FAB-MS m/z=478, 480 (M$^+$+1) Elemental Analysis: C$_{23}$H$_{24}$ClNO$_6$S Calcd. (%): C, 57.80; H, 5.06; N, 2.93 Found (%): C, 58.08; H, 5.16; N, 2.86

EXAMPLE 117

(Z)-2-(2,3-Dihydroxypropylthio)-3-(5-methylindol-3-yl)-1-(3,4,5-trimethoxyphenyl)-2-propen-1-one (Compound 117)

2-(2,3-Dihydroxypropylthio)-3',4',5'-trimethoxyacetophenone (948.0 mg) obtained in Reference Example 16 and 5-methylindole-3-carbaldehyde (WO95/14003) (477.0 mg) were dissolved in ethanol (6 ml), and piperidine (255.5 mg) was added thereto, followed by heating under reflux for 36 hours. The reaction solution was concentrated under reduced pressure and the residue was purified by silica gel column chromatography. The obtained crude crystals were recrystallized from a mixed solvent of ethanol and water (2:3) to give Compound 117 (710.9 mg).

$^1$H-NMR (270 MHz, CDCl$_3$) δ2.32 (t, J=5.9 Hz, 1H), 2.43 (s, 3H), 2.81 (dd, J=13.7, 8.6 Hz, 1H), 3.08 (dd, J=13.7, 3.8 Hz, 1H), 3.56 (m, 1H), 3.68 (m, 1H), 3.78 (m, 1H), 3.89 (s, 6H), 3.97 (s, 3H), 4.15 (d, J=3.6 Hz, 1H), 7.11 (m, 1H), 7.12 (s, 2H), 7.30 (brs, 1H), 7.34 (d, J=8.3 Hz, 1H), 7.95 (brs, 1H), 8.58 (d, J=3.0 Hz, 1H), 8.90 (s, 1H) FAB-MS m/z=458 (M$^+$+1) Elemental Analysis: C$_{24}$H$_{27}$NO$_6$S Calcd.(%): C, 63.00; H, 5.95; N, 3.06 Found (%): C, 63.33; H, 6.10; N, 3.13

EXAMPLE 118

(Z)-3-(5-Chloroindol-3-yl)-2-(2,3-dihydroxypropylthio)-1-(3,4,5-trimethoxyphenyl)-2-propen-1-one (Compound 18)

2-(2,3-Dihydroxypropylthio)-3',4',5'-trimethoxyacetophenone (948.0 mg) obtained in Reference Example 16 and 5-chloroindole-3-carbaldehyde (WO95/14003) (537.0 mg) were dissolved in ethanol (6 ml), and piperidine (296.7 mg) was added thereto, followed by heating under reflux for 48 hours. The reaction solution was concentrated under reduced pressure and the residue was purified by silica gel column chromatography. The obtained crude crystals were recrystallized from ethyl acetate to give Compound 118 (837.2 mg).

$^1$H-NMR (270 MHz, DMSO-d$_6$) δ2.78 (dd, J=13.2, 7.3 Hz, 1H), 2.90 (dd, J=13.2, 4.6 Hz, 1H), 3.29–3.39 (m, 2H), 3.55 (m, 1H), 3.80 (s, 3H), 3.82 (s, 6H), 4.55 (t, J=5.6 Hz, 1H), 4.86 (d, J=5.3 Hz, 1H), 7.13 (s, 2H), 7.18 (dd, J=8.8, 2.0 Hz, 1H), 7.50 (d, J=8.8 Hz, 1H), 7.54 (s, 1H), 7.59 (d, J=2.0 Hz, 1H), 8.45 (s, 1H), 12.00 (brs, 1H) FAB-MS m/z=478, 480 (M$^+$+1) Elemental Analysis: C$_{23}$H$_{24}$ClNO$_6$S Calcd.(%): C, 57.80; H, 5.06; N, 2.93 Found (%): C, 57.86; H, 5.13; N, 2.76

EXAMPLE 119

(Z)-2-(2,3-Dihydroxypropylthio)-3-(5-fluoroindol-3-yl)-1-(3,4,5-trimethoxyphenyl)-2-propen-1-one (Compound 119)

2-(2,3-Dihydroxypropylthio)-3',4',5'-trimethoxyacetophenone (948.0 mg) obtained in Reference Example 16 and 5-fluoroindole-3-carbaldehyde (WO95/14003) (489.0 mg) were dissolved in ethanol (20 ml), and piperidine (85.0 mg) was added thereto, followed by heating under reflux for 36 hours. The reaction solution was concentrated under reduced pressure and the residue was purified by silica gel column chromatography. The obtained crude crystals were recrystallized from a mixed solvent of ethanol and water (1:1) to give Compound 119 (618.1 mg).

$^1$H-NMR (270 MHz, DMSO-d$_6$) δ2.78 (dd, J=13.1, 7.2 Hz, 1H), 2.90 (dd, J=13.1, 4.7 Hz, 1H), 3.25–3.40 (m, 2H), 3.54 (m, 1H), 3.79 (s, 3H), 3.81 (s, 6H), 4.56 (t, J=5.7 Hz, 1H), 4.87 (d, J=5.4 Hz, 1H), 7.02 (td, J=9.0, 2.5 Hz, 1H), 7.11 (s, 2H), 7.31 (dd, J=9.9, 2.5 Hz, 1H), 7.48 (dd, J=9.0, 4.0 Hz, 1H), 7.53 (s, 1H), 8.48 (s, 1H), 11.96 (brs, 1H) EI-MS m/z=461 (M$^+$) Elemental Analysis: C$_{23}$H$_{24}$FNO$_6$S.0.9H$_2$O Calcd.(%): C, 57.83; H, 5.44; N, 2.93 Found (%): C, 57.89; H, 5.53; N, 2.93

EXAMPLE 120

(Z)-2-(2,3-Dihydroxypropylthio)-3-(6-methylindol-3-yl)-1-(3,4,5-trimethoxyphenyl)-2-propen-1-one (Compound 120)

2-(2,3-Dihydroxypropylthio)-3',4',5'-trimethoxyacetophenone (1.58 g) obtained in Reference Example 16 and 6-methylindole-3-carbaldehyde (975.0 mg) were dissolved in ethanol (10 ml), and piperidine (494.5 mg) was added thereto, followed by heating under reflux for 36 hours. The reaction solution was concentrated under reduced pressure and the residue was purified by silica gel column chromatography. The obtained crude crystals were recrystallized from a mixed solvent of ethyl acetate and hexane (5:3) to give Compound 120 (1.23 g).

$^1$H-NMR (270 MHz, CDCl$_3$) δ2.36 (s, 1H), 2.46 (s, 3H), 2.82 (dd, J=13.9, 8.9 Hz, 1H), 3.08 (dd, J=13.9, 4.0 Hz, 1H), 3.55 (m, 1H), 3.68 (m, 1H), 3.77 (m, 1H), 3.87 (s, 6H), 3.97 (s, 3H), 4.16 (s, 1H), 7.04 (d, J=7.7 Hz, 1H), 7.10 (s, 2H), 7.24 (s, 1H), 7.41 (d, J=7.7 Hz, 1H), 7.96 (s, 1H), 8.54 (d, J=3.0 Hz, 1H), 8.96 (s, 1H) EI-MS m/z=457 (M$^+$) Elemental Analysis: C$_{24}$H$_{27}$NO$_6$S.0.2H$_2$O Calcd.(%): C, 62.51; H, 5.99; N, 3.04 Found (%): C, 62.46; H, 6.11; N, 2.95

EXAMPLE 121

(Z)-2-(2,3-Dihydroxypropylthio)-3-(6-ethylindol-3-yl)-1-(3,4,5-trimethoxyphenyl)-2-propen-1-one (Compound 121)

2-(2,3-Dihydroxypropylthio)-3',4',5'-trimethoxyacetophenone (2.21 g) obtained in Reference Example 16 and 6-ethylindole-3-carbaldehyde (WO95/14003) (1.21 g) were dissolved in ethanol (14 ml), and piperidine (596.1 mg) was added thereto, followed by heating under reflux for 30 hours. The reaction solution was concentrated under reduced pressure and the residue was purified by silica gel column chromatography. The obtained crude crystals were recrystallized from a mixed solvent of ethanol and water (2:3) to give Compound 121 (1.48 g).

$^1$H-NMR (270 MHz, DMSO-d$_6$) δ1.22 (t, J=7.6 Hz, 3H), 2.70 (q, J=7.6 Hz, 2H), 2.80 (dd, J=13.3, 7.3 Hz, 1H), 2.91 (dd, J=13.3, 4.6 Hz, 1H), 3.33 (m, 2H), 3.55 (m, 1H), 3.79 (s, 3H), 3.81 (s, 6H), 4.57 (t, J=5.5 Hz, 1H), 4.87 (d, J=5.5 Hz, 1H), 6.98 (d, J=8.1 Hz, 1H), 7.10 (s, 2H), 7.28 (s, 1H), 7.38 (d, J=8.1 Hz, 1H), 7.60 (s, 1H), 8.37 (d, J=2.3 Hz, 1H), 11.79 (d, J=2.3 Hz, 1H) FAB-MS m/z=472 (M$^+$+1) Elemental Analysis: C$_{25}$H$_{29}$NO$_6$S Calcd.(%): C, 63.68; H, 6.20; N, 2.97 Found (%): C, 63.79; H, 6.34; N, 2.93

EXAMPLE 122

(Z) -2-(2,3-Dihydroxypropylthio)-3-(6-isopropylindol-3-yl)-1-(3,4,5-trimethoxyphenyl)-2-propen-1-one (Compound 122)

2-(2,3-Dihydroxypropylthio) -3',4',5'-trimethoxyacetophenone (1.58 g) obtained in Reference Example 16 and 6-isopropylindole-3-carbaldehyde (WO95/14003) (935.0 mg) were dissolved in ethanol (10 ml), and piperidine (425.8 mg) was added thereto, followed by heating under reflux for 24 hours. The reaction solution was concentrated under reduced pressure and the residue was purified by silica gel column chromatography. The obtained crude crystals were recrystallized from a mixed solvent of ethyl acetate and hexane (1:1) to give Compound 122 (1.23 g).

$^1$H-NMR (270 MHz, CDCl$_3$) δ1.30 (d, J=6.9 Hz, 6H), 2.33 (t, J=6.1 Hz, 1H), 2.81 (dd, J=13.5, 8.7 Hz, 1H), 3.03 (m, 1H), 3.08 (dd, J=13.5, 3.6 Hz, 1H), 3.56 (m, 1H), 3.63–3.83 (m, 2H), 3.88 (s, 6H), 3.97 (s, 3H), 4.19 (d, J=3.0 Hz, 1H), 7.10 (s, 2H), 7.13 (d, J=8.3 Hz, 1H), 7.30 (s, 1H), 7.43 (d, J=8.3 Hz, 1H), 7.97 (s, 1H), 8.57 (d, J=3.0 Hz, 1H), 8.92 (brs, 1H) FAB-MS m/z=486 (M$^+$+1) Elemental Analysis: C$_{26}$H$_{31}$NO$_6$S.0.6H$_2$O Calcd.(%): C, 63.45; H, 6.62; N, 2.69 Found (%): C, 63.66; H, 6.71; N, 2.90

EXAMPLE 123

(Z)-3-(6-Chloroindol-3-yl)-2-(2,3-dihydroxypropylthio)-1-(3,4,5-trimethoxyphenyl)-2-propen-1-one (Compound 123)

2-(2,3-Dihydroxypropylthio)-3',4',5'-trimethoxy-acetophenone (948.0 mg) obtained in Reference Example 16 and 6-chloroindole-3-carbaldehyde (WO95/14003) (538.5 mg) were dissolved in ethanol (20 ml), and piperidine (255.0 mg) was added thereto, followed by heating under reflux for 38 hours. The reaction solution was concentrated under reduced pressure and the residue was purified by silica gel column chromatography. The obtained crude crystals were recrystallized from a mixed solvent of ethyl acetate and hexane (1:1) to give Compound 123 (270.3 mg).

$^1$H-NMR (270 MHz, CDCl$_3$) δ2.51 (s, 1H), 2.86 (dd, J=13.9, 8.4 Hz, 1H), 3.06 (dd, J=13.9, 4.0 Hz, 1H), 3.56 (m, 1H), 3.68 (m, 1H), 3.78 (m, 1H), 3.88 (s, 6H), 3.97 (s, 3H), 4.04 (s, 1H), 7.11 (s, 2H), 7.16 (dd, J=8.9, 1.8 Hz, 1H), 7.43 (d, J=8.9 Hz, 1H), 7.46 (d, J=1.8 Hz, 1H), 7.83 (s, 1H), 8.57 (d, J=3.0 Hz, 1H), 9.25 (s, 1H) FAB-MS m/z=478, 480 (M$^+$+1) Elemental Analysis: C$_{23}$H$_{24}$ClNO$_6$S.0.9H$_2$O Calcd. (%): C, 57.83; H, 5.44; N, 2.93 Found (%): C, 57.89; H, 5.53; N, 2.93

EXAMPLE 124

(Z)-2-(2,3-Dihydroxypropylthio)-3-(6-fluoroindol-3-yl)-1-(3,4,5-trimethoxyphenyl)-2-propen-1-one (Compound 124)

2-(2,3-Dihydroxypropylthio)-3',4',5'-trimethoxy-acetophenone (1.62 g) obtained in Reference Example 16 and 6-fluoroindole-3-carbaldehyde [J. Med. Chem., 6, 716 (1963)] (838.2 mg) were dissolved in ethanol (10 ml), and piperidine (437.7 mg) was added thereto, followed by heating under reflux for 36 hours. The reaction solution was concentrated under reduced pressure and the residue was purified by silica gel column chromatography. The obtained crude crystals were recrystallized from ethanol to give Compound 124 (638.8 mg).

$^1$H-NMR (270 MHz, CDCl$_3$) δ2.34 (t, J=6.3 Hz, 1H), 2.84 (dd, J=13.8, 8.6 Hz, 1H), 3.08 (dd, J=13.8, 3.8 Hz, 1H), 3.58 (m, 1H), 3.69 (m, 1H), 3.79 (m, 1H), 3.88 (s, 6H), 3.97 (s, 3H), 3.99 (d, J=4.0 Hz, 1H), 6.97 (td, J=8.9, 2.2 Hz, 1H), 7.11 (s, 2H), 7.15 (dd, J=9.1, 2.2 Hz, 1H), 7.45 (dd, J=8.9, 5.0 Hz, 1H), 7.84 (s, 1H), 8.55 (d, J=2.6 Hz, 1H), 9.10 (brs, 1H) FAB-MS m/z=462 (M$^+$+1) Elemental Analysis: C$_{23}$H$_{24}$FNO$_6$S Calcd.(%): C, 59.86; H, 5.24; N, 3.04 Found (%) : C, 59.68; H, 5.17; N, 2.89

EXAMPLE 125

(Z)-3-(6-Acetamidoindol-3-yl)-2-(2,3-dihydroxypropylthio)-1-(3,4,5-trimethoxyphenyl)-2-propen-1-one (Compound 125)

2-(2,3-Dihydroxypropylthio)-3',4',5'-trimethoxy-acetophenone (1.58 g) obtained in Reference Example 16 and 6-acetoamidoindole-3-carbaldehyde (WO95/14003) (1.64 g) were dissolved in ethanol (20 ml), and piperidine (690.0 mg) was added thereto, followed by heating under reflux for 38 hours. The precipitated crystals were collected by filtration and the obtained crude crystals were recrystallized from a mixed solvent of ethanol, methanol, N,N-dimethylformamide, and water to give Compound 125 (707.3 mg).

$^1$H-NMR (270 MHz, DMSO-d$_6$) δ2.05 (s, 3H), 2.79 (dd, J=13.4, 6.9 Hz, 1H), 2.91 (dd, J=13.4, 5.0 Hz, 1H), 3.27–3.38 (m, 2H), 3.54 (m, 1H), 3.79 (s, 3H), 3.81 (s, 6H), 4.55 (t, J=5.7 Hz, 1H), 4.86 (d, J=5.0 Hz, 1H), 7.09 (s, 2H), 7.10 (dd, J=8.9, 1.5 Hz, 1H), 7.38 (d, J=8.9 Hz, 1H), 7.57 (s, 1H), 8.07 (d, J=1.5 Hz, 1H), 8.36 (s, 1H), 9.92 (s, 1H), 11.80 (s, 1H) EI-MS m/z=500 (M$^+$) Elemental Analysis: C$_{25}$H$_{28}$N$_2$O$_7$S Calcd.(%): C, 59.99; H, 5.64; N, 5.60 Found (%): C, 59.97; H, 5.74; N, 5.72

EXAMPLE 126

(Z)-3-(6-Acetamido-1-methylindol-3-yl)-2-(2,3-dihydroxypropylthio)-1-(3,4,5-trimethoxyphenyl)-2-propen-1-one (Compound 126)

Compound 125 (300.0 mg) obtained in Example 125 was dissolved in a mixed solvent of N,N-dimethylformamide and tetrahydrofuran (1:1), and methyl iodide (93.6 mg) and then sodium hydride (26.4 mg, 60% mineral oil dispersion) were added thereto, followed by stirring for 1.5 hours. The reaction solution was subjected to partitioning between chloroform and water, and the organic layer was successively washed with water and a saturated saline, dried over anhydrous magnesium sulfate, and concentrated under reduced pressure. The obtained crude crystals were washed with chloroform and recrystallized from a mixed solvent of ethanol, N,N-dimethylformamide, and water to give Compound 126 (249.7 mg).

$^1$H-NMR (270 MHz, DMSO-d$_6$) δ2.06 (s, 3H), 2.80 (dd, J=13.2, 7.3 Hz, 1H), 2.91 (dd, J=13.2, 4.6 Hz, 1H), 3.27–3.38 (m, 2H), 3.53 (m, 1H), 3.79 (s, 3H), 3.80 (s, 6H), 3.86 (s, 3H), 4.54 (brs, 1H), 4.85 (d, J=4.6 Hz, 1H), 7.09 (s, 2H), 7.14 (d, J=8.8 Hz, 1H), 7.40 (d, J=8.8 Hz, 1H), 7.54 (s, 1H), 8.01 (s, 1H), 8.37 (s, 1H), 9.92 (s, 1H) EI-MS m/z=514 (M$^+$) Elemental Analysis: C$_{26}$H$_{30}$N$_2$O$_7$S Calcd.(%): C, 60.69; H, 5.88; N, 5.44 Found (%): C, 60.73; H, 5.99; N, 5.29

EXAMPLE 127

3-(Indol-3-yl)-2-[(2S),(3R)-2,3,4-trihydroxybutylthio]-1-(3,4,5-trimethoxyphenyl)-2-propen-1-one (Compound 127)

3',4',5'-Trimethoxy-2-[(2S),(3R)-2,3,4-trihydroxybutylthio]acetophenone (268.0 mg) obtained in Reference Example 22 and indole-3-carbaldehyde (112.3 mg) were dissolved in ethanol (4 ml), and piperidine (66.0 mg) was added thereto, followed by heating under reflux for 96 hours. The reaction solution was concentrated under reduced pressure and the residue was purified by silica gel column chromatography. The obtained crude crystals were recrystallized from a mixed solvent of ethyl acetate and hexane to give Compound 127 (56.9 mg).

$^1$H-NMR (270 MHz, CDCl$_3$) δ2.96 (dd, J=13.6, 8.7 Hz, 1H), 3.09 (dd, J=13.6, 4.0 Hz, 1H), 3.23 (brs, 1H), 3.52–3.82 (m, 5H), 3.84 (s, 6H), 3.96 (s, 3H), 4.81 (d, J=2.0 Hz, 1H), 7.08 (s, 2H), 7.17 (m, 1H), 7.24 (m, 1H), 7.42 (d, J=7.6 Hz, 1H), 7.49 (d. J=7.6 Hz, 1H), 7.98 (s, 1H), 8.65 (d, J=2.6 Hz, 1H), 9.56 (brs, 1H) FAB-MS m/z=474 (M$^+$+1) Elemental Analysis: C$_{24}$H$_{27}$NO$_7$S.0.6H$_2$O Calcd.(%): C, 59.52; H, 5.88; N, 2.89 Found (%): C, 59.60; H, 5.96; N, 2.86

EXAMPLE 128

3-(6-Methylindol-3-yl)-2-[(2S),(3R)-2,3,4-trihydroxy-butylthio]-1-(3,4,5-trimethoxyphenyl)-2-propen-1-one (Compound 128)

3',4',5'-Trimethoxy-2-[(2S),(3R)-2,3,4-trihydroxy-butylthio]acetophenone (1.73 g) obtained in Reference Example 22 and 6-methylindole-3-carbaldehyde (0.80 g) were dissolved in ethanol (10 ml), and piperidine (0.43g) was added thereto, followed by heating under reflux for 26 hours. The reaction solution was concentrated under reduced pressure and the residue was purified by silica gel column chromatography. The obtained crude crystals were recrystallized from a mixed solvent of ethyl acetate and hexane to give Compound 128 (1.22 g).

$^1$H-NMR (270 MHz, CDCl$_3$) δ2.43 (s, 3H), 2.96 (dd, J=13.6, 8.7 Hz, 1H), 3.10 (dd, J=13.6, 4.0 Hz, 1H), 3.23 (brs, 1H), 3.53–3.82 (m, 5H), 3.84 (s, 6H), 3.96 (s, 3H), 4.84 (brs, 1H), 7.00 (d, J=8.2 Hz, 1H), 7.07 (s, 2H), 7.20 (s, 1H), 7.36 (d, J=8.2 Hz, 1H), 7.97 (s, 1H), 8.59 (d, J=2.6 Hz, 1H), 9.39 (brs, 1H) FAB-MS m/z=488 (M$^+$+1) Elemental Analysis: C$_{25}$H$_{29}$NO$_7$S Calcd.(%): C, 61.59; H, 6.00; N, 2.87 Found (%): C, 61.26; H, 6.12; N, 2.82

EXAMPLE 129

3-(6-Methylindol-3-yl)-2-[(2R),(3S)-2,3,4-trihydroxy-butylthio]-1-(3,4,5-trimethoxyphenyl)-2-propen-1-one (Compound 129)

3',4',5'-Trimethoxy-2-[(2R),(3S)-2,3,4-trihydroxy-butylthio]acetophenone (1.73 g) obtained in Reference Example 23 and 6-methylindole-3-carbaldehyde (0.80 g) were dissolved in ethanol (10 ml), and piperidine (0.43g) was added thereto, followed by heating under reflux for 48 hours. The reaction solution was concentrated under reduced pressure and the residue was purified by silica gel column chromatography. The obtained crude crystals were recrystallized from a mixed solvent of ethyl acetate and hexane to give Compound 129 (1.12 g).

$^1$H-NMR (270 MHz, CDCl$_3$) δ2.43 (s, 3H), 2.95 (dd, J=13.6, 8.7 Hz, 1H), 3.10 (dd, J=13.6, 4.0 Hz, 1H), 3.17 (brs, 1H), 3.53 (d, J=6.3 Hz, 1H), 3.64–3.82 (m, 4H), 3.84 (s, 6H), 3.96 (s, 3H), 4.83 (d, J=4.0 Hz, 1H), 7.01 (d, J=8.2 Hz, 1H), 7.07 (s, 2H), 7.20 (s, 1H), 7.37 (d, J=8.2 Hz, 1H), 7.97 (s, 1H), 8.59 (d, J 2.6 Hz, 1H), 9.36 (brs, 1H) FAB-MS m/z=488 (M$^+$+1) Elemental Analysis: C$_{25}$H$_{29}$NO$_7$S Calcd.(%): C, 61.59; H, 6.00; N, 2.87 Found (%): C, 61.56; H, 6.14; N, 2.82

EXAMPLE 130

2-(2,3-Dihydroxypropylthio)-3-(indol-5-yl)-1-(3,4,5-trimethoxyphenyl)-2-propen-1-one (Compound 130a, Compound 130b)

2-(2,3-Dihydroxypropylthio)-3',4',5'-trimethoxy-acetophenone (316.0 mg) obtained in Reference Example 16 and indole-5-carbaldehyde (145.0 mg) obtained in Reference Example 24 were dissolved in ethanol (5 ml), and piperidine (850.0 mg) was added thereto, followed by heating under reflux for 72 hours. The reaction solution was concentrated under reduced pressure and the residue was purified by silica gel column chromatography. The obtained mixture was purified by preparative HPLC (YMC pack ODS, SH-343-5, S-5, 120A, 250×20 mm, acetonitrile:water=35:65) and the eluates were concentrated under reduced pressure to give Compound 130a (36.4 mg, Z form) and Compound 130b (17.0 mg, E form).

Compound 130a:

$^1$H-NMR (270 MHz, CDCl$_3$) δ2.01 (brs, 1H), 2.62 (brs, 1H), 2.82 (dd, J=13.8, 8.4 Hz, 1H), 2.99 (dd, J=13.8, 4.0 Hz, 1H), 3.54 (dd, J=11.8, 5.8 Hz, 1H), 3.66 (dd, J=11.4, 3.5 Hz, 1H), 3.78 (m, 1H), 3.92 (s, 6H), 3.99 (s, 3H), 6.64 (brs, 1H), 7.21 (s, 2H), 7.28–7.31 (m, 2H), 7.46 (brd, J=8.6 Hz, 1H), 7.84 (dd, J=8.6, 1.3 Hz, 1H), 8.25 (s, 1H), 8.85 (s, 1H) FAB-MS m/z=444 (M$^+$+1)

Compound 130b:

$^1$H-NMR (270 MHz, CDCl$_3$) δ2.66 (brs, 1H), 2.81 (dd, J=14.3, 6.9 Hz, 1H), 2.89 (dd, J=14.3, 5.5 Hz, 1H), 3.23 (brs, 1H), 3.67–3.98 (m, 3H), 3.83 (s, 6H), 3.90 (s, 3H), 6.47 (brs, 1H), 7.03 (dd, J=8.6, 1.3 Hz, 1H), 7.17–7.22 (m, 2H), 7.28 (s, 2H), 7.45 (s, 1H), 7.52 (s, 1H), 8.39 (s, 1H) FAB-MS m/z=444 (M$^+$+1)

Industrial Applicability

According to the present invention, there can be provided propenone derivatives having an excellent antitumor activity.

We claim:

1. A propenone derivative represented by the following formula (I):

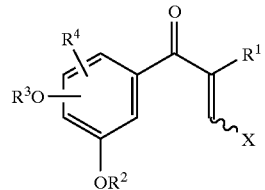

(I)

wherein R$^1$ represents hydrogen, substituted or unsubstituted lower alkyl, substituted or unsubstituted aryl, or YR$^5$ wherein Y represents S or O; and R$^5$ represents substituted or unsubstituted lower alkyl, substituted or unsubstituted aryl, substituted or unsubstituted heteroaryl, or a substituted or unsubstituted cyclic ether residue; R$^2$ represents hydrogen lower alkyl, or substituted or unsubstituted aralkyl; OR$^3$ represents lower alkoxy, or substituted or unsubstituted aralkyloxy on the 2-position or 6-position of the benzene ring; R$^4$ represents hydrogen, hydroxy, lower alkyl, substituted or unsubstituted aralkyl, lower alkoxy, substituted or unsubstituted aralkyloxy, or halogen; and X represents substituted or unsubstituted indolyl, with the proviso that when R$^1$ is hydrogen, unsubstituted lower alkyl, or substituted or unsubstituted aryl, and R$^4$ is on the 2-position or 6-position of the benzene ring, then R$^4$ is hydrogen, lower alkyl, substituted or unsubstituted aralkyl, lower alkoxy, substituted or unsubstituted aralkyloxy, or halogen or a pharmaceutically acceptable salt thereof.

2. A propenone derivative or a pharmaceutically acceptable salt thereof according to claim 1, wherein R$^4$ represents hydrogen, lower alkyl, or substituted or unsubstituted aryl.

3. A propenone derivative represented by the following formula (I):

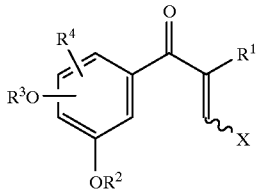

(I)

wherein $R^1$ represents hydrogen, substituted or unsubstituted lower alkyl, substituted or unsubstituted aryl, or $YR^5$ wherein Y represents S or O; and $R^5$ represents substituted or unsubstituted lower alkyl, substituted or unsubstituted aryl, substituted or unsubstituted heteroaryl, or a substituted or unsubstituting cyclic ether residue; $R^2$ and $R^3$ independently represent hydrogen, lower alkyl, or substituted or unsubstituted aralkyl, or alternatively $R^2$ and $R^3$ are combined to form substituted or unsubstituted methylene or ethylene; $R^4$ represents lower alkyl, substituted or unsubstituted aralkyl, or halogen; and X represents substituted or unsubstituted indolyl, with the proviso that when $R^1$ is hydrogen, unsubstituted lower alkyl, or substituted or unsubstituted aryl, and $OR^3$ is on the 2-position or 6-position of the benzene ring, $R^3$ is lower alkyl or substituted or unsubstituted aralkyl, or $R^2$ and $R^3$ are combined to form substituted or unsubstituted methylene or ethylene; or a pharmaceutically acceptable salt thereof.

4. A propenone derivative or a pharmaceutically acceptable salt thereof according to claim 3, wherein $R^1$ represents hydrogen, lower alkyl, or substituted or unsubstituted aryl.

5. A propenone derivative or a pharmaceutically acceptable salt thereof according to claim 3, wherein $R^2$ and $R^3$ are combined to form substituted or unsubstituted methylene or ethylene.

6. A propenone derivative or a pharmaceutically acceptable salt thereof according to claim 4, wherein $R^2$ and $R^3$ are combined to form substituted or unsubstituted methylene or ethylene.

7. A propenone derivative or a pharmaceutically acceptable salt thereof according to claim 3, wherein $OR^3$ represents lower alkoxy, or substituted or unsubstituted aralkyloxy on the 2-position or 6-position of the benzene ring.

8. A propenone derivative or a pharmaceutically acceptable salt thereof according to claim 4, wherein $OR^3$ represents lower alkoxy, or substituted or unsubstituted aralkyloxy on the 2-position or 6-position of the benzene ring.

9. A propenone derivative or a pharmaceutically acceptable salt thereof according to claim 3, wherein $OR^3$ and $R^4$ are on the 4-position or 5-position of the benzene ring.

10. A propenone derivative or a pharmaceutically acceptable salt thereof according to claim 4, wherein $OR^3$ and $R^4$ are on the 4-position or 5-position of the benzene ring.

11. A propenone derivative represented by the following formula (I):

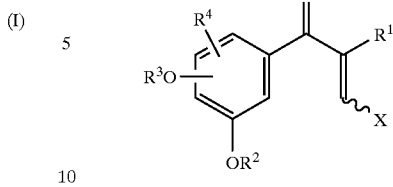

(I)

wherein $R^1$ represents substituted lower alkyl or $YR^5$ wherein Y represents S or O; and $R^5$ represents substituted or unsubstituted lower alkyl, substituted or unsubstituted aryl, substituted or unsubstituted heteroaryl, or a substituted or unsubstituted cyclic ether residue; $R^2$ and $R^3$ independently represent hydrogen, lower alkyl, or substituted or unsubstituted aralkyl, or alternatively $R^2$ and $R^3$ are combined to form substituted or unsubstituted methylene or ethylene; $R^4$ represents hydrogen, hydroxy, lower alkyl, substituted or unsubstituted aralkyl, lower alkoxy, substituted or unsubstituted aralkyloxy, or halogen; and X represents substituted or unsubstituted indolyl, or a pharmaceutically acceptable salt thereof.

12. A propenone derivative or a pharmaceutically acceptable salt thereof according to claim 11, wherein $R^1$ represents $YR^5$.

13. A propenone derivative or a pharmaceutically acceptable salt thereof according to claim 12, wherein Y represents S.

14. A propenone derivative or a pharmaceutically acceptable salt thereof according to claim 13, wherein $R^1$ represents substituted lower alkyl.

15. A propenone derivative or a pharmaceutically acceptable salt thereof according to one of claims 12 to 14, wherein X represents substituted or unsubstituted indol-3-yl.

16. A propenone derivative or a pharmaceutically acceptable salt thereof according to one of claims 12 to 15, wherein $OR^3$ and $R^4$ are on the 4-position or 5-position of the benzene ring.

17. A propenone derivative selected from the group consisting of (Z)-2-(2,3-dihydroxypropylthio)-3-(indol-3-yl)-1-(3,4,5-trimethoxyphenyl)-2-propen-1-one, (Z)-2-(2,3-dihydroxypropylthio)-3-(5-fluoroindol-3-yl)-1-(3,4,5-trimethoxyphenyl)-2-propen-1-one, (Z)-2-(2,3-dihydroxypropylthio)-3-(6-methylindol-3-yl)-1-(3,4,5-trimethoxyphenyl)-2-propen-1-one, and (Z)-3-(6-chloroindol-3-yl)-2-(2,3-dihydroxypropylthio)-1-(3,4,5-trimethoxyphenyl)-2-propen-1-one, or a pharmaceutically acceptable salt thereof.

18. 1-(4-Ethoxy-3,5-dimethoxyphenyl)-2-methyl-3-(6-methylindol-3-yl)-2-propen-1-one or a pharmaceutically acceptable salt thereof.

19. A propenone derivative represented by the following formula:

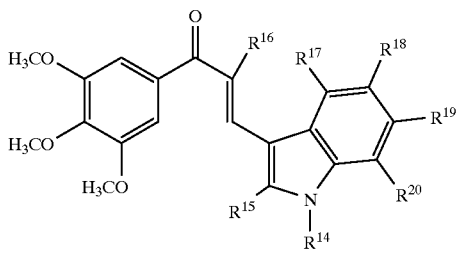

wherein $R^{14}$ represents hydrogen, lower alkyl, lower alkanoyl, lower alkoxycarbonyl, lower alkylsulfonyl, aralkyl, substituted or unsubstituted aroyl, substituted or unsubstituted arylsulfonyl, substituted or unsubstituted heteroarylcarbonyl, substituted or unsubstituted heteroarylsulfonyl, diglycolyl or

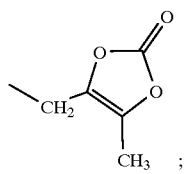

$R^{15}$ represents hydrogen, lower alkyl, halogen, substituted or unsubstituted aryl, or substituted or unsubstituted heteroaryl; $R^{16}$ represents hydrogen, lower alkyl or substituted or unsubstituted aryl; and $R^{17}$, $R^{18}$, $R^{19}$ and $R^{20}$ represent independently hydrogen, lower alkyl, lower alkoxy, aralkyloxy, hydroxy, nitro, halogen, trifluoromethyl or —$NR^{27}R^{28}$ (wherein $R^{27}$ and $R^{28}$ represent independently hydrogen, lower alkyl, lower alkanoyl, lower alkoxycarbonyl or substituted or unsubstituted aroyl), or a pharmaceutically acceptable salt thereof.

20. A propenone derivative or a pharmaceutically acceptable salt thereof according to claim 19, wherein $R^{14}$ and $R^{15}$ each represents hydrogen.

21. A propenone derivative or a pharmaceutically acceptable salt thereof according to claim 20, wherein $R^{16}$ represents hydrogen or lower alkyl.

22. A propenone derivative or a pharmaceutically acceptable salt thereof according to claim 21, wherein $R^{17}$, $R^{18}$, $R^{19}$ and $R^{20}$ represent independently hydrogen or lower alkyl.

23. A propenone derivative selected from the group consisting of (E)-3-(indol-3-yl)-1-(3,4,5-trimethoxyphenyl)-2-propen-1-one, (E)-3-(indol-3-yl)-2-methyl-1-(3,4,5-trimethoxyphenyl)-2-propen-1-one, (E)-2-methyl-3-(6-methylindol-3-yl)-1(3,4,5-trimethoxyphenyl)-2-propen-1-one, and (E)-3-(6-ethylindol-3-yl)-2-methyl-1-(3,4,5-trimethoxyphenyl)-2-propen-1-one, or a pharmaceutically acceptable salt thereof.

24. A propenone derivative or a pharmaceutically acceptable salt thereof according to claim 19, wherein $R^{14}$ represents substituted or unsubstituted aroyl.

25. The compound (E)-3-[1-(3,4,5-trimethoxybenzoyl)indol-3-yl]-1-(3,4,5-trimethoxyphenyl)-2-propen-1-one or a pharmaceutically acceptable salt thereof.

26. A pharmaceutically acceptable composition comprising a pharmaceutically acceptable carrier and an effective amount of a compound according to any one of claims 1 to 25 as an active ingredient.

* * * * *

UNITED STATES PATENT AND TRADEMARK OFFICE
CERTIFICATE OF CORRECTION

PATENT NO.    : 5,952,355
DATED         : September 14, 1999
INVENTOR(S)   : SHUN-ICHI IKEDA ET AL.

It is certified that error appears in the above-identified patent and that said Letters Patent is hereby corrected as shown below:

ON THE TITLE PAGE [30]:

Foreign Application Priority Data, Insert
    --Nov. 16, 1994  PCT application ... JP94/01934--.

COLUMN 6:

Line 66, "Suns" should read --Sons--.

COLUMN 7:

Line 38, "Suns" should read --Sons--.

COLUMN 11:

Line 23, "Compound (IIII)" should read
    --Compound (IIIi)--.

COLUMN 30:

Line 59, "intradermally" should read --intradermal--.

COLUMN 40:

Line 37, "satureted" should read --saturated--.

COLUMN 51:

Line 17, "(0.79g)" should read --(0.79g).--.

UNITED STATES PATENT AND TRADEMARK OFFICE
CERTIFICATE OF CORRECTION

PATENT NO. : 5,952,355
DATED : September 14, 1999
INVENTOR(S) : Shun-Ichi Ikeda, et al.

It is certified that error appears in the above-identified patent and that said Letters Patent is hereby corrected as shown below:

COLUMN 64:

Line 63, "(0.48g)" should read --(0.48g).--.

COLUMN 82:

Line 44, "the" (second occurrence) should be deleted.

Column 90, line 66, change "$R^4$" to --$R^1$--.

COLUMN 91:

Line 20, "unsubstituting" should read --unsubstituted--.

Signed and Sealed this

Thirtieth Day of January, 2001

Attest:

Q. TODD DICKINSON

*Attesting Officer*        *Director of Patents and Trademarks*